US00RE49466E

(19) United States
(12) Reissued Patent
Akhavan-Tafti et al.

(10) Patent Number: US RE49,466 E
(45) Date of Reissued Patent: Mar. 21, 2023

(54) SOLUTION PHASE HOMOGENEOUS ASSAYS

(71) Applicant: Beckman Coulter, Inc., Brea, CA (US)

(72) Inventors: Hashem Akhavan-Tafti, Howell, MI (US); Dean G. Binger, Saint Louis Park, MN (US); Ying Chen, Eden Prairie, MN (US); Renuka de Silva, Northville, MI (US); Terri McLernon, Mounds View, MN (US); James Mendoza, Robbinsdale, MN (US); Bruce H. Odegaard, Crystal, MN (US); Michael Salvati, Minnetrista, MN (US); Nir Shapir, Falcon Heights, MN (US); Wenhua Xie, Novi, MI (US)

(73) Assignee: Beckman Coulter, Inc., Brea, CA (US)

(21) Appl. No.: 16/945,391

(22) Filed: Jul. 31, 2020

Related U.S. Patent Documents

Reissue of:
(64) Patent No.: 10,036,708
Issued: Jul. 31, 2018
Appl. No.: 14/677,524
Filed: Apr. 2, 2015

U.S. Applications:
(63) Continuation of application No. 12/714,346, filed on Feb. 26, 2010, now Pat. No. 9,029,092.

(60) Provisional application No. 61/300,318, filed on Feb. 1, 2010, provisional application No. 61/156,473, filed on Feb. 27, 2009.

(51) Int. Cl.

| | |
|---|---|
| ***G01N 21/76*** | (2006.01) |
| ***C09B 15/00*** | (2006.01) |
| ***C12Q 1/28*** | (2006.01) |
| ***G01N 33/542*** | (2006.01) |
| ***G01N 33/58*** | (2006.01) |

(52) U.S. Cl.
CPC ..... *G01N 21/76* (2013.01); *C09B 15/00* (2013.01); *C12Q 1/28* (2013.01); *G01N 21/763* (2013.01); *G01N 33/542* (2013.01); *G01N 33/582* (2013.01)

(58) Field of Classification Search
CPC .... G01N 21/76; G01N 21/763; G01N 33/542; G01N 33/582; G01N 33/52; C09B 15/00; C12Q 1/28
See application file for complete search history.

(56) References Cited

U.S. PATENT DOCUMENTS

| | | | | |
|---|---|---|---|---|
| 4,837,395 | A | 6/1989 | Leeder et al. | |
| 4,943,525 | A * | 7/1990 | Dawson | G01N 33/542 435/14 |
| 5,089,383 | A | 2/1992 | Leeder et al. | |
| 5,098,828 | A | 3/1992 | Geiger et al. | |
| 5,171,668 | A | 12/1992 | Sugiyama | |
| 5,206,149 | A | 4/1993 | Oyama et al. | |
| 5,324,835 | A | 6/1994 | Yamaguchi | |
| 5,420,275 | A | 5/1995 | Masuya et al. | |
| 5,424,440 | A | 6/1995 | Klem et al. | |
| 5,491,072 | A | 2/1996 | Akhavan-Tafti et al. | |
| 5,512,451 | A | 4/1996 | Kricka | |
| 5,523,212 | A | 6/1996 | Akhavan-Tafti et al. | |
| 5,593,845 | A | 1/1997 | Akhavan-Tafti et al. | |
| 5,922,558 | A | 7/1999 | Akhavan-Tafti | |
| 6,030,803 | A | 2/2000 | Jacquemijns et al. | |
| 6,406,913 | B1 | 6/2002 | Ullman et al. | |
| 6,696,569 | B2 | 2/2004 | Akhavan-Tafti et al. | |
| 6,891,057 | B2 | 5/2005 | Akhavan-Tafti et al. | |
| 6,911,305 | B2 | 6/2005 | Levison et al. | |
| 7,732,153 | B2 * | 6/2010 | Akhavan-Tafti | G01N 33/54306 422/400 |
| 8,076,092 | B2 * | 12/2011 | Akhavan-Tafti | C12Q 1/28 422/50 |
| 8,124,362 | B2 * | 2/2012 | Akhavan-Tafti | G01N 33/54306 422/402 |
| 9,029,092 | B2 | 5/2015 | Akhavan-Tafti et al. | |
| 2002/0110842 | A1 | 8/2002 | Bystryak et al. | |
| 2007/0172878 | A1 | 7/2007 | Akhavan-Tafti et al. | |
| 2007/0264664 | A1 | 11/2007 | Akhavan-Tafti | |
| 2007/0264665 | A1 | 11/2007 | Akhavan-Tafti | |
| 2013/0084652 | A1 | 4/2013 | Shapir et al. | |

FOREIGN PATENT DOCUMENTS

| | | | |
|---|---|---|---|
| AU | 2010217756 | | 7/2016 |
| AU | 2010217756 | B2 | 7/2016 |
| EP | 0202081 | | 5/1986 |
| EP | 0202081 | A2 | 11/1986 |
| EP | 0315364 | | 1/1988 |
| EP | 0315364 | A2 | 5/1989 |
| EP | 2401392 | | 1/2017 |
| EP | 2401392 | B1 | 1/2017 |
| JP | 2723128 | B2 | 5/1986 |
| JP | 61-264262 | A | 11/1986 |

(Continued)

OTHER PUBLICATIONS

"A printout retrieved from https://en.wikipedia.org/wiki/Vitamin_C on Dec. 5, 2017.", Wikipedia, [Online] Retrieved from the Internet: <URL: http://web.archive.org/web/20171111231338/https://en.wikipedia.org/wiki/Vitamin_C>, (Nov. 11, 2017), 34 pgs.

(Continued)

*Primary Examiner* — Alan D Diamond
*Assistant Examiner* — Jerry D Johnson
(74) *Attorney, Agent, or Firm* — Schwegman Lundberg & Woessner, P.A.

(57) ABSTRACT

Methods, reagents, kits and systems are disclosed for determining an analyte in a sample suspected of containing the analyte where all reagents are soluble in aqueous solution. One assay method includes treating a sample suspected of containing the analyte under conditions such that if the analyte is present, an activator is brought into reactive configuration with a chemiluminescent compound to activates it. The sample is also treated with an agent to reduce signal not related to analyte. Finally, the sample is treated with a trigger solution thereby producing light from the activated chemiluminescent compound. No reagents are associated with a surface or other solid phase.

9 Claims, No Drawings

(56) References Cited

FOREIGN PATENT DOCUMENTS

| | | | |
|---|---|---|---|
| JP | 01-150856 | A | 6/1989 |
| JP | H01150856 | A | 6/1989 |
| JP | 07-311197 | | 11/1995 |
| JP | H07311197 | A | 11/1995 |
| JP | 2723128 | | 11/1997 |
| JP | 2002524102 | A | 8/2002 |
| JP | 5844643 | B2 | 11/2015 |
| JP | 5844643 | | 1/2016 |
| JP | 6037522 | B2 | 11/2016 |
| JP | 6037522 | | 12/2016 |
| MX | 2011009019 | | 9/2011 |
| MX | 2011009019 | A | 9/2011 |
| WO | WO 91/19979 | | 12/1991 |
| WO | WO 99/03849 | | 1/1999 |
| WO | WO-9903849 | A1 | 1/1999 |
| WO | WO-0015618 | A1 | 3/2000 |
| WO | WO-20061 30551 | A2 | 12/2006 |
| WO | WO-2007058654 | A1 | 5/2007 |
| WO | WO 2007/134098 | A1 | 11/2007 |
| WO | WO-2007133988 | A1 | 11/2007 |
| WO | 2010/099486 | | 9/2010 |
| WO | WO-2010099486 | A1 | 9/2010 |

OTHER PUBLICATIONS

Bhattacharyya, Sibaprasad, et al., "Synthesis and Evaluation of Near-Infrared (NIR) Dye-Herceptin Conjugates as Photoacoustic Computed Tomography (PCT) Probes for HER2 Expression in Breast Cancer", Bioconjug. Chern., vol. 19, No. 6, (Jun. 2008), 1186-1193.

Fleming, James E, et al., "Bicyclic ring formation is not necessary for the (auto) oxidation of ascorbic acid", Biochem Biophys Res Commun, vol. 115, No. 2, (1983), 531-535.

Panchuk-Voloshina, Nataliya, et al., "Alexa dyes, a series of new fluorescent dyes that yield exceptionally bright, photostable conjugates.", J Histochem Cytochem., 47(9), (1999), 1179-88.

Tyrrell, Eadaoin, et al., "Development of a micro-fluidic manifold for copper monitoring utilising chemiluminescence detection", Lab on a Chip, 4(4), The Royal Society of Chemistry, (2004), 384-390.

Bagley, Mark C, et al., "Total Synthesis of the Thiopeptide Promothiocin A", J. Am. Chem. Soc., vol. 122, No. 14, (2000), 3301-3313.

Castillo, Federico J, et al., "Peroxidase assay in plants: Interference by ascorbic acid and endogenous inhibitors in Sedum and Pelargonium enzyme extracts", Plant Growth Regulation, vol. 2, (1984), 69-75.

Ci, Yx, "The Use of Mn-TPPS4 Mimetic Peroxidase in a DNA Hybridization Assay", Microchemical journal, 52(3), (1995), 257-262.

Hermanson, "Tags and Probes", Biconjugate Techniques, Academic Press, (Jan. 22, 1996), 297-362.

Horton, JK, et al., "Enzyme immunoassays for the estimation of adenosine 3',5' cyclic monophosphate and guanosine 3',5' cyclic monophosphate in biological fluids", Journal of Immunological Methods, vol. 155, Issue 1, (Oct. 19, 1992), 31-40.

Ji, Tae H, "Bifunctional Reagents", Methods in Enzymology, vol. 91, (1983), 580-609.

Kricka, Larry J, "Clinical and biochemical applications of luciferases and luciferins", Analytical Biochemistry, vol. 175, Issue 1, (1988), 14-21.

Kricka, Larry J, "Ligand-Binder Assays Labels and Analytical Strategies", Marcel Dekker, Inc., New York and Basel, (1985), 18-20.

Martinello, Flavia, et al., "Mechanism of ascorbic acid interference in biochemical tests that use peroxide and peroxidase to generate chromophore", Clinica Chimica Acta, vol. 373, Issues 1-2, (Nov. 2006), 108-116.

Tanaka, et al., "Preparation and physicochemical analysis of 5-methl-3, 4-dihydroxytetrone produced by oxidative degradation of dehydro-L-ascorbic acid,", Fukuoka Science Reports, vol. 34, No. 2, (2004), 15-21.

Velijovic-Jovanovic, Sonja, et al., "Are leaf hydrogen peroxide concentrations commonly overestimated? The potential influence of artefactual interference by tissue phenolics and ascorbate", Plant Physiology and Biochemistry, vol. 40, (2002), 501-507.

White, Emil H, et al., "The Chemi- and Bioluminescence of Firefly Lucierin: An Efficient Chemical Production of Electronically Excited States", Bioorganic Chemistry, vol. 1, (1971), 92-122.

Osman et al., "Comparative studies of the chemiluminescent horseradish peroxidase-catalysed peroxidation of acridan (GZ-11) and luminol reactions: effect of pH and scavengers of reactive oxygen species on the light intensity of these systems," Luminescence, 2000, vol. 15, No. 3, pp. 189-197.*

A printout retrieved from https://en.wikipedia.org/wiki/Vitamin_C on Dec. 5, 2017.*

Castillo, F. et al. "Peroxidase assay in plants: Interference by ascorbic acid and endogenous inhibitors in Sedum and Pelargonium enzyme extracts," Plant Growth Regulation. vol. 2, pp. 69-75 (1984).

Japanese Office Action dated Jul. 11, 2014, for related Japanese patent application No. 2011-552201.

Japanese Office Action dated Jul. 11, 2014 for related Japanese patent application No. 2011-552201. (English Translation).

JK Horton et al., J Immunological Methods, 1992, 155 31-40.

Kricka, L., "Clinical and Biochemical Applications of Lucierases and Luciferins," Analytical Biochemistry, vol. 175, pp. 14-21 (1988).

T H Ji, "Bifunctional Reagents," Methods in Enzymology, 91, 580-609 (1983).

Y.-X. Ci, et al., "The Use of Mn-TPPS4 Mimetic Peroxidase in a DNA Hybridization Assay", Microchemical Journal., 52:257-62 (1995).

Office Action dated May 30, 2016 in corresponding Japanese Patent Application No. 2015-133808, and English language translation thereof, 7 pages total.

International Search Report of PCT/US2010/025657, dated Jun. 17, 2010, 3 pages total.

* cited by examiner

SOLUTION PHASE HOMOGENEOUS ASSAYS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a Continuation of U.S. patent application Ser. No. 12/714,346, filed Feb. 26, 2010, now U.S. Pat. No. 9,029,092, which claims the benefit of U.S. Provisional Application No. 61/156,473, filed Feb. 27, 2009, and claims the benefit of U.S. Provisional Application No. 61/300,318, filed Feb. 1, 2010, the contents of each of which are incorporated herein by reference in their entirety.

BACKGROUND

Specific binding assays are test methods for detecting the presence or amount of a substance and are based on the specific recognition and binding together of specific binding partners. Immunoassays are an example of a specific binding assay in which an antibody binds to a particular protein or compound. In this example an antibody is a member of a specific binding pair member. Nucleic acid binding assays are another type in which complementary nucleic acid strands are the specific binding pair. Specific binding assays constitute a broad and growing field of technology that enable the accurate detection of disease states, infectious organisms and drugs of abuse. Much work has been devoted over the past few decades to devise assays and assay methodology having the required sensitivity, dynamic range, robustness, broad applicability and suitability to automation. These methods can be grouped broadly into two categories.

Homogeneous methods utilize an analyte-specific binding reaction to modulate or create a detectable signal without requiring a separation step between analyte-specific and analyte non-specific reactants. Heterogeneous formats rely on physical separation of analyte-bound and free (not bound to analyte) detectably labeled specific binding partners. Separation typically requires that critical reactants be immobilized onto some type of solid substrate so that some type of physical process can be employed, e.g. filtration, settling, agglomeration or magnetic separation, and typically also require wash steps to remove the free detectably labeled specific binding partners.

Assay methods relying on producing a chemiluminescent signal and relating it to the amount of an analyte have experienced increasing use. Such methods can be performed with relatively simple instruments yet display good analytical characteristics. In particular, methods employing an enzyme-labeled specific binding partner for the analyte and a chemiluminescent enzyme substrate for detection have found widespread use. Common label enzymes include alkaline phosphatase and horseradish peroxidase.

U.S. Pat. No. 6,911,305 discloses a method of detecting polynucleotide analytes bound to a sensitizer or sensitizer-labeled probe on a first film. The film is contacted with a second film bearing an immobilized chemiluminescent precursor. Exciting the sensitizer in the sandwiched films produces singlet oxygen which reacts with the chemiluminescent precursor to produce a triggerable chemiluminescent compound on the second film. The triggerable chemiluminescent compound is reacted with a reagent to generate chemiluminescence on the second film for detecting the analyte. These methods do not rely on the specific binding reaction for bringing the reactants into contact; rather the second film serves as a reagent delivery device.

U.S. Pat. No. 6,406,913 discloses assay methods comprising treating a medium suspected of containing an analyte under conditions such that the analyte causes a photosensitizer and a chemiluminescent compound to come into close proximity. The photosensitizer generates singlet oxygen when irradiated with a light source; the singlet oxygen diffuses through a solution to and activates the chemiluminescent compound when it is in close proximity. The activated chemiluminescent compound subsequently produces light. The amount of light produced is related to the amount of analyte in the medium. In one embodiment, at least one of the photosensitizer or the chemiluminescent compound is associated with a suspendible particle, and a specific binding pair member is bound thereto U.S. patent application publications US20070264664 and US20070264665 disclose assay methodology for performing specific binding pair assays involving reaction of immobilized chemiluminescent compounds with activator compounds brought into a reactive configuration by virtue of the specific binding reaction. No separation or removal of the excess unbound chemiluminescent compound or activator is required. These assay formats provide superior operational convenience and flexibility in automation compared to prior art assay techniques. Despite these advantages, additional improvements in assay design and performance remain a goal of assay developers. The assay methods of the present disclosure address these needs by providing simple assay methods of improved sensitivity.

SUMMARY

Methods, reagents, kits and systems are disclosed for determining an analyte in a sample suspected of containing the analyte where all reagents are soluble in aqueous solution. One assay method includes treating a sample suspected of containing the analyte under conditions such that if the analyte is present, an activator is brought into reactive configuration with a chemiluminescent compound to activates it. The sample is also treated with an agent to reduce signal not related to analyte. Finally, the sample is treated with a trigger solution thereby producing light from the activated chemiluminescent compound. No reagents are associated with a surface or other solid phase.

DESCRIPTION

Definitions

Alkyl—A branched, straight chain or cyclic hydrocarbon group containing from 1-20 carbons which can be substituted with 1 or more substituents other than H. Lower alkyl as used herein refers to those alkyl groups containing up to 8 carbons.

Analyte—A substance in a sample to be detected in an assay. One or more substances having a specific binding affinity to the analyte will be used to detect the analyte. The analyte can be a protein, a peptide, an antibody, or a hapten to which an antibody that binds it can be made. The analyte can be a nucleic acid or oligonucleotide which is bound by a complementary nucleic acid or oligonucleotide. The analyte can be any other substance which forms a member of a specific binding pair. Other exemplary types of analytes include drugs such as steroids, hormones, proteins, glycoproteins, mucoproteins, nucleoproteins, phosphoproteins, drugs of abuse, vitamins, antibacterials, antifungals, antivirals, purines, antineoplastic agents, amphetamines, azepine compounds, nucleotides, and prostaglandins, as well as metabolites of any of these drugs, pesticides and metabolites of pesticides, and receptors. Analyte also includes cells, viruses, bacteria and fungi.

Activator: a compound, also may be referred to as a label, that effects the activation of the chemiluminescent compound so that, in the presence of a trigger, chemiluminescence is produced.

Activator-labeled sbm or activator-specific binding member conjugate—a reactant in the assay mix that includes at least the following in a connected configuration: a) a specific binding member for an analyte and b) an activator compound or label that effects activation of a chemiluminescent compound.

Antibody—includes the full immunoglobulin as well as native and engineered fragments.

Aralkyl—An alkyl group substituted with an aryl group. Examples include benzyl, benzyhydryl, trityl, and phenylethyl.

Aryl—An aromatic ring-containing group containing 1 to 5 carbocyclic aromatic rings, which can be substituted with 1 or more substituents other than H.

Biological material—includes, for example. whole blood, anticoagulated whole blood, plasma, serum, tissue, animal and plant cells, cellular content, viruses, and fungi.

Chemiluminescent compound—A compound, which also may be referred to as a label, which undergoes a reaction so as to cause the emission of light, for example by being converted into another compound formed in an electronically excited state. The excited state may be either a singlet or triplet excited state. The excited state may directly emit light upon relaxation to the ground state or may transfer excitation energy to an emissive energy acceptor, thereby returning to the ground state. The energy acceptor is raised to an excited state in the process and emits light.

Chemiluminescent-labeled immobile sbm: a reactant in the assay mix that includes at least the following in a connected configuration: a) a specific binding member for an analyte, b) an chemiluminescent compound or label, and c) a solid phase.

Connected—As used herein indicates that two or more chemical species or support materials are chemically linked, e.g. by one or more covalent bonds, or are passively attached, e.g. by adsorption, ionic attraction, or a specific binding process such as affinity binding. When such species or materials are connected with each other, more than one type of connection can be involved Dose Response—Signal, such as chemiluminescent output from an assay reaction that is related to the amount of the analyte being determined in the sample.

Heteroalkyl—An alkyl group in which at least one of the ring or non-terminal chain carbon atoms is replaced with a heteroatom selected from N, O, or S.

Heteroaryl—An aryl group in which one to three of the ring carbon atoms is replaced with a heteroatom selected from N, O, or S. Exemplary groups include pyridyl, pyrrolyl, thienyl, furyl, quinolyl and acridnyl groups.

Sample—A mixture containing or suspected of containing an analyte to be measured in an assay. Analytes include for example proteins, peptides, nucleic acids, hormones, antibodies, drugs, and steroids Typical samples which can be used in the methods of the disclosure include bodily fluids such as blood, which can be anticoagulated blood as is commonly found in collected blood specimens, plasma, serum, urine, semen, saliva, cell cultures, tissue extracts and the like. Other types of samples include solvents, seawater, industrial water samples, food samples and environmental samples such as soil or water, plant materials, eukaryotes, bacteria, plasmids, viruses, fungi, and cells originated from prokaryotes.

sbp—A specific binding pair member or specific binding partner is a molecule, including biological molecules, having a specific binding affinity for another substance (e.g., analyte. Two specific binding partners for an analyte, preferably with different binding sites on the analyte, are referred to as a specific binding pair.

SSIA, (Selective Signal Inhibiting Agent)—A compound provided in an assay reaction mixture of the present disclosure such that non-specific signal or background signal is reduced in a greater amount than the analyte-specific signal generated from the chemiluminescent production reaction of the assay reaction mixture.

Solid support—a material at least 1 micron in size having a surface upon which assay components are immobilized. Materials can be in the form of particles, microparticles, nanoparticles, metal colloids, fibers, sheets, beads, membranes, filters and other supports such as test tubes, microwells, chips, glass slides, and microarrays.

Soluble, solubility, solubilize—The ability or tendency of one substance to blend uniformly with another. In the present disclosure, solubility and related terms generally refer to the property of a solid in a liquid, for example SSIA in an aqueous buffer. Solids are soluble to the extent they lose their crystalline form and become molecularly or ionically dissolved or dispersed in the solvent (e.g. liquid) to form a true solution. In contrast: two-phase systems where one phase consists of small particles (including microparticles or colloidal sized particles) distributed throughout a bulk substance, whether stabilized to deter precipitation or unstabilized.

Substituted—Refers to the replacement of at least one hydrogen atom on a group by a non-hydrogen group. It should be noted that in references to substituted groups it is intended that multiple points of substitution can be present unless clearly indicated otherwise.

Reaction Vessel—A vessel or apparatus for containing the sample and other components of an assay according to the present invention. Included are, for example, test tubes of various sizes and shapes, and microwell plates.

DISCLOSURE

The present disclosure provides homogeneous assay methods, in particular homogeneous assay methods using chemiluminescent detection of analytes after binding of a chemiluminescent-labeled specific binding partner and an activator-labeled specific binding partner conjugate and the analyte. Homogeneous assays and methods are performed without separating free specific binding partners from specific binding partners bound in complexes.

The present disclosure provides rapid and simple homogeneous assays for detecting the presence, location, or amount of substances by means of specific binding pair reactions. The assays require the use of a chemiluminescent compound connected with a first specific binding partner ("chemiluminescent-labeled sbp"), an activator compound conjugated to a second specific binding partner ("activator-labeled sbp"), a selective signal inhibiting agent ("SSIA"), an enhancer, in a solution phase and a trigger solution.

In contrast to other homogenous assays, a basic embodiment of this disclosure, all reactants, including the activator-labeled sbp and the chemiluminescent-labeled sbp are soluble in aqueous solution. In fact, the assays of the present disclosure do not require or utilize a solid phase. The present assay methods also differ from other homogeneous assay methods by not requiring specialized constructs, namely labeled specific binding pair members that are designed with a detectable component that is inactivated or only able to generate the particular detectable signal after it is bound in a complex with another component. In contrast to the assay system of the present disclosure, other homogenous assay systems are complex, difficult, or expensive to prepare because they require such specialized components. The present assays afford a simpler, more flexible approach to assay design and development and permit more ready application to a wide variety of analytes. The present assay methods differ from conventional heterogeneous or separation-based assay methods by not utilizing a separation step or process to differentiate free specific binding partners from specific binding partners bound in complexes. By use of the present assay methods which avoid separations, conduct of assays is simplified, assay times can be reduced and automation is facilitated.

In assay methods of the present disclosure a chemiluminescent-labeled sbp an activator-labeled sbp, and selective signal inhibiting agent ("SSIA"), are brought together in aqueous solution with a sample. In one embodiment when the analyte recognized by the sbp members is present in the sample, chemiluminescent-labeled sbp and activator-labeled sbp each bind to different areas of the analyte. The specific signal related to analyte is generated and detection begins upon addition of a trigger solution. In another embodiment a chemiluminescent-labeled analog of the analyte is provided for use in a competitive assay format. Analyte and chemiluminescent-labeled analog competitively bind to activator-labeled sbp. Complexes of chemiluminescent-labeled analog and activator-labeled sbp can be pre-formed and the analyte added to displace the labeled analog in one embodiment of a competitive binding assay. In another embodiment chemiluminescent-labeled analog, the analyte, and activator-labeled sbp can be mixed together without pre-forming binding complexes. The specific signal related to analyte is generated and detection begins upon addition of a trigger solution. Signal is inversely related to analyte concentration in this assay format.

As a result of the specific binding partners binding to the analyte, an activator is brought into operable proximity to a chemiluminescent compound so that it is effective to activate a reaction generating chemiluminescence upon addition of a trigger solution. Reaction of the activator with the chemiluminescent compound activates or alters the chemiluminescent compound such that treatment with a trigger solution results in a further reaction resulting in the generation of light. By operable proximity is meant that the chemiluminescent compound and activator are close enough, including and up to physical contact, that they can react. Excess amounts of activator-labeled specific binding partner and/or chemiluminescent-labeled specific binding partner may be provided to the system in relation to the amount needed to determine analyte concentration. The excess unbound activator-labeled sbp and/or unbound chemiluminescent conjugate is not removed prior to addition of trigger solution and detection since their presence and the lack of solid phase in the assay system does not prevent the chemiluminescent detection signal from being accurately correlated with the amount of the analyte. Since the unbound, labeled specific binding partners are capable of undergoing the same chemiluminescent detection reaction and the reactants are not connected to a solid phase, no useful correlation, or at best, a very limited correlation of signal with analyte would be expected. This feature would, according to conventional wisdom, ordinarily cause assays to fail.

Surprisingly, this problem has been overcome by the use of a selective signal inhibiting agent in the present methods. In the present methods, the reactants being in solution with no connection to solid phase and presence of excess activator and/or excess chemiluminescent compound, that is not removed, does not defeat the ability to perform sensitive, specific, analyte-concentration dependent binding assays. This finding was not expected or predictable. In particular when the activator is a catalyst such as an enzyme that ordinarily would induce hundreds to thousands of reactive transformations each second when the molecule on which it reacts is free in solution, it would not have been expected that the bound activator could be usefully discriminated from the free activator reaction in order to produce a dose responsive signal over a wide range of analyte concentrations. Yet the inventors have discovered that excellent discrimination results from the addition of certain SSIA compounds. By use of the SSIA, the ratio of signal produced by reaction between chemiluminescent label and activator label, both in a reactive configuration by way of a complex of labeled specific binding pair members with an analyte, to signal from the labels present but not in such a complex is dramatically improved.

The function of the SSIA in improving assay sensitivity is understood in reference to Scheme 1. Multiple different combinations of free (e.g., not bound to analyte) and complexed (e.g., analyte bound) chemiluminescent-labeled sbp ("CLSBP") and activator-labeled specific binding pair ("ALSBP") may possibly contribute to the observed chemiluminescent signal when trigger solution is added. Four proposed reaction schemes are listed below:

1 Bound-ALSBP+Bound-CLSBP→Specific Signal
2 Bound-ALSBP+Free-CLSBP→Non-specific Signal
3 Free-ALSBP+Bound-CLSBP→Non-specific Signal
4 Free-ALSBP+Free-CLSBP→Non-specific Signal As shown in the list above, four different types of chemiluminescer-activator pairs can react in the reaction mix; yet only the first type produces a signal that is relatable to the amount of analyte in an assay. The SSIA achieves its surprising function by selectively inhibiting or depressing the amount of signal from reactions 2-4 in relation to that from reaction 1. In some embodiments this may occur by reducing all four reactions but reducing signal from 2-4 proportionately much more.

In embodiments of the present invention, there are provided methods of assaying analytes of interest in a sample by means of specific binding reactions involving the analyte and specific binding partners (sbp) for the analyte wherein one specific binding partner is labeled with an activator compound which may be a catalyst such as an enzyme, particularly a peroxidase enzyme. Another specific binding partner for the analyte is labeled with a chemiluminescent compound. Binding of the labeled sbp's and the analyte form labeled complexes. The chemiluminescent compound undergoes a chemiluminescent reaction induced by the activator when a trigger solution is added. The chemiluminescence that results is related to the amount of the analyte in the sample. The specific binding pair reactions and the chemiluminescent reaction are performed with all components dissolved in a solution, typically an aqueous solution. Significantly, the labeled specific binding partners are provided in an excess amount in relation to the amount of the analyte in the sample so that not all of the labeled sbp form complexes with the analyte. The excess labeled sbp's are not removed from the reaction solution even though they are capable of participating in the chemiluminescent reaction. The reactivity of labeled sbp's that are not in complexes and are not removed ordinarily prevents such homogeneous assays from being performed since unacceptably high signals are generated that are not due to the presence of complex formation mediated by the analyte. In many cases so much "background" signal is generated that no useful dose-response relationship can be elicited. In order to be able to perform a homogeneous nonseparation assay when all of the reaction components necessary for chemiluminescent signal generation are present both in the binding complex and in free or unbound form, some means must be provided to discriminate bound and unbound labeled sbp's, other than a physical separation. The present invention provides a long-sought solution to this problem and provides assay methods wherein all components are in solution, no separation is performed. Unlike known homogeneous assay methods, the present methods do not require or use specially designed labeled binding partners that are incapable of undergoing the signal-producing reaction unless they are brought into a binding complex.

In assay methods embodied by the invention, the necessary discrimination of labeled sbp members bound in a complex with the analyte from free, unbound labeled sbp members is achieved by providing a Selective Signal Inhibiting Agent (SSIA) to the reaction solution. Addition of an effective amount of the SSIA to the reaction solution causes the signal from the bound labeled sbp members (Signal) to exceed background signal, including any signal contribution from unbound labeled sbp members by a significantly greater degree than occurs in its absence. When this improvement of the relationship of Signal to Background is achieved, the usefulness of the assays increases, including higher levels of detection sensitivity.

In one embodiment there are provided assay methods, in particular binding assay methods, in which a chemiluminescent-labeled sbp and an activator-labeled sbp are brought into operable proximity via at least one specific binding reaction due to the presence of an analyte, wherein the bound activator-labeled sbp activates a reaction generating chemiluminescence upon addition of a trigger solution for detecting the presence, location or amount of the analyte.

In one embodiment the present methods also differ from conventional test methods in not removing the unbound activator-labeled sbp present in great excess to the amount specifically connected with the analyte. No washing or separation of excess unbound activator activator-labeled sbp is required. In another embodiment the present methods also do not remove the unbound chemiluminescent conjugate present in excess to the amount specifically connected with the analyte. No washing or separation of excess unbound chemiluminescent conjugate is required.

The assay components, namely: sample containing analyte, activator-labeled sbp, chemiluminescent-labeled sbp, selective signal inhibiting agent and trigger solution can be added sequentially to a test vessel, without washing or separations, and the luminescence read. The assay components, other than the trigger solution which is added last, may be added in any order or combination to the test vessel. In one embodiment, sample and activator-labeled sbp can be pre-mixed and added to the test vessel containing the chemiluminescent-labeled sbp before introducing the trigger solution.

Conventional assays using chemiluminescent substrates and enzyme labeled conjugates provide the chemiluminescent substrate in great excess to the amount of label enzyme. Frequently, the molar ratio of substrate/enzyme can exceed nine powers of ten, i.e., a billion-fold excess. It is believed to be necessary in conventional assays to supply such an enormous excess of chemiluminescent compound in order to ensure an adequate supply of substrate for continuous enzymatic turnover and that this process guarantees adequate detection sensitivity in assay methods. Applicants have found that it is possible to devise highly sensitive assay methods that reduce the ratio of chemiluminescent compound to activator by several orders of magnitude. In this regard these methods described herein differ fundamentally from known enzyme-linked assay methods.

Eliminating washing and separation steps as described above and as demonstrated in exemplary assays described below affords opportunities to simplify the design of assay protocols. The reduced number of operational steps decreases assay time, inter-assay variability from incomplete washing, and cost. At the same time it enhances the ability to automate and miniaturize assay performance with all of the inherent advantages attendant on automation and miniaturization.

Assays performed according to the present methods includes providing a specific binding partner ("sbp") for specifically binding or capturing an analyte of interest. The specific binding partner is capable to either directly or indirectly bind an analyte to be detected. The specific binding partner is further provided with chemiluminescent labeling compound attached either directly or indirectly thereto. The chemiluminescent label may be provided in a number of different ways as described in more detail below. In each variant the chemiluminescent label is stably or irreversibly connected, either directly or indirectly with the specific binding partner in a way that maintains the aqueous solubility of the "chemiluminescent-labeled sbp". By "irreversibly" it is intended that the chemiluminescent label is not substantially removed from the chemiluminescent-labeled sbp under the conditions of use in the intended assay. Passive or noncovalent attachment is also contemplated provided that the label is stably attached and retained on the chemiluminescent-labeled sbp under the conditions of use.

The assay further includes providing an activator-labeled sbp having the analyte and the chemiluminescent-labeled sbp connected specific binding partner for the analyte and permitting the components to form specific binding complexes. The sample, chemiluminescent-labeled sbp, and activator activator-labeled sbp can be added separately in any order or in any combination sequentially or simultaneously, or can be pre-mixed and added as a combination. Typically a period of time will be required to allow binding of analyte to the labeled sbp members. This can be accomplished in some embodiments where the binding components are added sequentially by an optional delay time to allow binding reactions to occur.

After the binding complex is formed, a trigger solution is added to produce the chemiluminescence for detecting the analyte and the chemiluminescence is detected. Typically either peak light intensity level, or light intensity is integrated for a fixed time interval, or total integrated light intensity is measured. The quantity of light produced is related to the amount of the analyte present in the sample contained in a reaction vessel. The quantity of light may be used to determine the numerical amount of the analyte by constructing a calibration curve according to generally known methods. When light emission ensues rapidly upon addition of trigger solution it is desirable to either mechanically time the onset of measurement to the addition by means of a suitable injector or to perform the addition with the reaction vessel already exposed to the detector. Optimum quantities of reactants, volumes, dilutions, incubation times for specific binding pair reactions, concentration of reactants, etc., can be readily determined by routine experimentation, by reference to standard treatises on methods of performing specific binding assays and using as a guide the specific examples described in detail below.

The concentration or amount of the sbp members used in the present methods and assays will depend on such factors as analyte concentration, the desired speed of binding/assay time, cost and availability of conjugates, the degree of nonspecific binding of sbp members. Usually, the sbp members will be present in at least equal to the minimum anticipated analyte concentration, more usually at least the highest analyte concentration expected or greater, and for noncompetitive assays the concentrations may be from 10 time to $10^6$ times the highest analyte concentration. Usually the concentration of sbp members is less than $10^{-4}$ M, preferably less than $10^{-6}$ M, frequently between $10^{-11}$ and $10^{-7}$ M. The amount of activator or chemiluminescent compound connected with a sbp member will usually be at least one molecule per sbp member and may be as high as $10^2$, more. In many embodiments, the amount of activator or chemiluminescent compound connected with a sbp member is from 1 to 20 molecules. Examples and other ratios of activator to chemiluminescent compound are provided in the worked examples.

Chemiluminescent-Labeled SBP

The methods require the use of a chemiluminescent compound connected with a first specific binding partner ("chemiluminescent-labeled sbp"), In the assays and methods of the present disclosure, the chemiluminescent-labeled sbp is soluble in aqueous solution. In the assays and methods of the present disclosure, the chemiluminescent labeling compound is not immobilized to a solid surface, such as a particle, multiwell plate, or membrane, filter, test tube, dipstick, or pipet tip as is found in other affinity assays and methods.

The chemiluminescent-labeled sbp includes a chemiluminescent label compound and a member of a specific binding pair.

In some embodiments, a chemiluminescent-labeled sbp includes one or more chemiluminescent label compounds.

In some embodiments, a chemiluminescent-labeled sbp includes one or more copies of a member of a specific binding pair.

In some embodiments, a chemiluminescent label compound is directly connected to one or more copies of a member of a specific binding pair. In some other embodiments, one or more chemiluminescent label compounds are directly connected to one copy of a member of a specific binding pair. Direct connections, also referred to as direct-labeled; include covalent binding interactions, ionic binding interactions, and hydrophobic interactions. In one embodiment the chemiluminescent label is covalently linked to a specific binding partner for the analyte.

In some embodiments, a chemiluminescent label compound is indirectly connected to one or more copies of a member of a specific binding pair. In some other embodiments, one or more chemiluminescent label compounds are indirectly connected to one copy of a member of a specific binding pair. Indirect connections include one or more auxiliary substances in addition to a chemiluminescent label compound and a member of a specific binding pair.

The auxiliary substances are soluble in aqueous solution. Chemiluminescent-labeled sbp's which include one or more auxiliary substances are soluble in aqueous solution.

In various embodiments, auxiliary substances include soluble proteins (e.g. streptavidin, avidin, neutravidin, biotin, cationized BSA, fos, jun, keyhole limpet hemocyanin "KLH", immunoglobulins and fragments or portions thereof, whether native or engineered, soluble synthetic dendrimers (e.g., PAMAM), soluble synthetic polymers (e.g. polyacrylicacid "PAA"), soluble natural polymers (e.g., polysaccharides such as functionalized dextrans, amino-dextran, oligonucleotides, proteins, and any combinations thereof), liposomes, micelles, and vesicles, as well as combinations of one or more of soluble synthetic polymers, soluble natural polymers, and soluble proteins (e.g. IgG/Biotin/streptavidin/PAA). Other auxiliary substances that are soluble in aqueous solution and functionalizable for attachment to one or more chemiluminescent label compounds and/or sbp's are envisioned for use in the disclosed methods and assays.

In some embodiments the auxiliary substance to which the chemiluminescent label is covalently linked is a protein or peptide. Exemplary soluble proteins include albumins, avidins, streptavidin, avidin, alpha-helix proteins, fos, jun, keyhole limpet hemocyanin "KLH", immunoglobulins and fragments or portions thereof, whether native or engineered, and any combinations thereof. In one embodiment, the auxiliary substance is a universal antibody, such as IgG, wherein the chemiluminescent label is covalently linked to the universal antibody in a manner to maintain its binding affinity for an analyte specific capture antibody. In another chemiluminescent-labeled sbp embodiment, the chemiluminescent compound is connected to one or more sbp's via a biotin-streptavidin or biotin-neutravidin linkage. Chemiluminescent-labeled sbp's incorporating streptavidin-biotin, or equivalent linkages, may for example provide the specific binding partner as a biotin conjugate where the chemiluminescent compound is a streptavidin conjugate. Alternative arrangements of biotin-streptavidin and similar linkages are generally known. Alternatively chemiluminescent-labeled sbp's incorporating streptavidin-biotin, or equivalent linkages, may utilize the linkage for attachment of sbp or chemiluminescent compounds to one or more additional auxiliary substances.

In another embodiment an auxiliary substance to which the chemiluminescent label is covalently linked is a synthetic polymer. Assay formats using polymeric auxiliaries for connecting the chemiluminescent compound can connect to the specific binding partner for the analyte by covalent linkage, as biotin-avidin conjugate, or by indirect attachment through a universal capture component such as a species specific immunoglobulin. An In select embodiments, the chemiluminescent-labeled sbp includes an auxiliary substance selected from polysaccharides or soluble self-assembling proteins. In some embodiments, chemiluminescent-labeled sbp includes a polysaccharide such as amino-dextran or carboxyl-dextran. In some such embodiments, a polysaccharide, such as amino-dextran or carboxyl-dextran, has an average molecular weight in the range of 10 kDa to 500 kDa, and in other embodiments, has an average molecular weight in the range of 25-150 kDa. In a further embodiment, a chemiluminescent-labeled sbp includes a polysaccharide, such as amino-dextran or carboxyl-dextran having an average molecular weight in the range of 50-100 kDa. In a yet further embodiment a chemiluminescent-labeled sbp includes a polysaccharide, such as amino-dextran or carboxyl-dextran having an average molecular weight of 70 kDa.

In many embodiments, the average diameter of the chemiluminescent-labeled sbp is in the inclusive range of 5 nM to 800 nM. In select embodiments, incorporating soluble proteins, or other soluble natural plymers or soluble synthetic polymers, or combinations thereof, the average diameter of the chemiluminescent-labeled sbp is in the inclusive range of 200 nM to 600 nM, in some further embodiments, in the inclusive range of 300 nM to 500 nM.

Activator-Labeled SBP

The methods require the use of an activator compound connected with a first specific binding partner ("activator-labeled sbp"), In the assays and methods of the present disclosure, the activator-labeled sbp is soluble in aqueous solution. In the assays and methods of the present disclosure, the activator compound is not immobilized to a solid surface, such as a particle, multiwell plate, or membrane, filter, test tube, dipstick, or pipet tip as is found in other affinity assays and methods.

The activator-labeled sbp includes an activator label compound and a member of a specific binding pair.

In some embodiments, an activator-labeled sbp includes one or more activator compounds.

In some embodiments, an activator-labeled sbp includes one or more copies of a member of a specific binding pair.

In some embodiments, an activator compound is directly connected to one or more copies of a member of a specific binding pair. In some other embodiments, one or more activator label compounds are directly connected to one copy of a member of a specific binding pair. Direct connections, also referred to as direct labeled, include covalent binding interactions, ionic binding interactions, and hydrophobic interactions. In one embodiment the activator label is covalently linked to a specific binding partner for the analyte.

In some embodiments, an activator compound is indirectly connected to one or more copies of a member of a specific binding pair. In some other embodiments, one or more activator compounds are indirectly connected to one copy of a member of a specific binding pair. Indirect connections include auxiliary substances in addition to a chemiluminescent label compound and a member of a specific binding pair.

The auxiliary substances are generally soluble in aqueous solution. Activator-labeled sbp's which include one or more auxiliary substances are soluble in aqueous solution. In various embodiments, auxiliary substances include soluble proteins (e.g. streptavidin, avidin, neutravidin, biotin, cationized BSA, fos, jun, keyhole limpet hemocyanin "KLH", immunoglobulins and fragments or portions thereof, whether native or engineered, and any combinations thereof), soluble synthetic dendrimers (e.g., PAMAM), soluble synthetic polymers (e.g. polyacrylicacid "PAA"), soluble natural polymers (e.g., polysaccharides such as dextran, oligonucleotides, proteins, and any combinations thereof), liposomes, micelles, and vesicles, as well as combinations of one or more of soluble synthetic polymers, soluble natural polymers, and soluble proteins (e.g. IgG/Biotin/streptavidin/PAA). Other auxiliary substances that are soluble in aqueous solution and functionalizable for attachment to one or more activator label compounds and/or sbp's are envisioned for use in the disclosed methods and assays.

In some embodiments the auxiliary substance to which the activator label is covalently linked is a protein or peptide. Exemplary soluble proteins include albumins, avidins, streptavidin, avidin, alpha-helix proteins, fos, jun, keyhole limpet hemocyanin "KLH", immunoglobulins and fragments or portions thereof, whether native or engineered, and any combinations thereof. In one embodiment, the auxiliary substance is a universal antibody, such as IgG, wherein the activator label is covalently linked to the universal antibody in a manner to maintain its binding affinity for an analyte specific capture antibody. In another activator-labeled sbp embodiment, the activator compound is connected to one or more sbp's via a biotin-streptavidin linkage. Activator-labeled sbp's incorporating streptavidin-biotin, or equivalent linkages, may for example provide the specific binding partner as a biotin conjugate where the activator compound is a streptavidin conjugate. Alternative arrangements of biotin-streptavidin and similar linkages are generally known. Alternatively activator-labeled sbp's incorporating streptavidin-biotin, or equivalent linkages, may utilize the linkage for attachment of sbp or activator compounds to one or more additional auxiliary substances.

In another embodiment an auxiliary substance to which the activator label is covalently linked is a synthetic polymer. Assay formats using polymeric auxiliaries for connecting the activator compound can connect to the specific binding partner for the analyte by covalent linkage, non-covalent linkage, or by indirect attachment through a universal capture component such as a species specific immunoglobulin or biotin-avidin conjugation.

In select embodiments, the activator-labeled sbp includes an auxiliary substance selected from polysaccharides or soluble self-assembling proteins. In some embodiments, an activator-labeled sbp includes a polysaccharide such as amino-dextran or carboxyl-dextran. In some such embodiments, a polysaccharide, such as amino-dextran or carboxyl-dextran, has an average molecular weight in the range of 10 kDa to 500 kDa, or in other embodiments has an average molecular weight in the range of 25 kDa to 150 kDa. In a further embodiment, a chemiluminescent-labeled sbp includes a polysaccharide, such as amino-dextran or carboxyl-dextran having an average molecular weight in the range of 50-100 kDa. In a yet further embodiment a chemiluminescent-labeled sbp includes a polysaccharide, such as amino-dextran or carboxyl-dextran having an average molecular weight of 70 kDa.

In most embodiments, the average molecular weight of the activator-labeled sbp is in the inclusive range of 200 kDa to 3000 kDa. In some embodiments, the average molecular weight of the activator-labeled specific binding pair is typically 350 kDa to 1500 kDa.

Activator Labels

The activator compound forms part of an activator-labeled sbp, which may also be referred to as activator-specific binding partner conjugate. The activator-labeled sbp serves a dual function: 1) undergoing a specific binding reaction in proportion to the amount of the analyte in the assay through the specific binding partner portion, either directly or through an intermediary specific binding partner, and 2) activating the chemiluminescent compound through the activator portion. The activator portion of the activator-labeled sbp is a compound that effects the activation of the chemiluminescent compound so that, in the presence of the trigger solution, chemiluminescence is produced. Compounds capable of serving as the activator label include compounds with peroxidase-like activity including transition metal salts and complexes and enzymes, especially transition metal-containing enzymes, most especially peroxidase enzymes. Transition metals useful in activator compounds include those of groups 3-12 of the periodic table, especially iron, copper, cobalt, zinc, manganese, chromium, and vanadium.

The peroxidase enzymes which can undergo the chemiluminescent reaction include e.g., lactoperoxidase, microperoxidase, myeloperoxidase, haloperoxidase, vanadium bromoperoxidase, horseradish peroxidase, fungal peroxidases, lignin peroxidase, peroxidase from Arthromyces ramosus, Mn-dependent peroxidase produced in white rot fungi, and soybean peroxidase. Other peroxidase mimetic compounds are known which are not enzymes but possess peroxidase-like activity including iron complexes, such as heme, and Mn-TPPS4 (Y.-X. Ci, et al., Mikrochem. J., 52, 257-62 (1995)). These catalyze the chemiluminescent oxidation of substrates and are explicitly considered to be within the scope of the meaning of peroxidase as used herein.

In some embodiments, activator-labeled sbp can include conjugates or complexes of a peroxidase and a biological molecule in methods for producing chemiluminescence, the only proviso being that the conjugate display peroxidase or peroxidase-like activity. Biological molecules which can be conjugated to one or more molecules of a peroxidase include DNA, RNA, oligonucleotides, antibodies, antibody fragments, antibody-DNA chimeras, antigens, haptens, proteins, peptides, lectins, avidin, streptavidin and biotin. Complexes including or incorporating a peroxidase, such as liposomes, micelles, vesicles and polymers which are functionalized for attachment to biological molecules, can also be used in the methods of the present disclosure.

Selective Signal Inhibiting Agents (SSIA)

The selective signal inhibiting agents of the present invention are compounds that when included in an assay reaction mixture comprising free and/or analyte-bound chemiluminescent-labeled sbp, free and/or analyte-bound activator-labeled sbp, enhancer and a trigger solution, such that the resulting signal from the analyte-bound labeled sbp members exceed background signal by a significantly greater degree than occurs in the absence of the SSIA.

One or more selective signal inhibiting agents are present in reaction methods at concentration between 10-6 M and 10-1 M, frequently between 10-6 M and 10-2 M, often between 10-5 M and 10-3 M, sometimes between 10-5 M and 10-4M. In some embodiments, a selective signal inhibiting agent is present between 5×10-6 M and 5×10-4 M in reactions according to the present methods. In still further embodiments, a selective signal inhibiting agent is present between 5×10-5 M and 5×10-4 M in reactions according to the present methods.

The selective signal inhibiting agent can be supplied as a separate reagent or solution at a higher concentration than is intended in the reaction solution. In this embodiment a measured amount of the working solution is dosed into the reaction solution to achieve the desired reaction concentration. In another embodiment the selective signal inhibiting agent is combined into a solution containing one or more of the labeled sbp members. In another embodiment the selective signal inhibiting agent is provided as a component of the trigger solution.

The degree to which the selective signal inhibiting agent improves the signal:background ratio will vary depending on the identity of the compound and the concentration at which it is used, among other factors. The degree can be framed in terms of an improvement factor in which the signal:background ratio of an assay at a particular analyte concentration wherein the assay is performed with the selective signal inhibiting agent is compared to the signal: background ratio of an assay at the same analyte concentration without the selective signal inhibiting agent. An improvement factor >1 is a gauge of an improved assay and evidence of a beneficial effect of the selective signal inhibiting agent. In embodiments of the invention improvement factors of at least 2, such as at least 5 and including at least 10, or at least 50 are achieved. It will be seen in reference to the examples below, that improvement factors can vary within an assay as a function of the analyte concentration. For example, improvement factors may increase as analyte concentration increases. In another embodiment the variation in improvement factor across a concentration may result in a more linear calibration curve, i.e. plot of chemiluminescence intensity vs. analyte concentration.

The following table lists, without limitation, compounds capable of functioning effectively as selective signal inhibiting agents. Additional compounds, not explicitly recited, can be found using the teachings of the present disclosure, including by routine application of the assay and screening test methods described in the examples.

TABLE 1

| Selective Signal Inhibiting Agents | |
|---|---|
| Glutathione | Ascorbic acid or salts thereof |
| Uric Acid | L-Ascorbic acid 6-Palmitate |
| (±)-a-Tocopherol | 5,6-Isopropylidene-L-Ascorbic acid |
| (+)-y-Tocopherol | Butylated Hydroxytoluene (BHT) |
| 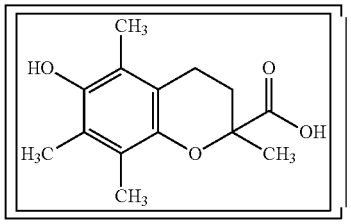 | 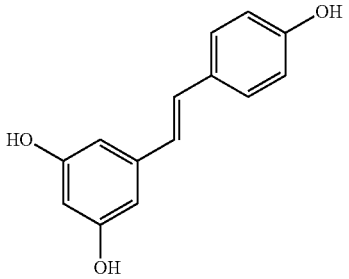 |

TABLE 1-continued

| Selective Signal Inhibiting Agents |
|---|
| 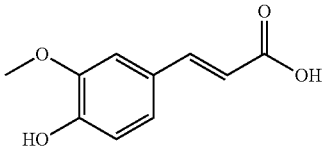 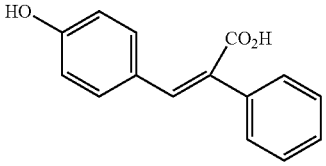 GW7.35 |
| 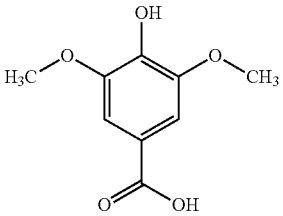 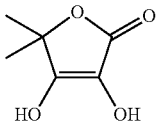 |
| 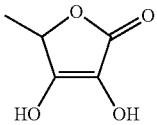 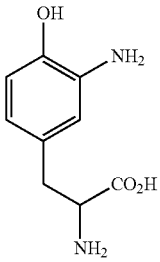 |
| 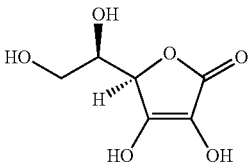 D-Isoascorbic acid 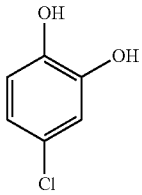 |
| 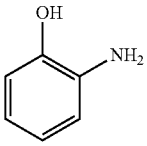 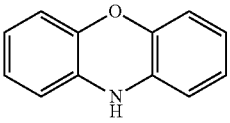 |
| 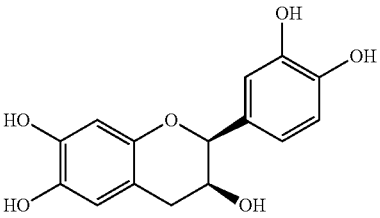 $Na_2SO_3$ $Et_2NOH$ |

In some other embodiments the selective signal inhibiting agent is selected from dialkylhydroxy amines.

In some embodiments the selective signal inhibiting agent is selected from aromatic compounds having at least two hydroxyl groups oriented in an ortho-, or para-relationship. Exemplary compounds are shown in Table 2.

TABLE 2

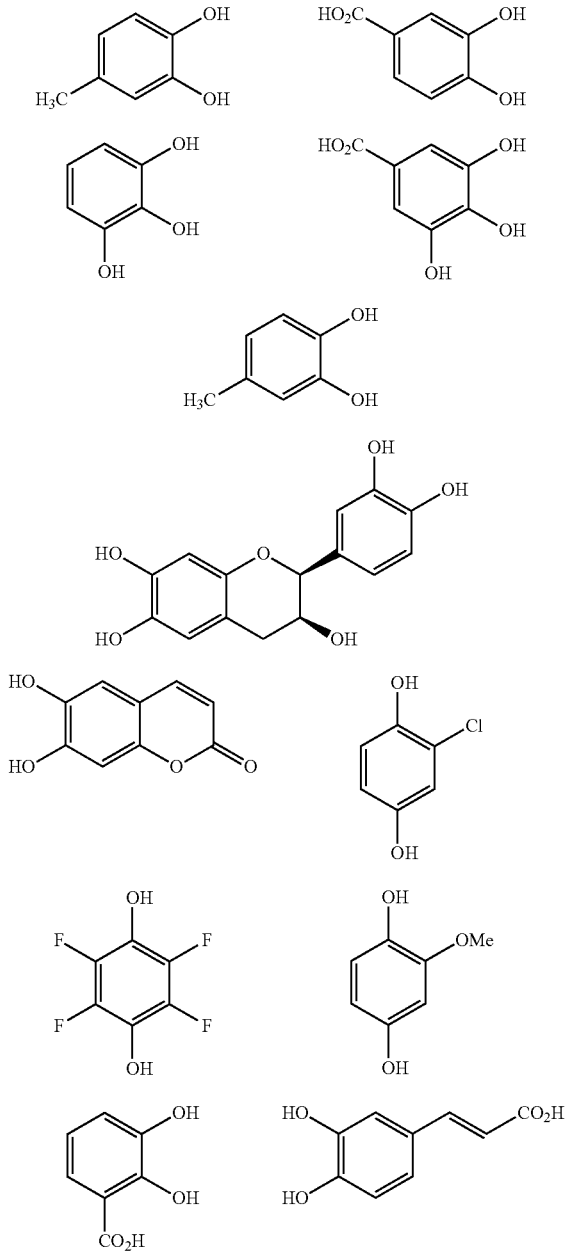

In some other embodiments the selective signal inhibiting agent is selected from aromatic compounds having at least a hydroxyl group and an amino group oriented in an ortho-, or para-relationship. Exemplary compounds are shown in Table 3.

TABLE 3

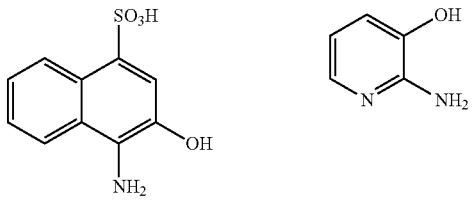

TABLE 3-continued

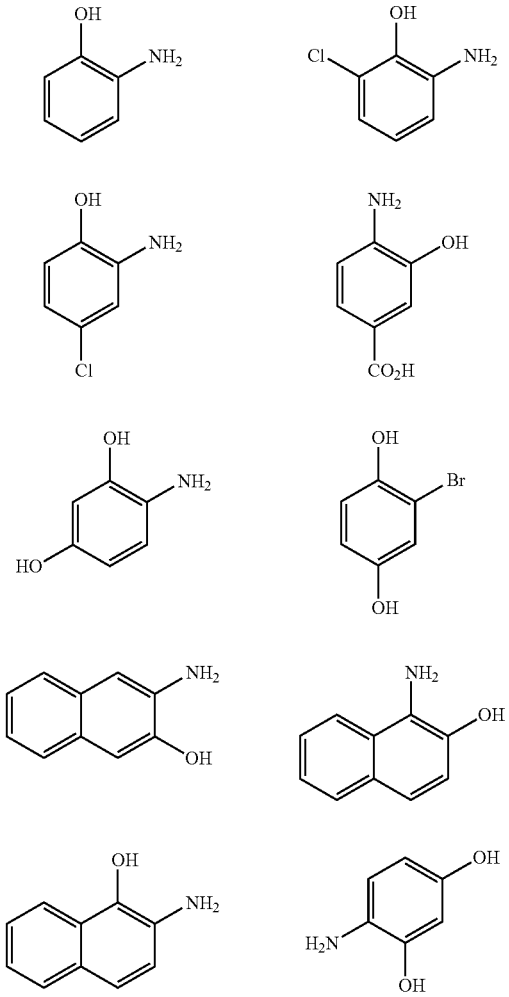

In yet other embodiments the selective signal inhibiting agent is selected from compounds having at least two hydroxyl groups substituted on a C—C double bond, also known as an enediol. Exemplary compounds are shown in Table 4.

TABLE 4

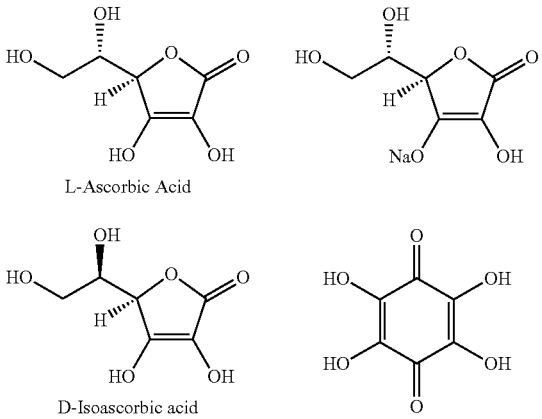

TABLE 4-continued

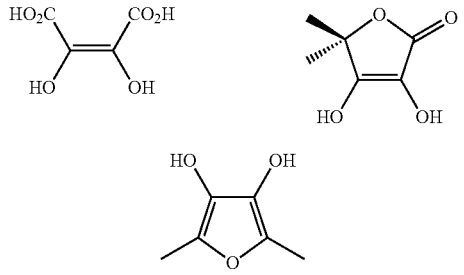

In one embodiment the selective signal inhibiting agent is selected from nitrogen heterocyclic compounds. Exemplary compounds are shown in Table 5.

TABLE 5

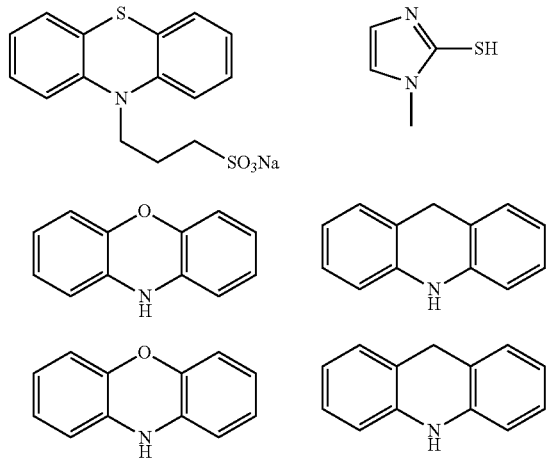

In one embodiment the selective signal inhibiting agent is supplied in masked form as a compound that is convertible into the active SSIA upon contact with peroxide. Suitable masked SSIA compounds are for example selected from hydroxyl- or amino-substituted arylboronic acid compounds. Exemplary compounds are shown in Table 6.

TABLE 6

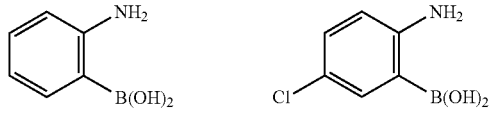

In one embodiment the selective signal inhibiting agent is selected from the compounds shown in Table 7.

TABLE 7

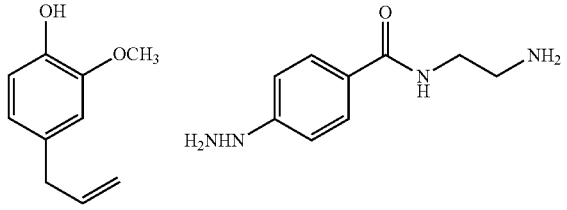

TABLE 7-continued

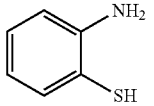

In various embodiments, one or more of the above selective signal inhibiting agents are used in combination in assay methods, assays or kits of the present disclosure. In some embodiments, selective signal inhibiting agents have solubility in aqueous solution at 10 times working solution concentration. Working solution is defined as a concentrated aqueous solution, such that a portion of the concentrated solution is added to the Reaction Mixture to give the final concentration required after the addition of trigger solution.

Suitable aqueous solutions for working solutions of selective signal inhibiting agent include one or more of the following additional components: salts, biological buffers, dimethyl sulfoxide (DMSO), dimethylformamide (DMF), alcohols, including ethanol, methanol, glycols, and detergents. In some embodiments, aqueous solutions include Tris buffered aqueous solutions, 25% Ethanol/75% Tris buffered aqueous solution, 25% Ethanol/75% aqueousTriton-X-100 (1%), 10% 0.1 N NaOH/90% Tris buffered aqueous solution. One example Tris buffered aqueous solution is composed of TRIS buffered saline, surfactant, <0.1% sodium azide, and 0.1% ProClin® 300 (Rohm and Haas)), referred to herein as Buffer II and is available commercially from Beckman Coulter, Inc., Brea Calif.

Trigger Solutions & Enhancers

The trigger solution provides a reactant necessary for generating the excited state compound necessary for chemiluminescence. The reactant may be one necessary for performing the chemiluminescent reaction by reacting directly with the chemiluminescent label. It may serve instead of or in addition to this function to facilitate the action of the activator compound. This will be the case, for example, when the activator is a peroxidase enzyme. In one embodiment the trigger solution comprises a peroxide compound. The peroxide component is any peroxide or alkyl hydroperoxide capable of reacting with the peroxidase. Exemplary peroxides include hydrogen peroxide, urea peroxide, and perborate salts. The concentration of peroxide used in the trigger solution can be varied within a range of values, typically from about $10^{-8}$ M to about 3 M, more commonly from about $10^{-3}$ M to about $10^{-1}$ M. In another embodiment the trigger solution comprises peroxide and an enhancer compound that promotes the catalytic turnover of an activator having peroxidase activity.

A representative embodiment uses a peroxidase conjugate as the activator, an acridan labeled specific binding partner of an analyte wherein the acridan label is provided by reacting the specific binding partner with an acridan labeling compound as described below, and a trigger solution comprising hydrogen peroxide. The peroxide reacts with the peroxidase, presumably to change the oxidation state of the iron in the active site of the enzyme to a different oxidation state. This altered state of the enzyme reacts with an enhancer molecule to promote the catalytic turnover of the enzyme. A reactive species formed from either the enhancer or the enzyme reacts with the acridan label maintained in proximity to the enzyme. The chemiluminescent reaction comprises a further reaction of an intermediate formed from the chemiluminescent compound with peroxide to produce the ultimate reaction product and light.

Incorporation of certain enhancer compounds into the trigger solution promotes the reactivity of the enzyme or reduces background signal or performs both functions. Included among these enhancers are phenolic compounds and aromatic amines known to enhance peroxidase reactions. Mixtures of a phenoxazine or phenothiazine compound with an indophenol or indoaniline compound as disclosed in U.S. Pat. No. 5,171,668 can be used as enhancer in the present invention. Substituted hydroxybenzoxazoles, 2-hydroxy-9-fluorenone, and compound I,

I

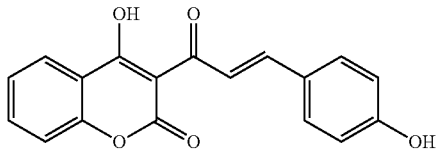

as disclosed in U.S. Pat. No. 5,206,149, can also be used as enhancer in the present invention. Substituted and unsubstituted arylboronic acid compounds and their ester and anhydride derivatives as disclosed in U.S. Pat. No. 5,512,451 are also considered to be within the scope of enhancers useful in the present disclosure. Exemplary phenolic enhancers include but are not limited to: p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol.

Mixtures of more than one enhancer from those classes mentioned above can also be employed.

Additional enhancers that are useful in the practice of the present invention are derivatives include hydroxybenzothiazole compounds and phenoxazine and phenothiazine compounds of formulas II and III below.

II and III

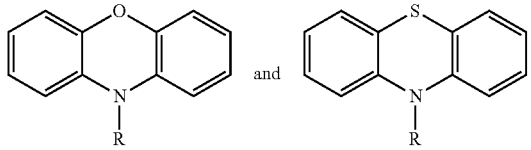

R groups substituted on the nitrogen atom of phenoxazine and phenothiazine enhancers include alkyl of 1-8 carbon atoms, and alkyl of 1-8 carbon atoms substituted with a sulfonate salt or carboxylate salt group. Exemplary enhancers include 3-(N-phenothiazinyl)-propanesulfonic acid salts, 3-(N-phenoxazinyl)propanesulfonic acid salts, 4-(N-phenoxazinyl)butanesulfonic acid salts, 5-(N-phenoxazinyl)-pentanoic acid salts and N-methylphenoxazine and related homologs. The concentration of enhancers used in the trigger solution can be varied within a range of values, typically from about $10^{-5}$ M to about $10^{-1}$ M, more commonly from about $10^{-4}$ M to about $10^{-2}$ M.

The detection reaction of the present disclosure is performed with a trigger solution which is typically in an aqueous buffer. Suitable buffers include any of the commonly used buffers capable of maintaining an environment permitting the chemiluminescent reaction to proceed. Typically the trigger solution will have a pH in the range of about 5 to about 10.5. Exemplary buffers include phosphate, borate, acetate, carbonate, tris(hydroxy-methylamino)methane[tris], glycine, tricine, 2-amino-2-methyl-1-propanol, diethanolamine MOPS, HEPES, MES and the like.

The trigger solution can also contain one or more detergents or polymeric surfactants to enhance the luminescence efficiency of the light-producing reaction or improve the signal/noise ratio of the assay. Nonionic surfactants useful in the practice of the present disclosure include by way of example polyoxyethylenated alkylphenols, polyoxyethylenated alcohols, polyoxyethylenated ethers and polyoxyethylenated sorbitol esters. Monomeric cationic surfactants, including quaternary ammonium salt compounds such as CTAB and quaternary phosphonium salt compounds can be used. Polymeric cationic surfactants including those comprising quaternary ammonium and phosphonium salt groups can also be used for this purpose.

In one embodiment the trigger solution is a composition comprising an aqueous buffer, a peroxide at a concentration of about $10^{-5}$ M to about 1M, and an enhancer at a concentration of about $10^{-5}$ M to about $10^{-1}$ M. The composition may optionally contain additives including surfactants, metal chelating agents, and preservatives to prevent or minimize microbial contamination. Trigger solution pH is typically between pH 6.0 to pH 9.0. In some embodiments, the pH is from pH 6.5 to pH 8.5, in further embodiments the pH is in the range of pH 7.0-8.0.

Specific Binding Pairs

A specific binding pair member or specific binding partner (sbp) is defined herein as a molecule, including biological molecules, having a specific binding affinity for another substance. A specific binding pair member includes DNA, RNA, oligonucleotides, antibodies, antibody fragments, antibody-DNA chimeras, antigens, haptens, proteins, peptides, lectins, avidin, streptavidin and biotin. Each specific binding pair member of a specific binding pair has specific binding affinity for the same substance (e.g. analyte). Each specific binding pair member is non-identical to the other specific binding pair member in a specific binding pair in at least that the specific binding pair members should not compete for the same or overlapping binding site on an analyte. For example, if a specific binding pair is composed of two antibodies, each sbp antibody has a different, non-competing epitope on the analyte.

The specific binding substances include, without limitation, antibodies and antibody fragments, antigens, haptens and their cognate antibodies, biotin and avidin or streptavidin, protein A and IgG, complementary nucleic acids or oligonucleotides, lectins and carbohydrates.

In addition to the aforementioned antigen-antibody, hapten-antibody or antibody-antibody pairs, specific binding pairs also can include complementary oligonucleotides or polynucleotides, avidin-biotin, streptavidin-biotin, hormone-receptor, lectin-carbohydrate, IgG protein A, binding protein-receptor, nucleic acid-nucleic acid binding protein and nucleic acid-anti-nucleic acid antibody. Receptor assays used in screening drug candidates are another area of use for the present methods. Any of these binding pairs can be adapted to use in the present methods by the three-component sandwich technique or the two-component competitive technique described above.

Chemiluminescent Compounds

The compounds used as chemiluminescent labels in the practice of the present disclosure have the general formula CL-L-RG wherein CL denotes a chemiluminescent moiety, L denotes a linking moiety to link the chemiluminescent moiety and a reactive group, and RG denotes a reactive group moiety for coupling to another material. The terms 'chemiluminescent group' and 'chemiluminescent moiety' are used interchangeably as are the terms 'linking moiety' and 'linking group'. The chemiluminescent moiety CL comprises a compound which undergoes a reaction with an activator resulting in it being converted into an activated compound. Reaction of the activated compound with a trigger solution forms an electronically excited state compound. The excited state may be either a singlet or triplet excited state. The excited state may directly emit light upon relaxation to the ground state or may transfer excitation energy to an emissive energy acceptor, thereby returning to the ground state. The energy acceptor is raised to an excited state in the process and emits light. It is desirable but not necessary, that the chemiluminescent reaction of the CL group, the activator and the trigger solution be rapid, taking place over a very brief time span; in one embodiment reaching peak intensity within a few seconds.

In one embodiment of the disclosure the chemiluminescent compounds are capable of being oxidized to produce chemiluminescence in the presence of the activator and a trigger solution. An exemplary class of compounds which by incorporation of a linker and reactive group could serve as the chemiluminescent label include aromatic cyclic diacylhydrazides such as luminol and structurally related cyclic hydrazides including isoluminol, aminobutylethylisoluminol (ABET), aminohexylethylisoluminol (AHEI), 7-dimethylaminonaphthalene-1,2-dicarboxylic acid hydrazide, ring-substituted aminophthalhydrazides, anthracene-2,3-dicarboxylic acid hydrazides, phenanthrene-1,2-dicarboxylic acid hydrazides, pyrenedicarboxylic acid hydrazides, 5-hydroxyphthalhydrazide, 6-hydroxyphthalhydrazide, as well as other phthalazinedione analogs disclosed in U.S. Pat. No. 5,420,275 to Masuya et al. and in U.S. Pat. No. 5,324,835 to Yamaguchi.

It is considered that any compound known to produce chemiluminescence by the action of hydrogen peroxide and a peroxidase will function as the chemiluminescent moiety of the chemiluminescent label compound used in the present disclosure. Numerous such compounds of various structural classes, including xanthene dyes such as fluorescein, eosin, rhodamine dyes, or rhodol dyes, aromatic amines and heterocyclic amines are known in the art to produce chemiluminescence under these conditions. Another example is the compound MCLA, 2-methyl-6-(p-methoxyphenyl)-3,7-dihydroimidazo[1,2-a]pyrazin-3-one. Another example is indole acetic acid, another is isobutyraldehyde, the latter typically being accompanied by a fluorescent energy acceptor for increasing the output of visible light. Trihydroxyaromatic compounds pyrogallol, phloroglucinol and purpurogallin, individually or in combination, are other examples of compounds that can serve as chemiluminescent moieties in the chemiluminescent labeling compounds of the disclosure.

In one embodiment a group of chemiluminescent label compounds comprising an acridan ketenedithioacetal (AK) useful in the methods of the disclosure comprises acridan compounds having formula IV

IV

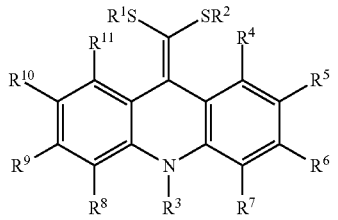

wherein at least one of the groups $R^1$-$R^{11}$ is a labeling substituent of the formula -L-RG wherein L is a linking group which can be a bond or another divalent or polyvalent group, RG is a reactive group which enables the chemiluminescent labeling compound to be bound to another compound, $R^1$, $R^2$ and $R^3$ are organic groups containing from 1 to 50 non-hydrogen atoms, and each of $R^4$-$R^{11}$ is hydrogen or a non-interfering substituent. The labeling substituent -L-RG can be present on one of $R^1$ or $R^2$ although it can also be present as a substituent on $R^3$ or one of $R^4$-$R^{11}$.

The groups $R^1$ and $R^2$ in the compound of formula IV can be any organic group containing from 1 to about 50 non hydrogen atoms selected from C, N, O, S, P, Si and halogen atoms which allows light production. By the latter is meant that when a compound of formula I undergoes a reaction of the present disclosure, an excited state product compound is produced and can involve the production of one or more chemiluminescent intermediates. The excited state product can emit the light directly or can transfer the excitation energy to a fluorescent acceptor through energy transfer causing light to be emitted from the fluorescent acceptor. In one embodiment $R^1$ and $R^2$ are selected from substituted or unsubstituted alkyl, substituted or unsubstituted alkenyl, substituted or unsubstituted alkynyl, substituted or unsubstituted aryl, and substituted or unsubstituted aralkyl groups of 1-20 carbon atoms. When $R^1$ or $R^2$ is a substituted group, it can be substituted with 1-3 groups selected from carbonyl groups, carboxyl groups, tri($C_1$-$C_8$ alkyl)silyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, and quaternary phosphonium groups. In one embodiment, $R^1$ or $R^2$ is substituted with the labeling substituent of the formula -L-RG where L is a linking group and RG is a reactive group.

The group $R^3$ is an organic group containing from 1 to 50 non-hydrogen atoms selected from C, N, O, S, P, Si and halogen in addition to the necessary number of H atoms required to satisfy the valences of the atoms in the group. In one embodiment $R^3$ contains from 1 to 20 non-hydrogen atoms. In another embodiment the organic group is selected from the group consisting of alkyl, substituted alkyl, substituted or unsubstituted alkenyl, substituted or unsubstituted alkynyl, substituted or unsubstituted aryl, and substituted or unsubstituted aralkyl groups of 1-20 carbon atoms. In another embodiment groups for $R^3$ include substituted or unsubstituted $C_1$-$C_4$ alkyl groups, phenyl, substituted or unsubstituted benzyl groups, alkoxyalkyl, carboxyalkyl and alkylsulfonic acid groups. When $R^3$ is a substituted group, it can be substituted with 1-3 groups selected from carbonyl groups, carboxyl groups, tri($C_1$-$C_8$ alkyl)silyl groups, a $SO_3$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, and quaternary phosphonium groups. The group $R^3$ can be joined to either $R^7$ or $R^8$ to complete a 5 or 6-membered ring. In one embodiment, $R^3$ is substituted with the labeling substituent of the formula -L-RG.

In the compounds of formula IV, the groups $R^4$-$R^{11}$ each are independently H or a substituent group which permits the excited state product to be produced and generally contain from 1 to 50 atoms selected from C, N, O, S, P, Si and halogens. Representative substituent groups which can be present include, without limitation, alkyl, substituted alkyl, aryl, substituted aryl, aralkyl, alkenyl, alkynyl, alkoxy, aryloxy, halogen, amino, substituted amino, carboxyl, carboalkoxy, carboxamide, cyano, and sulfonate groups. Pairs of adjacent groups, e.g., $R^4$-$R^8$ or $R^8$-$R^6$, can be joined together to form a carbocyclic or heterocyclic ring system comprising at least one 5 or 6-membered ring which is fused to the ring to which the two groups are attached. Such fused heterocyclic rings can contain N, O or S atoms and can contain ring substituents other than H such as those mentioned above. One or more of the groups $R^4$-$R^{11}$ can be a labeling substituent of the formula -L-RG. In one embodiment $R^4$-$R^{11}$ are selected from hydrogen, halogen and alkoxy groups such as methoxy, ethoxy, t-butoxy and the like. In another embodiment a group of compounds has one of $R^8$, $R^6$, $R^9$ or $R^{16}$ as a halogen and the other of $R^4$-$R^{11}$ are hydrogen atoms.

Substituent groups can be incorporated in various quantities and at selected ring or chain positions in the acridan ring in order to modify the properties of the compound or to provide for convenience of synthesis. Such properties include, e.g., chemiluminescence quantum yield, rate of reaction with the enzyme, maximum light intensity, duration of light emission, wavelength of light emission and solubility in the reaction medium. Specific substituents and their effects are illustrated in the specific examples below, which, however, are not to be considered limiting the scope of the disclosure in any way. For synthetic expediency compounds of formula I desirably have each of $R^4$ to $R^{11}$ as a hydrogen atom.

In another embodiment a group of compounds have formula V wherein each of $R^4$ to $R^{11}$ is hydrogen. The groups $R^1$, $R^2$ and $R^3$ are as defined above.

V

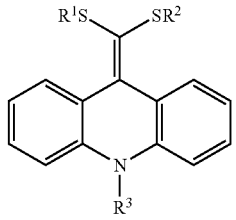

Labeling compounds of formulas IV or V have the groups -L-RG as a substituent on the group $R^1$ or $R^2$. In an embodiment a labeling compound has formula VI.

VI

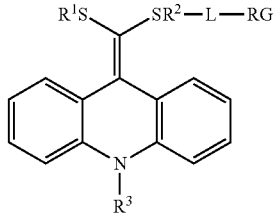

Representative labeling compounds have the structures below. Additional exemplary compounds and their use in attachment to other molecules and solid surfaces are described in the specific examples below. The structures shown below illustrate exemplary compounds of the formula CL-L-R.

TABLE 8

AK1

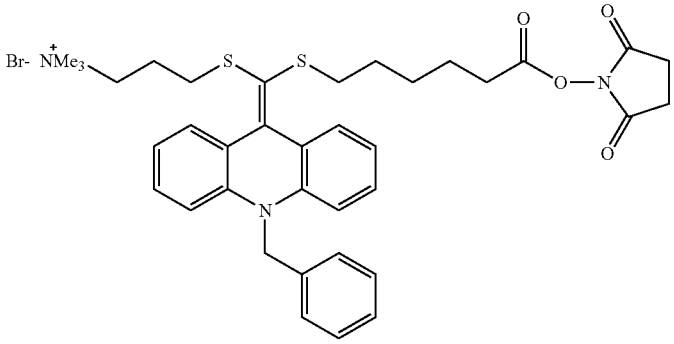

AK2

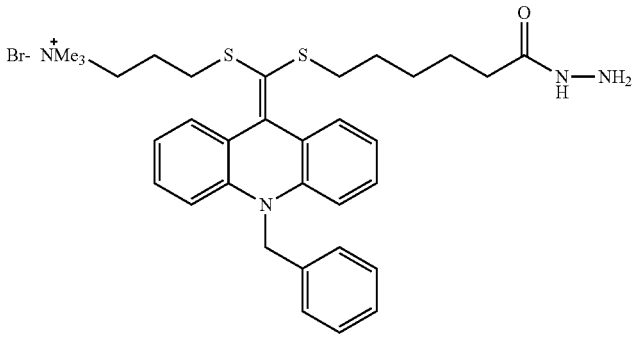

TABLE 8-continued
AK3
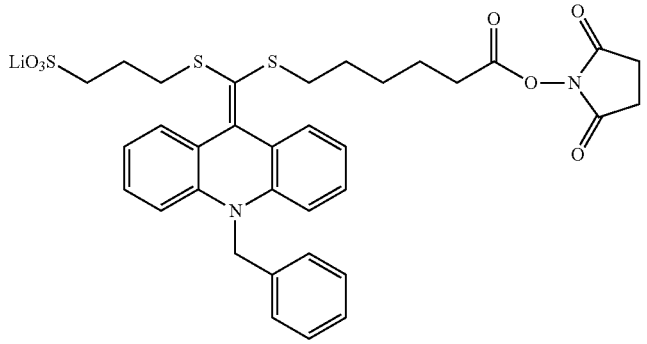
AK4
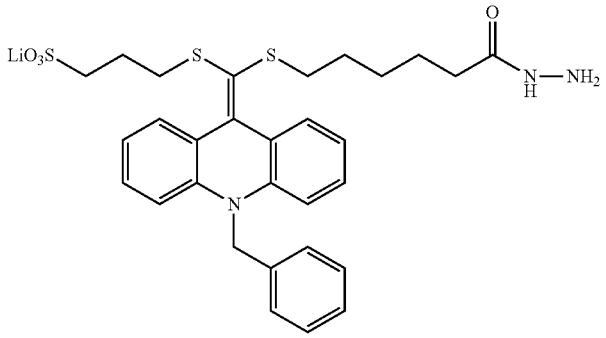
AK5
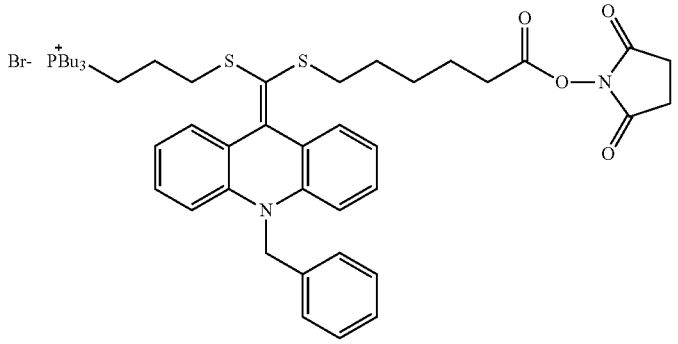
AK6
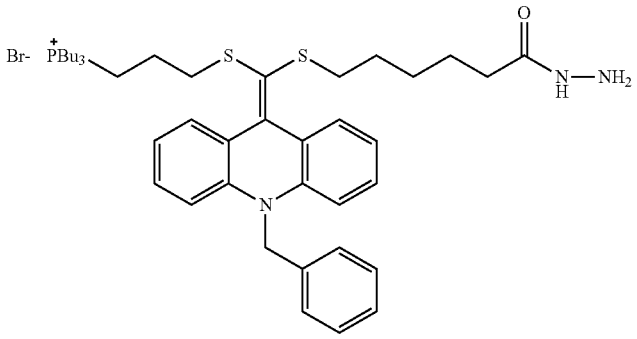

TABLE 8-continued

AK7

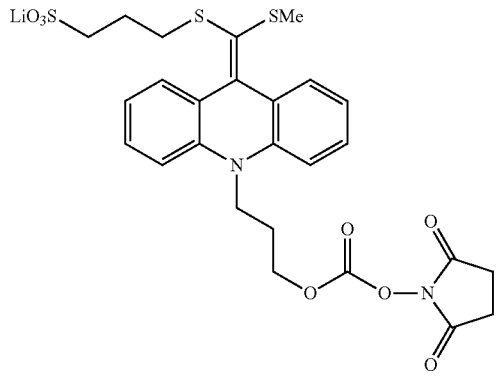

The above specific AK compounds and compounds of general formulas IV, V and VI shown above can be prepared by the skilled organic chemist using generally known methods including methods disclosed in published application US2007/0172878. In an exemplary method an N-substituted and optionally ring-substituted acridan ring compound is reacted with a strong base followed by $CS_2$ to form an acridan dithiocarboxylate. The dithiocarboxylate is esterified by conventional methods to install one of the substituents designated $R^1$. The resulting acridan dithioester is again deprotonated with a strong base such as n-BuLi or NaH in an aprotic solvent and S-alkylated with a suitable reagent containing a leaving group and an $R^2$ moiety. It will be readily apparent to one of ordinary skill in organic chemistry that the $R^2$ moiety may be subject to further manipulation to install suitable reactive groups.

Another class of chemiluminescent moieties includes acridan esters, thioesters and sulfonamides disclosed in U.S. Pat. Nos. 5,491,072; 5,523,212; 5,593,845; and 6,030,803. Chemiluminescent labeling compounds in this class have a chemiluminescent moiety CL of formula VII below wherein Z is O, S or $NR^{11}SO_2Ar$, wherein $R^{11}$ is alkyl or aryl, wherein Ar is aryl or alkyl-substituted aryl, wherein $R^1$ is $C_{1-8}$ alkyl, halo-substituted $C_{1-8}$ alkyl, aralkyl, aryl, or aryl substituted with alkyl, alkenyl, alkynyl, aralkyl, aryl, alkoxy, alkoxyalkyl, halogen, carbonyl, carboxyl, carboxamide, cyano, trifluoromethyl, trialkylammonium, nitro, hydroxy, amino and mercapto groups, wherein $R^2$ is selected from alkyl, heteroalkyl, aryl, and aralkyl groups, and wherein $R^{3-10}$ are each hydrogen or 1 or 2 substituents are selected from alkyl, alkoxy, hydroxy, and halogen, and the remaining of $R^{3-10}$ are hydrogen. In one embodiment each of $R^{3-10}$ is hydrogen and $R^1$ is a labeling substituent. In another embodiment one of $R^{3-10}$ is a labeling substituent and the others of $R^{3-10}$ are hydrogen.

Another class of chemiluminescent moieties includes the heterocyclic compounds disclosed in U.S. Pat. Nos. 5,922,558; 6,696,569; and 6,891,057. In one embodiment the compounds comprise a heterocyclic ring, comprising a nitrogen, oxygen or sulfur-containing five or six-membered ring or multiple ring group to which is bonded an exocyclic double bond, the terminal carbon of which is substituted with two atoms selected from oxygen, and sulfur atoms.

In another embodiment the chemiluminescent labeling compounds comprises a chemiluminescent acridan enol derivative of formula VIII below wherein $R^1$ is selected from alkyl, alkenyl, alkynyl, aryl, and aralkyl groups of 1-20 carbon atoms any of which can be substituted with 1-3 groups selected from carbonyl groups, carboxyl groups, tri($C_1$-$C_8$ alkyl)silyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, or quaternary phosphonium groups, wherein X is selected from $C_1$-$C_8$ alkyl, aryl, aralkyl groups, alkyl or aryl carboxyl groups having from 1-20 carbon atoms, tri($C_1$-$C_8$ alkyl)silyl groups, a $SO_3^-$ group, glycosyl groups and phosphoryl groups of the formula PO(OR')(OR") wherein R' and R" are independently selected from $C_1$-$C_8$ alkyl, cyanoalkyl, aryl and aralkyl groups, trialkylsilyl groups, alkali metal cations, alkaline earth cations, ammonium and trialkylphosphonium cations, wherein Z is selected from O and S atoms, wherein $R^6$ is selected from substituted or unsubstituted $C_1$-$C_4$ alkyl, phenyl, benzyl, alkoxyalkyl and carboxyalkyl groups, wherein $R^{7-14}$ are each hydrogen or 1 or 2 substituents are selected from alkyl, alkoxy, hydroxy, and halogen and the remaining of $R^{7-14}$ are hydrogen. In one embodiment each of $R^{7-14}$ is hydrogen and $R^1$ is a labeling substituent. In another embodiment one of $R^{7-14}$ is a labeling substituent and the others of $R^{7-14}$ are hydrogen.

VII

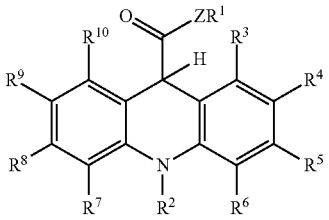

VIII

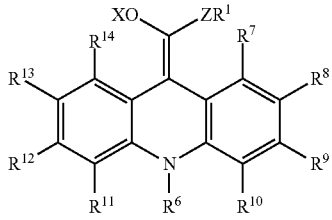

In another embodiment the chemiluminescent labeling compounds comprises a chemiluminescent compound of formula IX below wherein $R^1$ is selected from alkyl, alkenyl, alkynyl, aryl, and aralkyl groups of 1-20 carbon atoms any of which can be substituted with 1-3 groups selected from carbonyl groups, carboxyl groups, tri($C_1$-$C_8$ alkyl)silyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, or quaternary phosphonium groups, wherein X is selected from $C_1$-$C_8$ alkyl, aryl, aralkyl groups, alkyl or aryl carboxyl groups having from 1-20 carbon atoms, tri($C_1$-$C_8$ alkyl)silyl groups, a $SO_3^-$ group, glycosyl groups and phosphoryl groups of the formula PO(OR')(OR") wherein R' and R" are independently selected from $C_1$-$C_8$ alkyl, cyanoalkyl, aryl and aralkyl groups, trialkylsilyl groups, alkali metal cations, alkaline earth cations, ammonium and trialkylphosphonium cations, wherein $Z^1$ and $Z^2$ are each selected from O and S atoms and wherein $R^2$ and $R^3$ are independently selected from hydrogen and $C_1$-$C_8$ alkyl.

IX

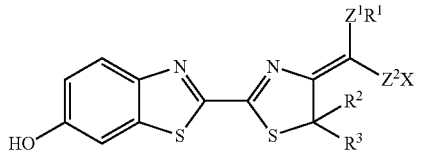

Linking Group (L).

The linking group in any of the chemiluminescent compounds used in the present disclosure can be a bond, an atom, divalent groups and polyvalent groups, or a straight, or branched chain of atoms some of which can be part of a ring structure. The substituent usually contains from 1 to about 50 non-hydrogen atoms, more usually from 1 to about 30 non-hydrogen atoms. In another embodiment atoms comprising the chain are selected from C, O, N, S, P, Si, B, and Se atoms. In another embodiment atoms comprising the chain are selected from C, O, N, P and S atoms. The number of atoms other than carbon in the chain is normally from 0-10. Halogen atoms can be present as substituents on the chain or ring. Typical functional groups comprising the linking substituent include alkylene, arylene, alkenylene, ether, peroxide, carbonyl as a ketone, ester, carbonate ester, thioester, or amide group, amine, amidine, carbamate, urea, imine, imide, imidate, carbodiimide, hydrazino, diazo, phosphodiester, phosphotriester, phosphonate ester, thioether, disulfide, sulfoxide, sulfone, sulfonate ester, sulfate ester, and thiourea groups. In another embodiment the group is an alkylene chain of 1-20 atoms terminating in a —$CH_2$—, —O—, —S—, —NH—, —NR—, —SiO—, —C(═O)—, —OC(═O)—, —C(═O)O—, —SC(═O)—, —C(═O)S—, —NRC(═O)—, —NRC(═S)—, or —C(═O)NR— group, wherein R is $C_{1-8}$ alkyl. In another embodiment the linking group is a poly(alkylene-oxy) chain of 3-30 atoms terminating in a —$CH_2$—, —O—, —S—, —NH—, —NR—, —SiO—, —C(═O)—, —OC(═O)—, —C(═O)O—, —SC(═O)—, —C(═O)S—, —NRC(═O)—, —NRC(═S)—, or —C(═O)NR— group, wherein R is $C_{1-8}$ alkyl.

Reactive Group.

The reactive group RG is an atom or group whose presence facilitates bonding to another molecule by covalent attachment or physical forces. In some embodiments, attachment of a chemiluminescent labeling compound of the present disclosure to another compound or substance will involve loss of one or more atoms from the reactive group for example when the reactive group is a leaving group such as a halogen atom or a tosylate group and the chemiluminescent labeling compound is covalently attached to another compound by a nucleophilic displacement reaction.

In one embodiment RG is an N-hydroxysuccinimide (NHS) ester group. The skilled artisan will readily understand that a substance to be labeled with such a labeling compound comprising an NHS ester group will react with a moiety on the substance, typically an amine group, in the process splitting the ester C—O bond, releasing N-hydroxysuccinimide and forming a new bond between an atom of the substance (N if an amine group) and the carbonyl carbon of the labeling compound. In another embodiment RG is a hydrazine moiety, —$NHNH_2$. As is known in the art this group reacts with a carbonyl group in a substance to be labeled to form a hydrazide linkage.

In other embodiments, attachment of a chemiluminescent labeling compound to another compound by covalent bond formation will involve reorganization of bonds within the reactive group as occurs in an addition reaction such as a Michael addition or when the reactive group is an isocyanate or isothiocyanate group. In still other embodiments, attachment will not involve covalent bond formation, but rather physical forces in which case the reactive group remains unaltered. By physical forces is meant attractive forces such as hydrogen bonding, electrostatic or ionic attraction, hydrophobic attraction such as base stacking, and specific affinity interactions such as biotin-streptavidin, antigen-antibody and nucleotide-nucleotide interactions.

Reactive groups for chemical binding of labels to organic and biological molecules include, but are not limited to, the following: a) Amine reactive groups: —N═C═S, —SO2Cl, —N═C═O, —SO2CH2CF3; b) Thiol reactive groups: —S—S—R; c) Carboxylic acid reactive groups: —NH2, —OH, —SH, —NHNH2; d) Hydroxyl reactive groups: —N═C═S, —N═C═O, —SO2Cl, —SO2CH2CF3; e) Aldehyde/ketone reactive groups: —NH2, —ONH2, —NHNH2; and f) Other reactive groups, e.g., R—N3, R—C≡CH.

In one embodiment reactive groups include OH, $NH_2$, $ONH_2$, $NHNH_2$, COOH, $SO_2CH_2CF_3$, N-hydroxysuccinimide ester, N-hydroxysuccinimide ether and maleimide groups.

Bifunctional coupling reagents can also be used to couple labels to organic and biological molecules with moderately reactive groups (see L. J. Kricka, Ligand-Binder Assays, Marcel Dekker, Inc., New York, 1985, pp. 18-20, Table 2.2 and T. H Ji, "Bifunctional Reagents," Methods in Enzymology, 91, 580-609 (1983)). There are two types of bifunctional reagents: those that become incorporated into the final structure, and those that do not and serve only to couple the two reactants.

Aqueous Solutions

Aqueous solutions suitable for use in the present disclosure are generally solutions containing greater than 50% water. Aqueous solutions described herein are suitable for uses including reaction mixture, sample dilution, calibrator solutions, chemiluminescent-labeled sbp solutions, activator-labeled sbp solutions, enhancer solutions, and trigger solution, or concentrated solutions of one or more of: chemiluminescent-labeled sbp, activator-labeled sbp, enhancer, trigger, sample, and/or selective signal inhibiting agents. In many embodiments, aqueous solutions are aqueous buffer solutions. Suitable aqueous buffers include any of the commonly used buffers capable of maintaining an environment in aqueous solution maintaining analyte solubility, maintaining reactant solubility, and permitting the chemiluminescent reaction to proceed. Exemplary buffers include phosphate, borate, acetate, carbonate, tris(hydroxy-methyl-amino)methane (tris), glycine, tricine, 2-amino-2-methyl-1-propanol, diethanolamine MOPS, HEPES, MES and the like. Typically aqueous solutions for use according to the present disclosure will have a pH in the range of about 5 to about 10.5.

Suitable aqueous solutions may include one or more of the following additional components: salts, biological buffers, alcohols, including ethanol, methanol, glycols, and detergents. In some embodiments, aqueous solutions include Tris buffered aqueous solutions, such as Buffer II (TRIS buffered saline, surfactant, <0.1% sodium azide, and 0.1% ProClin® 300 (Rohm and Haas) available commercially from Beckman Coulter, Inc., Brea Calif.,).

In some embodiments, an aqueous solution emulating human serum is utilized. One such synthetic matrix is 20 mM PBS, 7% BSA, pH 7.5 with 0.1% ProClin® 300. Synthetic matrixes can be used for, but not limited to sample dilution, calibrator solutions, chemiluminescent-labeled sbp solutions, activator-labeled sbp solutions, enhancer solutions, and trigger solutions. The term "PBS" refers in the customary sense to phosphate buffered saline, as known in the art. The term "BSA" refers in the customary sense to bovine serum albumin, as known in the art.

Assay Formats

Assay formats require a specific binding action to mediate the proximity between the chemiluminescent label of the chemiluminescent-labeled sbp and the activator label of the activator-labeled sbp.

In another embodiment an analog of the analyte is used comprising an activator-analyte analog conjugate. In another embodiment a labeled analyte is used comprising an activator-analyte conjugate. The activator-analyte analog conjugate or activator-analyte conjugate and analyte will competitively bind with the specific binding partner for the analyte. It will be apparent that in this type of assay method a negative correlation between the amount of analyte in the sample and the intensity of chemiluminescence will result.

In addition to attachment of chemiluminescent label through antibodies for binding antigens or other proteins or other antibodies via an immunoassay, the present methods can use chemiluminescent-labeled nucleic acids for detecting nucleic acids through binding of complementary nucleic acids. The use in this regard is not particularly limited with regard to the size of the nucleic acid, the only criterion being that the complementary partners be of sufficient length to permit stable hybridization. Nucleic acids as used herein include gene length nucleic acids, shorter fragments of nucleic acids, polynucleotides and oligonucleotides, any of which can be single or double stranded. In the practice of the disclosure using nucleic acids as specific binding partners, a nucleic acid is covalently attached or physically immobilized on a surface of a solid support to capture an analyte nucleic acid. The chemiluminescent label can be attached to the capture nucleic acid, or the label can be connected with an auxiliary substance, also attached to the capture nucleic acid as explained above. The capture nucleic acid will have full or substantially full sequence complementarity to a sequence region of the analyte nucleic acid. When substantially complementary, the capture nucleic acid may possess a terminal overhanging portion, a terminal loop portion or an internal loop portion that is not complementary to the analyte provided that it does not interfere with or prevent hybridization with the analyte. The reverse situation may also occur where the overhang or loop resides within the analyte nucleic acid. Capture nucleic acid, analyte nucleic acid, a conjugate of an activator, and a third nucleic acid are allowed to hybridize. The third nucleic acid is substantially complementary to a sequence region of the analyte nucleic acid different from the region complementary to the capture nucleic acid. The hybridization of the capture nucleic acid and activator conjugate nucleic acid with the analyte can be performed consecutively in either order or simultaneously. As a result of this process, the chemiluminescent label is brought into a reactive configuration with the activator by virtue of specific hybridization reactions bringing the activator near the chemiluminescent label attached to the surface of the support. Trigger solution is provided and chemiluminescence detected as described above.

Another embodiment comprises a variation wherein a conjugate of the analyte with the activator is used. The analyte nucleic acid-activator conjugate and analyte nucleic acid will competitively bind with the specific binding partner for the analyte nucleic acid. It will be apparent that in this type of assay method a negative correlation between the amount of analyte in the sample and the intensity of chemiluminescence will result.

In addition to antibody-based and nucleic acid-based systems, other specific binding pairs as are generally known to one of ordinary skill in the art of binding assays can serve as the basis for test methods according to the present disclosure. Antibody-hapten pairs can also be used. Fluorescein/anti-fluorescein, digoxigenin/anti-digoxigenin, and nitrophenyl/anti-nitrophenyl pairs are exemplary.

Detection

Light emitted by the present method can be detected by any suitable known means such as a luminometer, x-ray film, high speed photographic film, a CCD camera, a scintillation counter, a chemical actinometer or visually. Each detection means has a different spectral sensitivity. The human eye is optimally sensitive to green light, CCD cameras display maximum sensitivity to red light, X-ray films with maximum response to either UV to blue light or green light are available. Choice of the detection device will be governed by the application and considerations of cost, convenience, and whether creation of a permanent record is required. In those embodiments where the time course of light emission is rapid, it is advantageous to perform the triggering reaction to produce the chemiluminescence in the presence of the detection device. As an example the detection reaction may be performed in a test tube or microwell plate housed in a luminometer or placed in front of a CCD camera in a housing adapted to receive test tubes or microwell plates.

Uses

The present assay methods find applicability in many types of specific binding pair assays. Foremost among these are chemiluminescent enzyme linked immunoassays, such as an ELISA. Various assay formats and the protocols for performing the immunochemical steps are well known in the art and include both competitive assays and sandwich assays. Types of substances that can be assayed by immunoassay according to the present disclosure include proteins, peptides, antibodies, haptens, drugs, steroids and other substances that are generally known in the art of immunoassay.

The methods of the present disclosure are also useful for the detection of nucleic acids. In one embodiment a method makes use of enzyme-labeled nucleic acid probes. Exemplary methods include solution hybridization assays, DNA detection in Southern blotting, RNA by Northern blotting, DNA sequencing, DNA fingerprinting, colony hybridizations and plaque lifts, the conduct of which is well known to those of skill in the art.

Kits

The present disclosure also contemplates providing kits for performing assays in accordance with the methods of the present disclosure.

In another embodiment of the present disclosure a kit is provided containing assay materials including chemiluminescent-labeled sbp, activator-labeled sbp, selective signal inhibiting agent, and trigger solution. In some embodiments, these assay materials are provided in aqueous solution. In some embodiments, one or more of the assay materials are provided in concentrated aqueous solution. Concentrated aqueous solutions of the assay materials are provided to a reaction mixture in volumes to reach the desired final concentration of each assay material. In some embodiments, additional aqueous solution is provided for dilution of concentrated aqueous solutions. In other embodiments, one or more assay materials are provided in a lyophilized or solid form. In such embodiments, additional aqueous solution may be provided to convert the lyophilized or solid assay material into aqueous solution or aqueous solution concentrate.

In some kit embodiments, each assay material is provided in a separate container. In other kit embodiments, one or more assay materials are provided in a common container. In still other kit embodiments, one or more assay materials are provided in a common container divided in wells wherein each well holds an assay material.

Kits may comprise, in packaged combination, chemiluminescent labels as either the free labeling compounds, chemiluminescent labeled specific binding partners, or chemiluminescent labeled auxiliary substances such as blocking proteins, along with a trigger solution and instructions for use. Kits may optionally also contain activator conjugates, analyte calibrators and controls, diluents and reaction buffers if chemiluminescent labeling is to be performed by the user.

Instrument

The assay methods described in the present disclosure may be automated for rapid performance by employing a system. A system for performing assays of the present disclosure requires the fluid handling capabilities for aliquoting and delivering trigger solution to a reaction vessel containing the other reactants and reading the resulting chemiluminescent signal. In embodiments of such a system, a luminometer is positioned proximal to the reaction vessel at the time and place of trigger solution injection. Preferably, the detection system including luminometer or other detection device acts in concert with the fluid handling system injecting the trigger solution. Additionally, an automated system for performing assays of the present disclosure has fluid handling capabilities for aliquoting and delivering the other reactants and sample to a reaction vessel. In an embodiment, a system for performing the assay method of the present invention includes a fluid handling system for delivery of sample into the reaction mixture, a fluid handling system for delivery of a chemiluminescent-labeled specific binding partner, an activator-labeled specific binding partner, selective signal inhibiting agent into the reaction mixture, and a fluid handling system for delivery of trigger solution into the reaction mixture to release a chemiluminescent signal; and a detection system to detect the chemiluminescent signal, wherein the a fluid handling system for delivery of trigger solution acts in concert with the detection system to measure the chemiluminescent signal releases at and following trigger fluid injection. These fluid handling systems may be the same system or different systems dependent on the configuration of the system.

A modified DXI 800 instrument was modified to perform the assay methods of the present disclosure. Further description of the DXI 800 instrument without modification is available in the UniCel DXI User's Guide, ©2007, Beckman Coulter, herein incorporated by reference. For use in performing the methods described herein, a DXI® 800 immunoassay instrument was modified by incorporating a photon-counting luminometer (same model as used in commercially available DXI 800 instrument) positioned for detection near the location of (approximately 19 mm from) the reaction vessel during and immediately after trigger solution injection.

The substrate delivery system within the DXI® 800 immunoassay was used to deliver trigger solution. Some additional components of the DXI® 800 immunoassay instrument not needed for assays according to the methods described herein were removed for convenience, for example magnets and aspiration system used for separation and washing necessary for conventional immunoassay but not used in methods of the present invention. The modified DXI® 800 immunoassay instrument was utilized for convenience in automating reaction vessel handling, pipeting of reagents, detection, and provided temperature control at 37° C. Other commercially available instrumentation may be similarly utilized to perform the assay methods described herein so long as the instrument is able to or may be modified to inject trigger solution into a reaction vessel and start detection of chemiluminescent signal in either a concurrent or nearly concurrent manner. The detection of chemiluminescent signal may be of very short duration, several milliseconds, such as one cycle of a photomultiplier tube (PMT) or may be extended for several seconds. All or a portion of the signal collected may be used for subsequent data analysis.

The detection of chemiluminescent signal may be of very short duration, several milliseconds, such as one cycle of a photomultiplier tube (PMT) or may be extended for several seconds. All or a portion of the signal collected may be used for subsequent data analysis. For example, in a typical procedure described below, light intensity is summed for 0.25 sec, centered on the flash of light, in other procedures, light intensity is summed for 5 sec for the first 0.5 sec being a delay before injection.

EXAMPLES

Glossary

AHTL: N-acetyl homocysteine lactone
AK: acridan
CKMB: creatine kinase isoenzyme
DMF: dimethyl formamide
EDC: 1-ethyl-3-(3-dimethylaminopropyl) carbodiimide
HRP: horseradish peroxidase
MS-PEG: amine-reactive linear polyethylene glycol polymer with terminal methyl groups
Na2EDTA: sodium salt of ethylene diamine tetraacetic acid.
NHS: N-hydroxysuccinimide
PEG: polyethylene glycol; specifically oligomers or polymers with molecular weight <20,000 g/mol.
PEO: polyethylene oxide; specifically polymers with molecular weight >20,000 g/mol.
PMP: 1-phenyl-3-methyl-5-pyrazolone
PSA: prostate specific antigen Sulfo-SMCC: Sulfosuccinimidyl-4-(N-maleimidomethyl) cyclohexane-1-carboxylate TBS: Tris-buffered saline TnI: Troponin I; cTnI is cardiac Troponin I.

Tris: 2-amino-2-hydroxymethyl-propane-1,3-diol, also known as tris-(hydroxymethyl)aminomethane Tween®-20: polyoxyethylene(20) sodium monolaurate; commercially available from Sigma-Aldrich, St. Louis (Mo.).

Materials:

Samples of Known Concentration: Samples of known concentration for use in the assays and assay methods described below were typically prepared by adding purified protein of the designated analyte to human serum free of that analyte. For example, PSA samples of known PSA protein were prepared by spiking PSA derived from human seminal fluid into PSA-free female serum to reach the stated PSA concentration in the tables presented in the examples below. The samples, if stored prior to use, were stored at 4 C or frozen and thawed prior to use. The samples of known concentration were generally prepared as was customary for calibration sets useful for generation of a standard curve to be used in combination with the assay methods to determine analyte concentration in samples of unknown analyte concentration.

Trigger Solution including Enhancer: An aqueous trigger solution used in many of the examples below, is referred to as Trigger Solution A. Trigger Solution A contains 8 mM p-hydroxycinnamic acid, 1 mM Na2EDTA, 105 mM Urea Peroxide, and 0.2% Tween®-20 in an aqueous buffer solution of 25 mM Tris at pH 8.0 with approximately 3% ethanol. All components are commercially available from various suppliers, such as Sigma, St. Louis, Mo.

Buffer II: (TRIS buffered saline, surfactant, <0.1% sodium azide, and 0.1% ProClin® 300 (Rohm and Haas) available commercially from Beckman Coulter, Inc., Brea Calif.,).

Instruments:

Modified DxI® 800 Immunoassay Instrument (Beckman Coulter, Inc. Brea, Calif.): A modified DXI® 800 instrument was used to perform the assay methods described in several examples below where noted. For use in performing the methods described herein, a DXI® 800 instrument was modified by incorporating a photo-counting luminometer (same model as used in commercially available DXI® 800 instrument) positioned for detection near the location of (approximately 19 mm from) the reaction vessel during and immediately after trigger solution injection. The substrate delivery system within the DXI® 800 immunoassay was used to deliver trigger solution. Some additional components of the DXI® 800 immunoassay instrument not needed for assays according to the methods described herein were removed for convenience, for example magnets and aspiration system used for separation and washing necessary for conventional immunoassay but not used in methods of the present invention. The modified DXI® 800 immunoassay instrument was utilized for convenience in automating reaction vessel handling, pipeting of reagents, detection, and provided temperature control at 37° C. Other commercially available instrumentation may be similarly utilized to perform the assay methods described herein so long as the instrument is able to or may be modified to inject trigger solution into a reaction vessel and start detection of chemiluminescent signal in either a concurrent or nearly concurrent manner. Other example instruments are listed below.

The detection of chemiluminescent signal may be of very short duration, several milliseconds, such as one cycle of a photomultiplier tube (PMT) or may be extended for several seconds. All or a portion of the signal collected may be used for subsequent data analysis.

Luminoskan Ascent® plate luminometer, (Thermo Fischer Scientific, Inc., Waltham, Mass.). Unmodified. Methods performed at room temperature.

SpectraMax® L microplate luminometer, (Molecular Devices, Sunnyvale, Calif.) Unmodified. Methods performed at room temperature using fast read kinetic mode.

Example 1. Screening Compounds for Effectiveness as SSIA

A. Screening SSIA by Homogeneous PSA Immunoassay

This example presents one method used for testing of candidate compounds for functionality as SSIA in assays of the present disclosure. Testing was conducted in a model screening immunoassay of the protein PSA. Tests were run using a 96-well microtiter plate format. A solution containing 30 μL of mouse anti-PSA-AK1 (66 ng), 30 μL of mouse anti-PSA-HRP conjugate (7.8 ng), 36 μL of human female serum, and 24 μL of PSA calibrator were pipetted into each well. The plate was incubated at 37° C. for 10 minutes. A 5 μL aliquot of the test compound (various concentrations) was added to each well. Chemiluminescence was triggered by the addition of 100 μL of a solution of a trigger solution whose composition is listed below. The chemiluminescent flash was integrated for 5 seconds after the addition of the trigger solution using a Luminoskan Asent® plate luminometer, (Thermo Fischer Scientific, Inc., Waltham, Mass.).

Each candidate compound was tested at least two levels of PSA: zero and 129 ng PSA/mL (calibrator S5) and/or 2 ng PSA/mL (calibrator S2). For brevity only the results of one representative concentration of each candidate compound are presented. Compounds are considered to be effective at improving assay performance if S5/S0 is improved in relation to a control. It is desirable that the improvement factor be at least 2 (S5/S0≥about 20-30) and more desirable that improvement factor be at least 5 (S5/S0≥about 50), yet more desirable that S5/S0 be ≥100 in the present screen. Many compounds were found that exhibited effectiveness as SSIA in this screening test, others were found to be ineffective or have limited effect.

TABLE 9

Test compound, final concentration and S5/S0

| Test Compound | Conc. | S5/S0 |
|---|---|---|
| Control (Serum) | | 5-10 |
| 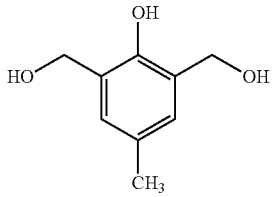 | 0.122 mM | 23 |
| 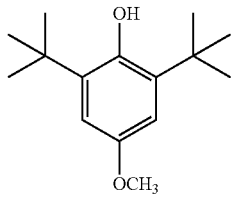 | 0.122 mM | 19 |

TABLE 9-continued
| Test compound, final concentration and S5/S0 | | |
|---|---|---|
| Test Compound | Conc. | S5/S0 |
| 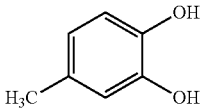 | 0.122 mM | 142 |
| 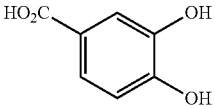 | 0.122 mM | 178 |
| 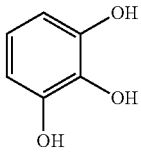 | 0.122 mM | 69 |
| 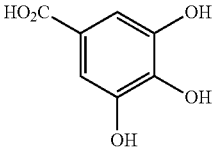 | 0.122 mM | 135 |
| 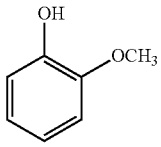 | 0.122 mM | 13 |
| 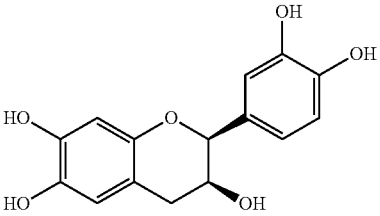 | 0.122 mM | 323 |
| 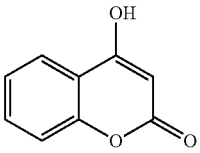 | 0.122 mM | 17 |
| 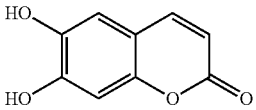 | 0.122 mM | 105 |
| 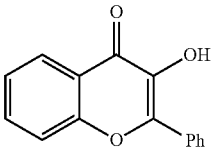 | 0.122 mM | 13 |
| 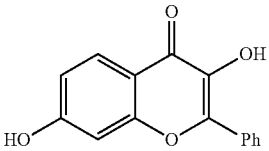 | 0.122 mM | 14 |
TABLE 9-continued
| Test compound, final concentration and S5/S0 | | |
|---|---|---|
| Test Compound | Conc. | S5/S0 |
| 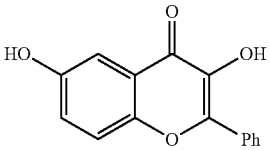 | 0.122 mM | 9 |
| 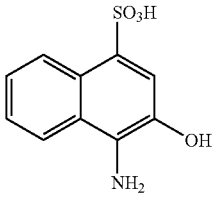 | 0.122 mM | 65 |
| 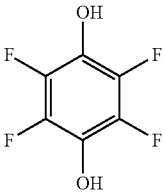 | 0.014 mM | 50 |
| 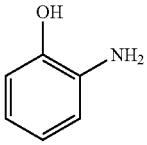 | 0.122 mM | 649 |
| 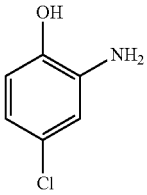 | 0.244 mM | 205 |
| 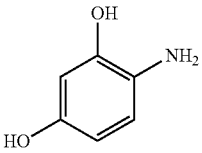 | 0.030 mM | 161 |
| 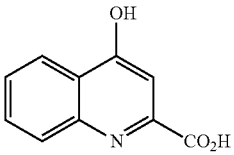 | 0.122 mM | 6 |
| 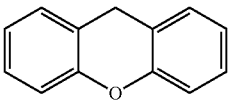 | 0.122 mM | 4 |

TABLE 9-continued
| Test compound, final concentration and S5/S0 | | |
|---|---|---|
| Test Compound | Conc. | S5/S0 |
| 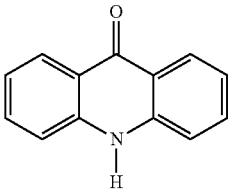 | 0.122 mM | 14 |
| 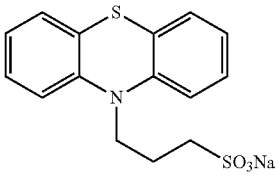 | 0.244 mM | 50 |
| 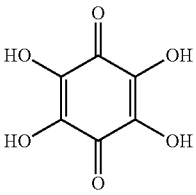 | 0.061 mM | 51 |
| 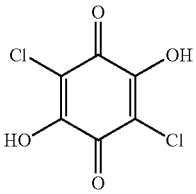 | 0.031 mM | 7 |
| 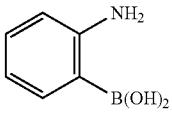 | 0.122 mM | 108 |
| 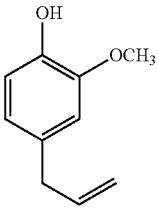 | 0.244 mM | 60 |
| Glutathione | 122 uM | 77 |
| L-Cysteine | 122 uM | 22 |
| NaN3 | 34 uM | 19 |
| TMB | 61 uM | 20 |
TABLE 9-continued
| Test compound, final concentration and S5/S0 | | |
|---|---|---|
| Test Compound | Conc. | S5/S0 |
| 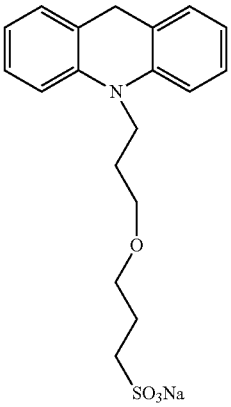 | 0.244 mM | 649 |
| 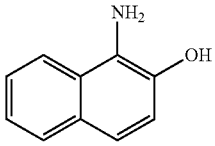 | mM | 205 |
| 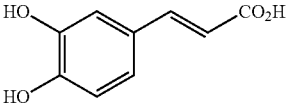 | 0.122 mM | 161 |
| 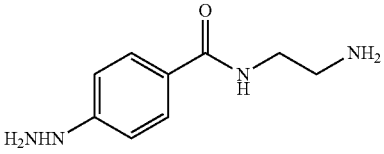 | 1.22 mM | 6 |
| 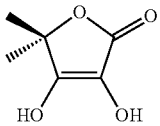 | 0.122 mM | 4 |
| 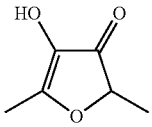 | 1.25 mM | 14 |
| 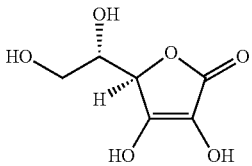 | 122 mM | 50 |
| 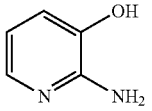 | 0.122 mM | 51 |
| 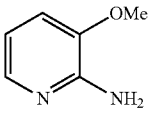 | 0.122 mM | 7 |

TABLE 9-continued
| Test compound, final concentration and S5/S0 | | |
|---|---|---|
| Test Compound | Conc. | S5/S0 |
| 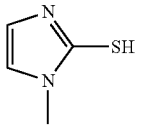 | 36.7 mM | 102 |
| 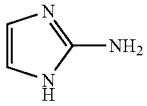 | 24.4 mM | 14 |
| 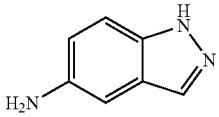 | 12.2 mM | 10 |
| 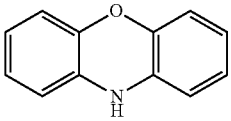 | 0.122 mM | 605 |
| 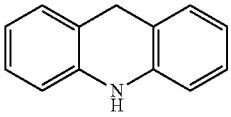 | 0.122 mM | 120 |
| 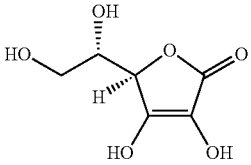 L-Ascorbic Acid | 0.122 mM | 423 |
| acsorbate sodium salt (ascorbate anion) | 0.122 mM | 495 |
| 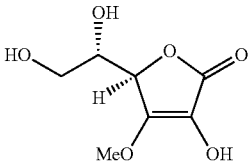 | 122 mM | 16 |
| 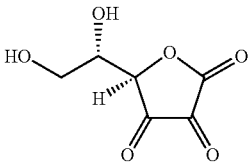 Dehydroascorbic acid | 0.122 mM | 26 |
| 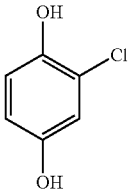 | 0.111 mM | 229 |
TABLE 9-continued
| Test compound, final concentration and S5/S0 | | |
|---|---|---|
| Test Compound | Conc. | S5/S0 |
| 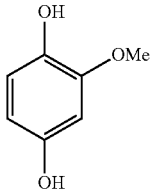 | 0.111 mM | 161 |
| 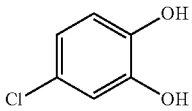 | 0.244 mM | 409 |
| 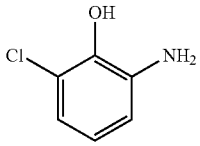 | 0.244 mM | 300 |
| 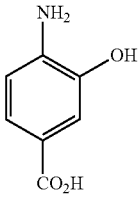 | 0.122 mM | 153 |
| 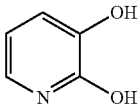 | 0.122 mM | 41 |
| 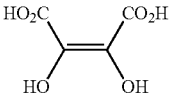 | 0.122 mM | 30 |
| 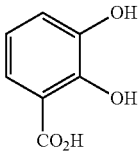 | 0.122 mM | 22 |
| 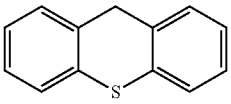 | 0.122 mM | 9 |
| 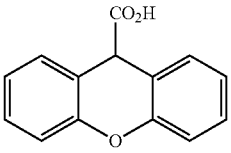 | 0.122 mM | 7 |

TABLE 9-continued

| Test compound, final concentration and S5/S0 | | |
|---|---|---|
| Test Compound | Conc. | S5/S0 |
| 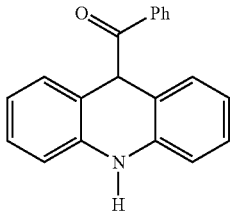 | 0.122 mM | 9 |
| 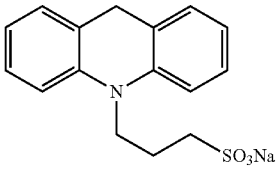 | 0.244 mM | 15 |
| 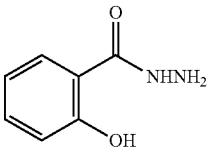 | 0.061 mM | 23 |
| 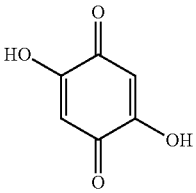 | 0.244 mM | 14 |
| 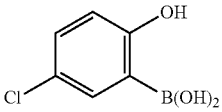 | 0.244 mM | 22 |
| 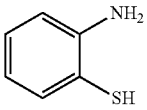 | 0.122 mM | 234 |
| DTT | 72 uM | 20 |
| NH2NH2 | 244 uM | 15 |
| Na2SO3 | 15 uM | 59 |
| Ethylene glycol | 122 uM | 14 |
| 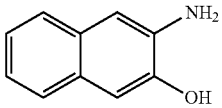 | 0.244 mM | 67 |
| 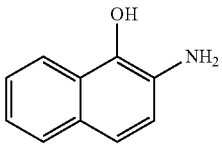 | 0.244 mM | 109 |

TABLE 9-continued

| Test compound, final concentration and S5/S0 | | |
|---|---|---|
| Test Compound | Conc. | S5/S0 |
| 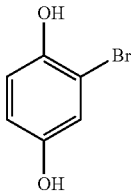 | 0.122 mM | 570 |
| 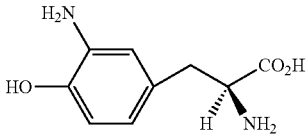 | 0.244 mM | 448 |
| 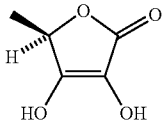 | 0.122 mM | 423 |
| 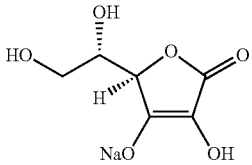 | 122 μM | 9.2 |
| 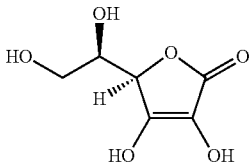 D-Isoascorbic acid | 122 μM | 10.3 |

B. Model System for Selection of Effective Selective Signal Inhibiting Agent (SSIA)

A model system was also developed and employed to screen and select compounds with characteristics to function as selective signal inhibiting agent in assays of the present disclosure. The model system uses a microparticle conjugated to BSA (bovine serum albumin) labeled with a streptavidin and acridan ketenedithioacetal chemiluminescent label (AK1) as the chemiluminescent-labeled sbp, and biotinylated HRP as the activator-labeled specific binding pair. In the model system, varying amounts of Btn-HRP is added to the chemiluminescent-labeled specific binding pair at 0, 1, 10, 100 and 250 ng/mL. Additional unlabeled HRP is added to reach a total HRP of concentration of 500 ng/mL in each reaction mixture. The unlabeled HRP in combination with the activator-labeled sbp was provided to the chemiluminescent-labeled sbp microparticles to emulate sample. A compound for assessment as an SSIA was also added. This reaction mixture of the model system is then triggered by addition of trigger solution in a manner of assays of the present disclosure.

C. Preparation of Materials for Model System:

To prepare the chemiluminescent-labeled sbp on microparticles, Bovine Serum Albumin (BSA) was biotinylated with 4× molar excess of biotin-LC-sulfoNHS (Pierce Biotechnology Inc., Rockford, Ill., USA). Unbound reactants were removed via desalting or dialysis. The biotin-BSA was then reacted with a 5× molar excess of an NHS ester of acridan ketenedithioacetal AK1 in 20 mM sodium phosphate pH 7.2: DMSO 75:25, v/v) followed by desalting in the same buffer. The dual labeled (biotin and AK1) BSA was then coupled with tosyl activated M280 microparticles (Invitrogen Corporation, Carlsbad, Calif., USA) in a 0.1M borate buffer pH 9.5 at a concentration of about 20 μg of labeled BSA per mg of microparticles for 16-24 h at 40° C. After coupling the microparticles were stripped for 1 h at 40° C. with 0.2 M TRIS base, 2% SDS, pH~11. The stripping process was repeated one additional time. Microparticles were then suspended in a 0.1% BSA/TRIS buffered saline (BSA/TBS) buffer and streptavidin (SA) was added at approximately 15 μg SA per mg microparticles. Streptavidin was mixed with the microparticles for 45-50 min at room temperature. The microparticles were then washed three times and suspended in the same BSA/TBS. The load of these microparticles is 5 μg of biotinylated protein per mg of microparticles.

HRP, (Roche Diagnostics, Indianapolis, Ind., USA) was biotinylated with 4× molar excess of biotin-LC-sulfoNHS (Pierce Biotechnology Inc., Rockford, Ill., USA). Alternatively, 25× molar excess of biotin-PEO4-NHS may be used. Unbound reactants were removed via desalting or dialysis.

Each SSIA compound for assessment was solubilized in Buffer II at a concentration at least 10× of the working strength concentration.

D. Testing Procedure Using Model System

25 μl of 1 mg/ml of dual-labeled (biotin and AK1) BSA M280 particles were mixed with 45 μl of working concentration SSIA in Buffer II. The assay volume brought to 85 μl by adding 15 μl of Buffer II. 15 μl of sample containing Btn-HRP:HRP at different ratios (The amount of biotinylated-HRP varied from 0, 1, 10, 100 and 250 ng/mL) was added. The reaction mixture was incubated for 30 min at 37° C., then 100 μL of trigger solution was added and the light intensity recorded. Total volume of reaction mixture, including trigger solution was 200 μL with a final concentration of 100 μM of SSIA.

TABLE 10

| | Compound tested for effectiveness as SSIA | | | |
|---|---|---|---|---|
| | Buffer II Control | 2-amino phenol | 4-Amino-3-hydroxy-benzoic acid | 4-aminoresorcinol hydrochloride |
| BTN-HRP0 | 15,901 | 65 | 972 | 675 |
| BTN-HRP1 | 46,464 | 356 | 2,808 | 1,163 |
| BTN-HRP10 | 2,035,193 | 8,632 | 441,455 | 74,764 |
| BTN-HRP100 | 5,755,341 | 2,092,703 | 5,906,521 | 330,056 |
| BTN-HRP250 | 6,255,297 | 4,008,689 | 6,403,425 | 259,541 |
| S/S0 | 1.0 | 1.0 | 1.0 | 1.0 |
| S1/S0 | 2.9 | 5.5 | 2.9 | 1.7 |
| S2/S0 | 128.0 | 132.8 | 454.2 | 110.8 |
| S3/S0 | 361.9 | 32195.4 | 6076.7 | 489.0 |
| S4/S0 | 393.4 | 61672.1 | 6587.9 | 384.5 |
| | Buffer II Control | 4-chloro catechol | 2-chloro-1,4-dihydroxybenzene | Ascorbic Acid |
| BTN-HRP0 | 16,161 | 93 | 3,571 | 97 |
| BTN-HRP1 | 43,300 | 205 | 4,007 | 757 |
| BTN-HRP10 | 1,769,373 | 1,373 | 188,920 | 16,641 |
| BTN-HRP100 | 6,027,591 | 456,707 | 610,053 | 3,692,291 |
| BTN-HRP250 | 6,162,340 | 1,260,937 | 875,831 | 6,036,145 |
| S/S0 | 1.0 | 1.0 | 1.0 | 1.0 |
| S1/S0 | 2.7 | 2.2 | 1.1 | 7.8 |
| S2/S0 | 109.5 | 14.8 | 52.9 | 171.6 |
| S3/S0 | 373.0 | 4910.8 | 170.8 | 38064.9 |
| S4/S0 | 381.3 | 13558.5 | 245.3 | 62228.3 |

TABLE 11

| | Buffer II Control | Trolox ® | Ascorbic Acid | Ascorbic Acid 6-palmitate | 5,6iso-propyliene ascorbic acid | (+/−)-alpha-Tocopherol | (+)-gamma-Tocopherol | Uric Acid |
|---|---|---|---|---|---|---|---|---|
| BTN-HRP0 | 23,603 | 173 | 151 | 81 | 264 | 2,772 | 6,051 | 5,532 |
| BTN-HRP1 | 45,016 | 1,460 | 995 | 327 | 961 | 6,468 | 10,924 | 9,760 |
| BTN-HRP10 | 2,149,712 | 37,291 | 32,568 | 40,863 | 29,645 | 1,253,187 | 1,686,079 | 1,025,209 |
| BTN-HRP100 | 8,926,151 | 7,251,008 | 4,553,473 | 8,187,204 | 4,917,499 | 8,560,469 | 8,698,069 | 8,712,328 |
| BTN-HRP250 | 9,660,668 | 10,794,247 | 8,915,869 | 10,182,411 | 8,784,595 | 9,628,184 | 10,282,504 | 10,708,733 |
| S/S0 | 1 | 1 | 1 | 1 | 1 | 1 | 1 | 1 |
| S1/S0 | 1.9 | 8.4 | 6.6 | 4 | 3.6 | 2.3 | 1.8 | 1.8 |
| S2/S0 | 91.1 | 215.1 | 216.2 | 502.4 | 112.3 | 452.1 | 278.7 | 185.3 |
| S3/S0 | 378.2 | 41832.7 | 30222.2 | 100662.3 | 18626.9 | 3088.2 | 1437.5 | 1574.9 |
| S4/S0 | 409.3 | 62274.5 | 59176.1 | 125193.6 | 33275 | 3473.4 | 1699.4 | 1935.8 |

| | Buffer II Control | Ferulic acid | Syringic Acid | G.W.7.35 |
|---|---|---|---|---|
| BTN-HRP0 | 27,659 | 5,252 | 14,485 | 67,556 |
| BTN-HRP1 | 56,887 | 12,079 | 23,707 | 92,403 |

TABLE 11-continued

| | | | | |
|---|---|---|---|---|
| BTN-HRP10 | 1,929,315 | 715,313 | 939,372 | 1,600,767 |
| BTN-HRP100 | 8,598,556 | 8,785,865 | 7,927,096 | 7,938,477 |
| BTN-HRP250 | 9,255,947 | 10,244,269 | 9,530,979 | 9,509,801 |
| S/S0 | 1 | 1 | 1 | 1 |
| S1/S0 | 2.1 | 2.3 | 1.6 | 1.4 |
| S2/S0 | 69.8 | 136.2 | 64.8 | 23.7 |
| S3/S0 | 310.9 | 1672.9 | 547.2 | 117.5 |
| S4/S0 | 334.6 | 1950.5 | 658 | 140.8 |

TABLE 12

| | Control | Glutathione | Cysteine | Lipoic Acid |
|---|---|---|---|---|
| BTN-HRP0 | 30,493 | 26,977 | 35,695 | 35,016 |
| BTN-HRP1 | 80,841 | 55,719 | 58,203 | 71,751 |
| BTN-HRP10 | 2,489,892 | 2,480,764 | 2,483,411 | 2,450,949 |
| BTN-HRP100 | 8,931,915 | 8,733,068 | 9,147,371 | 8,647,037 |
| BTN-HRP250 | 9,246,768 | 9,965,235 | 10,190,505 | 8,847,921 |
| S/S0 | 1 | 1 | 1 | 1 |
| S1/S0 | 2.7 | 2.1 | 1.6 | 2 |
| S2/S0 | 81.7 | 92 | 69.6 | 70.0 |
| S3/S0 | 292.9 | 323.7 | 256.3 | 246.9 |
| S4/S0 | 303.2 | 369.4 | 285.5 | 252.7 |

| | Control | Resveratrol | Melatonin | N-Ac-Cysteine | TEMPOL | Nicotinic Hydrazide |
|---|---|---|---|---|---|---|
| BTN-HRP0 | 30,108 | 64,051 | 54,528 | 43,647 | 22,621 | 42,260 |
| BTN-HRP1 | 52,680 | 81,452 | 70,741 | 47,636 | 33,873 | 58,356 |
| BTN-HRP10 | 2,307,964 | 1,073,968 | 2,381,361 | 1,757,607 | 1,963,369 | 2,106,471 |
| BTN-HRP100 | 8,866,105 | 5,944,792 | 9,471,431 | 8,685,795 | 9,220,799 | 8,205,320 |
| BTN-HRP250 | 9,055,791 | 6,559,359 | 10,370,061 | 10,219,869 | 10,578,104 | 7,923,092 |
| S/S0 | 1 | 1 | 1 | 1 | 1 | 1 |
| S1/S0 | 1.7 | 1.3 | 1.3 | 1.1 | 1.5 | 1.4 |
| S2/S0 | 76.7 | 16.8 | 43.7 | 40.3 | 86.8 | 49.8 |
| S3/S0 | 294.5 | 92.8 | 173.7 | 199 | 407.6 | 194.2 |
| S4/S0 | 300.8 | 102.4 | 190.2 | 234.2 | 467.6 | 187.5 |

| | Control | Toco-PEG | Acrylamide/bis-acrylamide 19:1 | Acrylamide/bis-acrylamide 37.5:1 | Nicotinic Acid |
|---|---|---|---|---|---|
| BTN-HRP0 | 30,608 | 33,836 | 28,760 | 36,028 | 34,369 |
| BTN-HRP1 | 144,936 | 44,180 | 50,829 | 56,267 | 53,765 |
| BTN-HRP10 | 2,255,845 | 1,970,753 | 2,286,095 | 2,187,617 | 2,228,317 |
| BTN-HRP100 | 8,581,227 | 8,352,891 | 8,216,691 | 8,094,544 | 8,772,523 |
| BTN-HRP250 | 9,183,040 | 9,383,395 | 8,629,933 | 8,463,999 | 9,224,439 |
| S/S0 | 1 | 1 | 1 | 1 | 1 |
| S1/S0 | 1.5 | 1.3 | 1.8 | 1.6 | 1.6 |
| S2/S0 | 73.7 | 58.2 | 79.5 | 60.7 | 64.8 |
| S3/S0 | 280.4 | 246.9 | 285.7 | 224.7 | 255.2 |
| S4/S0 | 300 | 277.3 | 300.1 | 234.9 | 268.4 |

Compounds demonstrating utility as SSIA for use in assays of the present disclosure include: Ascorbic Acid, 6-palmitate and 5,6-isopropylidene derivatives of Ascorbic acid, 2-aminophenol, 4-Amino-3-hydroxy-benzoic acid, 4-chlorocatechol and TROLOX, a derivative of Tocopherol, with reductions in background signal indicated by comparing S0 values to the control, and improvements in signal to noise demonstrated by increasing S1/S0 values.

Compounds that have shown insufficient effectiveness as SSIA's in the model system are: glutathione, cysteine, N-acetyl cysteine, lipoic acid (a disulfide), pegylated tocopherol, melatonin (a tryptamine derivative), TEMPOL (a stable nitroxide), nicotinic hydrazide, nicotinic acid, Resveratrol and two acrylamide/bis-acrylamide solutions. A second grouping of compounds, including alpha and gamma-Tocopherol, uric acid, and ferulic acid show a reduction in S0 signal in the range of 75-88%, but do not show an increase in S/S0 until the third cal level at 10 ng/mL Btn-HRP.

The screening tests were performed using a modified DxI® Immunoassay System (Beckman Coulter, Inc. Brea, Calif.) as described above.

Example 2

The following example demonstrated immunoassay of an analyte in the absence of solid phase, both in the presence and absence of SSIA. The assay included two direct-labeled antibodies, each of which has specific binding affinity for the analyte, in this Example, Prostate Specific Antigen (PSA). One antibody, designated "Ab1" for convenience, is covalently attached to one or more molecules, typically two molecules, of AK11. A second antibody, designated "Ab2", is covalently bonded to HRP. The preparation of the materials, performance of the assay and results were as described below.

A. Preparation of Ab1~AK Conjugate

In the following example, an NHS ester of an acridan ketenedithioacetal chemiluminescent compound, referred to herein as AK1 (shown above) is covalently attached to an antibody of prostate specific antigen (PSA). The following method may also be employed to prepare chemiluminescent labeled antibodies of other antigens or other acridan ketenedithioacetal chemiluminescent compounds.

AK1, an amine reactive acridan ketenedithioacetal chemiluminescent compound was prepared in DMSO at 10 mM. To 3 mg (6.6 mg/mL) of a monoclonal PSA antibody in PBS, pH 7.4, a 10-fold molar excess of AK1 was added and incubated in the dark for 1 hour at ambient temperature. The product was purified over a PD-10 desalting column, equilibrated in PBS, pH 7.4. The product contained monoclonal anti-PSA covalently attached to AK11 (reaction product of AK1), shown below with bond to the antibody indicated by wavy line, at available amino groups on the antibody. The absorbance measurements at 280 and 384 nm were used to determine the IgG concentration and the AK11/IgG ratio (3 AK11:1 IgG).

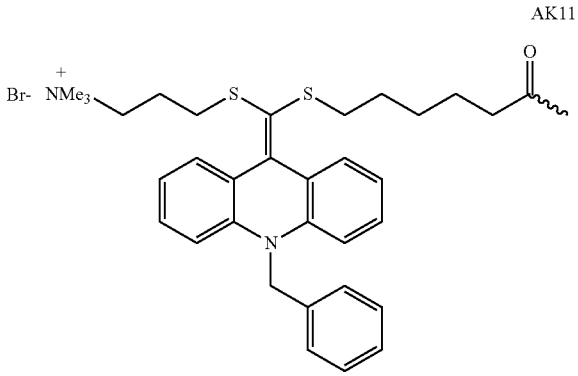

B. Preparation of Ab-2~HRP Conjugate

In the following representative synthetic procedure, the enzyme horseradish peroxidase (HRP) is covalently attached to an antibody to the prostate specific antigen (PSA). Following the method taught herein, additional enzyme-labeled antibodies can be prepared.

C. Activation of HRP 10 mg of HRP (Roche, 10-814-393-001) was dissolved in 2.0 mL of 1×PBS (137 mM NaCl, 10 mM Phosphate, 2.7 mM KCl, and a pH of 7.4). A 30-fold molar excess of sulfo-SMCC (Thermo Fisher Scientific, Waltham, Mass.) in DMSO (25 ug/uL) was added to the HRP solution and incubated in the dark for 1 hour. The maleimide activated HRP was purified over a PD-10 desalting column (GE Healthcare, Piscataway, N.J.) in PBS, pH 7.4. The HRP concentration was determined spectrophotometrically, using an extinction coefficient of 2.275 mL/mg-cm at 403 nm.

D. Activation of Anti-PSA Monoclonal Antibody (Ab2)

A 50-fold molar excess of 2-iminothiolane (Thermo Fisher Scientific, Piscataway, N.J.) was added to monoclonal PSA antibody in PBS, pH 7.4 and reacted at ambient temperature for 1 hour in the dark. The monoclonal PSA antibody, designated Ab2, differs from Ab1 in Example 2 in binding site on PSA. The thiolated antibody was purified over a PD-10 desalting column (GE Healthcare, Piscataway, N.J.) in PBS, pH 7.4. The antibody concentration was determined spectrophotometrically using an extinction coefficient of 1.4 mL/mg-cm at 280 nm.

E. Preparation of Ab2-HRP Conjugate

A 5-fold excess of activated-HRP was added to the activated-Ab2 solution to create a conjugate reaction mixture. The conjugate reaction mixture was incubated on a rotator at room temperature for 2 hours in the dark. The unreacted thiol and maleimide groups were blocked by sequential additions of an excess amount of L-cysteine and iodoacetamide (15 minutes each step) to the conjugate reaction mixture. In the first step, an excess (0.025× reaction volume) of 50 mg/mL L-cysteine-HCl (dissolved in PBS, pH 7.4) was added and incubated 15 minutes. In the second step, an excess (0.04× reaction volume) of 50 mg/mL iodoacetamide (dissolved in PBS, pH 7.4) was added to the reaction mixture together with 50 mM Borate, pH 8.5 (0.08× reaction volume) and incubated for an additional 15 minutes at ambient temperature protected from light. The conjugate was purified over a Superdex 200 column (GE Healthcare, Piscataway, N.J., Part No. 17-5175-01) equilibrated in PBS, pH 7.4. The fractions containing the conjugate were pooled and the HRP/IgG ratio was determined spectrophotometrically, as described in A and B. The calculated HRP/IgG ratio was 1.4.

Assay of PSA with Direct-Labeled sbp's with SSIA

The Ab1-AK11 conjugate was provided in PBS, pH 7.4 at 10 μg/ml. The Ab2-HRP conjugate was provided in PBS, pH 7.4 at 0.25 μg/ml. In a first reaction vessel 25 μl of Ab1-AK11 conjugate, 600 μM Ascorbic acid in deionized water, and 25 μl of Ab2-HRP conjugate are added to 25 μl of sample and incubated for 15 minutes. For comparison without SSIA, in a second reaction vessel, 25 μl of Ab1-AK11 conjugate, 25 μl of water, 25 μl of Ab2-HRP conjugate were added to 25 μl of sample and incubated for 15 minutes.

Following incubation, the chemiluminescent reaction is initiated in each reaction vessel by injection of 100 μl of trigger solution A. Concurrent with injection of the trigger solution into the reaction vessel, the chemiluminescent signal was detected by a luminometer incorporating a photon-counting photomultiplier tube (PMT). Signal collection continued over the course of 3.85 seconds and the chemiluminescent signal data stored in a computer.

Each sample was analyzed according to the above assay method in triplicate. The RLU data collected for each assayed sample during the time interval of 495 milliseconds starting 125 milliseconds from start of trigger solution introduction into the reaction vessel was summed for each individual run, averaged over the triplicates for each sample and presented in Table 13. A ratio of signal to noise (S/S0) was calculated at each concentration value. The data in Table 13 may be used to generate a calibration curve for analysis of samples of unknown PSA concentration.

TABLE 13

| | Without SSIA | | With SSIA | |
|---|---|---|---|---|
| PSA, ng/mL | RLU | S/S0 | RLU | S/S0 |
| 0.0 | 14388 | 1.0 | 180 | 1.0 |
| 0.4 | 9583 | 0.7 | 324 | 1.8 |
| 1.4 | 12980 | 0.9 | 755 | 4.2 |
| 7.0 | 13253 | 0.9 | 3032 | 16.8 |
| 51.0 | 28872 | 2.0 | 16373 | 91.0 |
| 101.6 | 36737 | 2.6 | 23119 | 128.4 |

The following example demonstrated immunoassay according to the present disclosure of an analyte using direct-labeled antibodies in the absence of solid phase, both in the presence and absence of SSIA. From the results shown in Table 13, the direct-labeled antibody assay without SSIA is not (analyte) dose responsive across the full range of PSA concentrations assayed, with. In contrast, the direct-labeled immunoassay incorporating SSIA according to the present disclosure is functional, providing dose response from zero (control) through all 5 PSA calibrator values. Consequently, the direct-labeled immunoassay incorporating SSIA could be successfully used to determine unknown analyte concentrations in other samples. Also, the addition of an SSIA improves the signal to noise ratio (S/S0) over the calibration range (PSA, ng/mL from 0 to 101.6).

Example 3. AB1~AK1, AB2~HRP Conjugates Assay for PSA

Assays directed to PSA, using directed-labeled chemiluminescent-labeled sbp and activator-labeled sbp were conducted in solution as described below. This experiment additionally explored the result of employing conjugated reagents with varying degrees of purification.

Mouse anti-PSA (MxPSA) (111 μL, 9 mg/mL) and AK1 NHS ester (106 μL, 1 mg/mL DMF stock) were reacted in 0.1 M borate pH 8.25 buffer (784 μL). The mixture was mixed at room temperature for 90 minutes. 100 μL of the reaction mixture was removed, and 2.6 μL of a lysine solution (2 mg/mL) was added and mixed for 30 minutes. This reaction mixture was diluted in PBS buffer for use in the "unpurified conjugate" assay. Conjugate prepared in the same manner was purified with a desalting column, as known in the art, for use in the "purified conjugate" assay.

30 μL of a MxPSA-AK1 conjugate solution (67 ng), 24 μL of calibrator (0-129 ng/mL PSA), 30 μL of MxPSA-HRP conjugate (7.8 ng), and 36 μL of serum were pipetted into the wells of a white microtiter plate. The plate was incubated for 10 minutes at 37° C. 5 μL of an ascorbic acid solution (5.5 mM) was added. The plate was placed into a injection plate luminometer. 100 μL of trigger solution A was added by the luminometer and the chemiluminescent signal was read for 5 seconds from addition of the trigger solution.

The intensity of chemiluminescent signal (relative luminescent units, RLU) for the reactions of "unpurified" and "purified" MxPSA-AK1 conjugates as a function of the concentration of PSA in the reaction mixture are provided in the table following.

TABLE 14

| [PSA] (ng/mL) | Intensity (RLU) purified | Intensity (RLU) unpurified |
|---|---|---|
| 0 | 1.6 | 1.7 |
| 0.5 | 4.1 | 4 |
| 2 | 10.2 | 9.6 |
| 10.8 | 35.5 | 43.5 |
| 77.2 | 328 | 319 |
| 129 | 485 | 555 |

The data provided in Table 14, when transformed as a log-log plot, showed the log intensity of chemiluminescent signal against the log concentration of PSA was monotonic and approximately linear in the [PSA] range 0.5 ng/mL to 129 ng/mL, irrespective of the level of purification of the MxPSA-AK1 conjugate reagent.

Example 4. Competitive Immunoassay

There are provided homogeneous immunoassays of an analyte utilizing a chemiluminescent-labeled capture antibody in combination with labeled analyte in a competitive immunoassay reaction. The example analyte cyclic-AMP ("cAMP") is conjugated with HRP to provide a cAMP-HRP reagent, which competes for analyte cAMP at the capture antibody ("Capture Ab") which is conjugated with AK5 to form a capture antibody-AK5 complex. Thus, upon formation of the capture antibody-AK5-cAMP-HRP complex and addition of trigger solution as described herein, chemiluminescence (i.e., "Light") can be observed to the extent that the capture antibody-AK5-cAMP-HRP complex is formed. Analyte (cAMP) which is not conjugated with HRP competes for the capture antibody-AK1 complex, and upon addition of trigger solution the resulting capture antibody-AK5-cAMP complex provides no chemiluminescence (i.e., "No Light"). Accordingly, analyte cAMP competes for capture antibody-AK5 complex and thereby suppresses signal due to the capture antibody-AK1-cAMP-HRP complex.

Rabbit anti cAMP (IMMUNOTECH, Marseille) 0.1 mg (20.3 uL from 4.93 mg/mL stock) was added to 162 uL of 0.1 M sodium borate pH 8.25 buffer in 1.7 mL centrifuge tube. 17.6 ug of AK5 (17.6 ul from 1 mg/mL stock of DMF) was added. After quick vortex mixing tube was placed on a rotating shaker for 1 hour at room temperature. Reaction was quenched by adding 1.2 uL of L-lysine from 3 mg/mL stock. Reaction mixture was diluted (1:1) in 0.4% BSA and PBS and stored at 4 C. cAMP-HRP was prepared according to the literature. See e.g., J Immunological Methods, 1992, 155 31-40. cAMP was purchased from Sigma, St. Louis, Mo. A 30 nM stock of cAMP was prepared in PBS and further diluted in PBS to make sample calibrators for the assay. See Table 15.

The competitive immunoassay protocol was as follows. AK5 labeled monoclonal Rabbit anti cAMP (0.275 ug/mL) (3 uL), HRP labeled cAMP (0.09375 ug/mL) (3 ul) and cAMP calibrators (4 ul) were added into a white polystyrene 384 low volume plate. Conjugate solutions were 0.2% in BSA. After incubation of 30 minutes at room temperature, 1 ul of 2-aminophenol (0.6875 mM) was added followed by a trigger solution (10 ul). The trigger solution contained 25 mM Tris pH 8, 8 mM p-hydroxycinnamic acid, 1 mM EDTA, 0.2% Tween-20 and 0.1 M ureaperoxide. Light intensity was measured (Spectromax) for one second immediately upon injection of trigger. Reactants were not exposed to light during incubation and were not shaken.

As shown in Table 15 following, calibrators were used in the range from 0.137 nM to 10000 nM. The data are provided in Table 15, for which the $IC_{50}$ for cAMP was calculated to be 2.6 nM. The data demonstrate that complete suppression of the chemiluminescent signal can be achieved with analyte cAMP levels in excess of 100 nM.

TABLE 15

Competition immunoassay for cAMP

| nM | Average | Signal Suppression |
|---|---|---|
| 0 | 91646 | 0% |
| 0.137 | 89089 | 3% |
| 0.412 | 83377 | 9% |
| 1.23 | 66207 | 28% |
| 3.7 | 31156 | 66% |
| 11.1 | 4576 | 95% |
| 33.3 | 943 | 99% |
| 100 | 315 | 100% |
| 1000 | 173 | 100% |
| 10000 | 167 | 100% |

Example 5. Preparation of Chemiluminescent-Labeled SBP Including Chemiluminescent Label, Biotinylated BSA, Neutravidin and Antibody This example describes "tetramer" scaffolds or complexes formed by self-assembly through non-covalent interaction of biotin and streptavidin. The example also demonstrates immunoassays for an analyte using the tetramer scaffold.

A. Labeling of BSA with Chemiluminescent Compound and Biotin:

Bovine serum albumin (BSA) labeled with sulfo-NHS-LC-biotin (Thermo Scientific, Rockford Ill.) and AK1-NHS ester (Lumigen, Southfield Mich.) were mixed at a molar ratio of 7 moles of AK1 per mole of BSA; 3 moles of biotin per mole of BSA), and the mixture was purified over a PD-10 desalting column as described in Example 17.

B. Preparation of Neutravidin-IgG Conjugate

The thiolated anti-PSA monoclonal antibody was prepared as described in Example 2.

A 3-fold molar excess of maleimide-activated neutravidin (Thermo Scientific) was added to the thiolated monoclonal anti-PSA solution (5 mg) and incubated on a rotator at room temperature for one hour in the dark. The unreacted thiol and maleimide groups were blocked by sequential additions of L-cysteine and iodoacetamide (15 minutes each step) to the conjugate reaction mixture. The conjugate was purified over a Superdex® 200 column (GE Healthcare, Piscataway N.J.), and equilibrated in PBS, pH 7.4, to remove unreacted neutravidin. HPLC fractions containing the conjugate were pooled and used in preparation of the tetramer scaffold complexes.

C. Preparation of Scaffold Complexes Containing Neutravidin Conjugated IgG and Labeled BSA A 3-fold molar excess of labeled BSA, as described above, was added to the neutravidin-conjugated IgG and complexes were allowed to form for 30 minutes at ambient temperature. The final product was purified by HPLC as described above, and the products were stored at 4° C. until further use.

D. PSA Immunoassay with Tetramer Scaffold

The immunoassay for PSA was performed substantially as described in Example 2. Briefly, equal volumes (25 uL each) of the tetramer scaffold, HRP conjugate, 600 μM ascorbic acid and PSA sample were combined in a reaction vessel and incubated at 37° C. for 15 minutes. Following incubation, a chemiluminescent reaction was initiated by injection of 100 μL of trigger solution A into the reaction vessel. Concurrent with the injection, the chemiluminescent signal was detected by a luminometer incorporating a photomultiplier tube (PMT) over the course of 275 milliseconds and the data stored in a computer.

Samples of known PSA concentration were prepared as described previously to reach PSA concentrations provided in Table 16. The samples were then analyzed as described above, and the data was used to generate a calibration curve for analysis of samples of unknown PSA concentration.

TABLE 16

| | Anti-PSA-neutravidin-Biotin-BSA-AK1 Scaffold | | | | |
|---|---|---|---|---|---|
| Immunoreaction Concentrations | | | | | |
| Scaffold (μg/mL IgG) | 0.05 | 0.2 | 0.5 | 2 | 5 |

TABLE 16-continued

| | Anti-PSA-neutravidin-Biotin-BSA-AK1 Scaffold | | | | |
|---|---|---|---|---|---|
| anti-PSA~HRP (μg/mL) | 0.5 | 0.5 | 0.5 | 0.5 | 0.5 |
| Ascorbic acid (μM) | 600 | 600 | 600 | 600 | 600 |
| | RLU (Average over 275 ms) | | | | |
| [PSA] (ng/mL) | | | | | |
| 0.0 | 40 | 55 | 72 | 81 | 139 |
| 0.4 | 93 | 180 | 357 | 616 | 777 |
| 1.4 | 281 | 747 | 1,456 | 2,245 | 2,469 |
| 7.0 | 3,085 | 8,983 | 14,819 | 16,717 | 13,931 |
| 51.0 | 43,316 | 153,325 | 302,112 | 467,243 | 279,741 |
| 101.6 | 59,096 | 210,419 | 445,267 | 933,172 | 792,293 |
| | Signal/Noise Ratio | | | | |
| 0.0 | 1.00 | 1.00 | 1.00 | 1.00 | 1.00 |
| 0.4 | 2.33 | 3.29 | 4.96 | 7.57 | 5.61 |
| 1.4 | 7.03 | 13.66 | 20.22 | 27.61 | 17.81 |
| 7.0 | 77.13 | 164.32 | 205.81 | 205.54 | 100.46 |
| 51.0 | 1082.90 | 2804.73 | 4196.00 | 5744.79 | 2017.37 |
| 101.6 | 1477.40 | 3849.12 | 6184.26 | 11473.43 | 5713.65 |

Example 6. Preparation of Chemiluminescent-Labeled Auxillary, Biotinylated Antibody and Self-Assembled Streptavidin-IGG Polymer In this example, AK1-labeled streptavidin was mixed with a biotinylated antibody, thereby forming polymers by self-assembly. These self-assembled streptavidin/biotin-IgG polymers can be used as scaffolds for immunoassay of an analyte.

A. Preparation of AK1-Labeled Streptavidin

AK1 (Lumigen, Southfield, Mich.) was dissolved in anhydrous DMSO at a concentration of 30 mg/mL. Six (6) molar equivalents were added to a 10.1 mg/mL solution of streptavidin (Streptavidin-Plus®, Prozyme, San Leandro, Calif.) prepared in water containing 50 mM NaCl. The reaction was allowed to proceed in the dark for 60 minutes and subsequently purified by size exclusion chromatography using a Sephadex® G-25 column (GE Healthcare, Piscataway N.J.) equilibrated with PBS, pH 7.2. The AK11:protein molar ratio was determined by UV spectroscopy using the following equations:

$$[AK11]=A384/11{,}380\ cm\text{-}1M\text{-}1$$

$$[streptavidin]=(A280-(A384/(A384/A280\ AK1)))/176{,}000\ cm\text{-}1M\text{-}1$$

The second equation was used to correct for the absorbance of AK1 at 280 nm. Under these conditions, an AK11:streptavidin molar ratio of 4.3 AK1 per streptavidin was achieved with a yield of 94%.

Preparation of AK11-Labeled Anti-cTnI Monoclonal Antibody

AK-1 labeled antibody was prepared as described in example 2, except a 15-fold molar excess of AK-1 to IgG was used to prepare the direct labeled IgG.

B. Preparation of Biotinylated Anti-cTnI Monoclonal Antibodies

A 10-fold molar excess of NHS-LC-biotin (Thermo Scientific, Rockford Ill.) was added to anti-cTnI monoclonal antibody, and the mixture was incubated at room temperature for 2 hours. The biotinylated antibody was purified by dialysis in PBS, pH 7.2. The biotin:antibody molar ratio was 4.9, as determined using the commercial biotin quantitation kit (Thermo Scientific)

C. Preparation of Self-Assembled Polymer Scaffold

The self-assembled polymer was prepared by adding 2 molar equivalents of biotinylated cTnI antibody to 1 molar equivalent of AK11-labeled streptavidin. The mixture was incubated at ambient temperature in the dark for 90 minutes to allow the complexes to form. The reaction mixture was purified over a Superdex® 200 column as described in Example 3. The HPLC fractions corresponding to the high molecular weight (800 kDa->1.5 MDa) conjugate were pooled and stored at 4 degrees C. until use.

D. Immunoassay for cTnI

The immunoassay for cTnI was performed as follows. 25 μL each of the self-assembled polymer scaffold, or direct labeled antibody as the control, HRP conjugate, 600 μM ascorbic acid and sample were mixed in a reaction vessel, and incubated for 15 minutes. Following incubation, the chemiluminescence reaction was initiated by injection of 100 μL of trigger solution A into the reaction vessel. Concurrent with injection of the trigger solution into the reaction vessel, the chemiluminescent signal was detected by a luminometer incorporating a photon-counting photomultiplier tube (PMT) over the course of 275 milliseconds, and the data is stored in a computer.

cTnI samples of known concentration were prepared by adding known quantities of native cTnI to normal human serum to reach the cTnI concentrations indicated in Table 17. Each sample was analyzed in triplicate according to the method described above (and in Example 4 for immunoassay of PSA). The RLU data collected for each assayed sample over a given time interval was summed for each individual run and averaged over the triplicates for each sample. A ratio of signal-to-noise was determined for samples at each known concentration.

TABLE 17

| [cTnI], ng/mL | acridan labeled IgG (Control) | SA-IgG Self-Assembling Scaffold | % Control |
|---|---|---|---|
| | Average RLU | | |
| 190 | 3,757,770 | 92,017,724 | 2449% |
| 41 | 1,326,964 | 20,703,152 | 1560% |
| 9.2 | 380,904 | 3,414,677 | 896% |
| 2.3 | 101,228 | 628,395 | 621% |
| 0.82 | 41,548 | 210,780 | 507% |
| 0.22 | 17,520 | 67,552 | 386% |
| 0.1 | 12,871 | 32,802 | 255% |
| 0 | 9,966 | 16,183 | 162% |
| | Signal/Noise Ratio | | |
| 190 | 377.07 | 5685.99 | 1508% |
| 41 | 133.15 | 1279.30 | 961% |
| 9.2 | 38.22 | 211.00 | 552% |
| 2.3 | 10.16 | 38.83 | 382% |
| 0.82 | 4.17 | 13.02 | 312% |
| 0.22 | 1.76 | 4.17 | 237% |
| 0.1 | 1.29 | 2.03 | 157% |
| 0 | 1.00 | 1.00 | 100% |

The data in Table 17 illustrated successful dose response for immunoassay of analyte TnI concentrations from 0 to 190 ng/ml for both an assay formats. The results of Example 6 also showed increase in signal intensity (shown by average RLU) and improvement in signal to noise (S/S0) for the assay utilizing self-assembled streptavidin/biotin-IgG (antibody) polymers as compared to antibody direct-labeled with acridan.

Example 7. Preparation of Chemiluminescent-Labeled SBP Including Chemiluminescent Label, KLH, and Streptavidin-Biotin-Coupled Antibody This example demonstrates the use of keyhole limpet hemocyanin (KLH) in the preparation of a large polymer scaffold. Maleimide-activated KLH is conjugated with antibody and labeled with AK1 to form the scaffold. This example also demonstrates the use of such scaffolds in immunoassays for an analyte.

A. Thiolation of cTnI Monoclonal Antibodies

Monoclonal anti-cTnI was thiolated by adding 50 mM N-acetyl homocysteine lactone (AHTL) (Sigma-Aldrich, St. Louis Mo.) to the antibody at pH 9.0, and allowing the mixture to react for 1 hour at room temperature. The thiolated antibody was purified using a PD-10 desalting column, as described in example 2.

B. Preparation and Labeling of KLH Scaffold 3.4 mg of thiolated anti-cTnI was added to 10 mg of maleimide-activated KLH (product #77605, ThermoScientific) and the resulting solution was incubated at room temperature for 2 hours. To label the antibody-KLH conjugate, 0.9 mg of AK1-NHS ester, dissolved in 0.7 mL DMSO, was added to the solution and allowed to react for 15 minutes. The conjugate was then purified by buffer exchange (20 mM phosphate, 1 mM EDTA) using a 30 kDa MWCO Ultracell centrifugal concentrator (Millipore, Billerica Mass.).

C. Immunoassay with Large Protein KLH Scaffold

An immunoassay for cTnI using the large protein KLH scaffold was performed as described in Example 6. Samples of known cTnI concentration were prepared as described in Example 6. Briefly, equal volumes (25 μL) of the KLH scaffold at 10 ug/mL (normalized to IgG concentration), 1 ug/mL, HRP conjugate, 600 mM ascorbic acid in water and sample were mixed together in a reaction vessel. The mixture was incubated with 100 μL of trigger solution A (i.e. a trigger solution) to initiate the chemiluminescent reaction. After initiation of the chemiluminescent reaction, the samples were read on a SpectraMax® L microplate luminometer in the fast read kinetic mode, and chemiluminescent signal was recorded over a time period of about 0.12 to 0.21 seconds. Results of the immunoassay are shown in Table 18.

TABLE 18

| [cTnI], ng/mL | Average RLU |
|---|---|
| 0 | 20,675 |
| 0.1 | 61,589 |
| 25.0 | 32,757,125 |

Example 8. Preparation of Chemiluminescent-Labeled SBP Including Chemiluminescent Label, Streptavidin Microparticle and Biotinylated Antibody This example describes preparation of protein microparticles from AK1-labeled streptavidin by desolvation. After coupling with a biotinylated antibody, the streptravidin particle can be used as a scaffold for immunoassays.

A. Preparation of Protein Microparticles

AK1-labeled streptavidin was prepared as described in Example 6. 9.8 mg (2 mL) of the AK1-labeled streptavidin was added to a 4 mL glass reaction vial and stirred at a constant rate of 350 rpm using a Teflon stir bar. 2.8 mL of absolute ethanol (Sigma-Aldrich, St. Louis Mo.) was then added drop-wise at a rate of 2 mL/minute until the solution became turbid. 12 μL of a 5% glutaraldehyde solution (Sigma-Aldrich; diluted 1:10 in distilled water) were then added to the reaction and mixed for an additional 60 minutes to crosslink the streptavidin subunits of the particles formed by desolvation. The molar amount of glutaraldehyde was equal to the number of lysine residues present in 9.8 mg of streptavidin. 12 μL of an aqueous 0.832M ethanolamine solution (Sigma-Aldrich) were then added to quench the reaction, followed by the addition of 2.80 μL of a 20% aqueous Tween®-20 solution to stabilize the particles.

The particles were placed into a Slide-A-Lyzer dialysis cassette (Thermo Scientific, Rockford, Ill.) and dialyzed against PBS, pH 7.4 containing 0.01% Tween-20 at 4° C. The dialysis buffer (1 L) was exchanged twice over a 24-hour period to remove reaction by-products. The streptavidin concentration of the particle solution was then measured using a commercial bicinchoninic acid (BCA) protein assay kit (product #23227, ThermoScientific). SA-21 streptavidin (E280=3.2 cm-1 mg/mL-1) was used to prepare standards at known concentrations and the protein concentration of the particles was calculated from the standard or calibration curve.

The purified particles were analyzed by photon correlation spectroscopy using a Delsa™Nano Zeta Potential and Submicron Particle Size Analyzer (Beckman Coulter) and were found to have an average diameter of approximately 4 microns. By varying the conditions described herein (volume of solvent used to desolvate particles, reaction pH, etc) the desired particle size (~200 nm to 4 μm) can be achieved.

B. Assay for cTnI Using Streptavidin Particle

The AK1-labeled streptavidin particles were coated with biotinylated anti-cTnI antibody in PBS at pH 7.4 and ratio of 0.23 mg IgG per mg of the particles. The mixture was incubated at room temperature for 30 minutes with gentle shaking to allow complexing of the biotinylated IgG with the streptavidin particles. The particles were then centrifuged at 10,000×g for 5 minutes, and the supernatant, containing any unbound IgG, was removed. The particle pellet was resuspended in PBS, at pH 7.4 containing 0.1% Tween-20 to a final concentration of 100 μg/mL streptavidin.

A mixture containing 50 μg/mL of streptavidin particles coated with anti-cTnI antibody at a concentration of 0.15 μg/mL, horseradish peroxidase conjugate, 375 μM ascorbic acid and 1 mg/mL IgG (BCI item 270904) was prepared in assay diluent. The assay was performed by adding 70 μL of the HRP conjugate/particle mixture and 30 μL of each sample to a reaction vessel. Samples of known cTnI concentrations were prepared by spiking known quantities of native cTnI (Scipac, Sittingbourne UK) into normal human serum, and sample concentrations were assigned from dose values generated from the AccuTnI assay (Beckman Coulter). Following a 15-minute incubation at room temperature, the samples were read on a SpectraMax® L microplate luminometer (MDS Analytical Technologies) in the fast kinetic read mode. To initiate the chemiluminescent reaction, an equal volume of trigger Solution A was injected at a rate of 350 μL/sec while monitoring the chemiluminescent signal. SoftMax Pro software was utilized to analyze data. Values are reported as the sum of 20 data points (10 ms integration time), beginning 30 ms after the initiation of chemiluminescence, and are shown in Table 19.

TABLE 19

| [cTnI], ng/mL | Average RLU |
|---|---|
| 22.900 | 10,055,867 |
| 5.100 | 2,296,862 |
| 1.290 | 299,171 |
| 0.322 | 180,060 |
| 0.031 | 49,456 |
| 0.000 | 37,747 |

Example 9. Variation of Assay Component Concentrations for Assay of PSA with Chemiluminescent-Labeled SBP Including Dextran Scaffold and SSIA The following examples demonstrate immunoassay of an analyte utilizing a chemiluminescent-labeled sbp including a soluble dextran scaffold direct labeled with chemiluminescent compound and antibody.

In this example, one member of a specific binding pair of monoclonal antibodies for PSA is conjugated to a dextran molecule coupled with AK1, as described in Example 10 below, except the antibody is thiolated and covalently-linked to AK11-labeled and maleimide-activated dextran. The anti-PSA-dextran conjugate was provided in an aqueous solution at 10 μg/ml, 2.5 μg/ml or 0.5 μg/ml as indicated in the tables below. A second monoclonal PSA antibody was conjugated to HRP, as described above and provided in an aqueous solution at either 0.5 μg/ml, 0.1 μg/ml or 0.03 μg/ml as indicated in the tables below.

The assays were performed by placing 25 μl of sample in each of two reaction vessels. To the sample in the first reaction vessel, 25 μl of Ab1 solution, 25 μl of water, 25 μl of Ab2 solution was added and incubated for 15 minutes. In a second reaction vessel 25 μl of Ab1 solution, Ascorbic acid (Sigma, St. Louis, Mo.) in deionized water at the concentrations of 200 or 500 μM (as indicated in the table below), and 25 μl of Ab2 solution were added to 25 μl of sample and incubated for 15 minutes. Following incubation, the chemiluminescent reaction in each reaction vessel was initiated by injection of 100 μl of trigger solution A. Concurrent with injection of the trigger solution into the reaction vessel, the chemiluminescent signal is detected by a luminometer incorporating a photon-counting photomultiplier tube (PMT) over the course of 3.85 seconds and the data stored in a computer.

Each sample was analyzed according to the above assay method in triplicate. The RLU data collected for each assayed sample during the time interval of 495 milliseconds starting 82.5 milliseconds from start of trigger solution introduction into the reaction vessel was summed for each individual run, averaged over the triplicates for each sample and presented in Table 20. A ratio of signal to noise (S/S0) was calculated at each concentration value. The data in Table 20 may be used to generate a calibration curve for analysis of samples of unknown PSA concentration.

Samples of known concentration were prepared as described previously. Each sample was analyzed according to the above method in triplicate.

TABLE 20

| | Without SSIA | | w/SSIA | |
|---|---|---|---|---|
| PSA, ng/mL | RLU | S/S0 | RLU | S/S0 |
| 0.0 | 222449 | 1.0 | 1756 | 1.0 |
| 0.4 | 186876 | 0.8 | 4393 | 2.5 |
| 1.4 | 150945 | 0.7 | 13337 | 7.6 |

TABLE 20-continued

| | Without SSIA | | w/SSIA | |
|---|---|---|---|---|
| PSA, ng/mL | RLU | S/S0 | RLU | S/S0 |
| 7.0 | 243129 | 1.1 | 57119 | 32.5 |
| 51.0 | 946997 | 4.3 | 362044 | 206.2 |
| 101.6 | 1491153 | 6.7 | 604024 | 344.0 |

These next demonstration assays utilize reactants similar to the previous example. One member of a specific binding pair for PSA is conjugated to a dextran molecule coupled with AK1, and provided in an aqueous solution at either 10 μg/ml, 2.5 μg/ml or 0.5 μg/ml as indicated in the tables below. A second monoclonal PSA antibody is conjugated to HRP, as described above and provided in an aqueous solution at either 0.5 μg/ml, 0.1 μg/ml or 0.03 μg/ml as indicated in the tables below.

Each sample was analyzed according to the following method in triplicate.

The assay was performed by placing 25 μl of sample in a reaction vessel, then adding 25 μl of Ab1 solution, ascorbic acid in water at the concentrations of 200 or 500 μM, as indicated in the table below, and 25 μl of Ab2 solution, thereby creating a reaction mixture. Mixing was only by delivery of each reactant, followed by 15 minute incubation. Following incubation, the chemiluminescent reaction is initiated in each reaction vessel by injection of 100 μl of trigger solution A and light generated by the reaction was detected by a photon-counting luminometer for 3.85 seconds and the RLU data stored in a computer.

The RLU data collected for each assayed sample during the time interval of 495 milliseconds starting 125 milliseconds from start of trigger solution introduction into the reaction vessel was summed for each individual run, averaged over the three replicates for each sample and presented in Tables 21-23. A ratio of signal to noise (S/S0) and % CV was calculated at each concentration value. The data in the tables may be used to generate a calibration curve for analysis of samples for determination of PSA concentration utilizing the materials and guidance of this example.

The results of Example 9 demonstrated successful immunoassays are varying chemiluminescent-labeled sbp, activator-labeled sbp, and SSIA concentrations and different ratios of those reactants. The methods of Example 9 are suitable for use in determination of analyte concentration in unknown samples, including the generation of calibration curves for determination of PSA concentration according to standard methods.

TABLE 21

| | | | | | | |
|---|---|---|---|---|---|---|
| | Solution Concentration of each reactant. | | | | | |
| Dextran-Ab1-AK1 ug/mL | 10 | 10 | 10 | 10 | 10 | 10 |
| AB2-HRP conj ug/mL | 0.5 | 0.5 | 0.1 | 0.1 | 0.03 | 0.03 |
| Ascorbic acid uM | 200 | 500 | 200 | 500 | 200 | 500 |
| | Amount in Reaction Vessel | | | | | |
| Capture Ab (ng) | 250 | 250 | 250 | 250 | 250 | 250 |
| HRP-conj (ng) | 12.5 | 12.5 | 2.5 | 2.5 | 0.75 | 0.75 |
| Ascorbic acid Conc uM | 50 | 125 | 50 | 125 | 50 | 125 |
| Ascorbic acid nMoles | 5 | 12.5 | 5 | 12.5 | 5 | 12.5 |
| PSA (ng/mL) | Sum RLU | | | | | |
| 0.0 | 7,713 | 2,224 | 1,633 | 607 | 659 | 305 |
| 0.4 | 10,169 | 3,769 | 2,453 | 1,173 | 1,020 | 543 |
| 1.4 | 19,053 | 9,363 | 5,424 | 3,213 | 1,913 | 1,164 |
| 7.0 | 63,211 | 36,408 | 19,852 | 12,859 | 6,972 | 4,311 |
| 51.0 | 363,729 | 224,620 | 122,425 | 74,771 | 40,588 | 24,837 |
| 101.6 | 683,660 | 403,413 | 182,711 | 115,324 | 56,025 | 37,695 |
| PSA (ng/mL) | S/S0 | | | | | |
| 0.0 | 1.00 | 1.00 | 1.00 | 1.00 | 1.00 | 1.00 |
| 0.4 | 1.32 | 1.69 | 1.50 | 1.93 | 1.55 | 1.78 |
| 1.4 | 2.47 | 4.21 | 3.32 | 5.30 | 2.90 | 3.81 |
| 7.0 | 8.19 | 16.37 | 12.15 | 21.20 | 10.59 | 14.12 |
| 51.0 | 47.16 | 101.00 | 74.95 | 123.25 | 61.62 | 81.34 |
| 101.6 | 88.63 | 181.39 | 111.86 | 190.09 | 85.06 | 123.45 |

TABLE 22

| | | | | | | |
|---|---|---|---|---|---|---|
| | Solution Concentration of each reactant | | | | | |
| Dextran-Ab1-AK1 ug/mL | 2.5 | 2.5 | 2.5 | 2.5 | 2.5 | 2.5 |
| AB2-HRP conj ug/mL | 0.5 | 0.5 | 0.1 | 0.1 | 0.03 | 0.03 |
| Ascorbic acid uM | 200 | 500 | 200 | 500 | 200 | 500 |
| | Amount in Reaction Vessel | | | | | |
| Capture Ab (ng) | 62.5 | 62.5 | 62.5 | 62.5 | 62.5 | 62.5 |
| HRP-conj (ng) | 12.5 | 12.5 | 2.5 | 2.5 | 0.75 | 0.75 |
| Ascorbic acid Conc uM | 50 | 125 | 50 | 125 | 50 | 125 |
| Ascorbic acid nMoles | 5 | 12.5 | 5 | 12.5 | 5 | 12.5 |

TABLE 22-continued

| PSA (ng/mL) | Sum RLU | | | | | |
|---|---|---|---|---|---|---|
| 0.0 | 1,860 | 623 | 463 | 211 | 224 | 111 |
| 0.4 | 3,973 | 2,132 | 1,261 | 800 | 461 | 332 |
| 1.4 | 11,417 | 6,659 | 3,780 | 2,359 | 1,239 | 852 |
| 7.0 | 49,103 | 31,767 | 17,005 | 10,921 | 5,420 | 3,903 |
| 51.0 | 386,671 | 229,809 | 105,745 | 72,211 | 36,383 | 22,780 |
| 101.6 | 695,365 | 434,443 | 164,713 | 114,544 | 50,955 | 34,411 |
| PSA (ng/mL) | S/S0 | | | | | |
| 0.0 | 1.00 | 1.00 | 1.00 | 1.00 | 1.00 | 1.00 |
| 0.4 | 2.14 | 3.42 | 2.73 | 3.80 | 2.06 | 3.00 |
| 1.4 | 6.14 | 10.69 | 8.17 | 11.20 | 5.53 | 7.70 |
| 7.0 | 26.40 | 51.02 | 36.76 | 51.84 | 24.20 | 35.27 |
| 51.0 | 207.89 | 369.07 | 228.56 | 342.77 | 162.42 | 205.84 |
| 101.6 | 373.85 | 697.71 | 356.01 | 543.72 | 227.48 | 310.94 |

TABLE 23

| Solution Conc. | Solution Concentration of each reactant | | | | | |
|---|---|---|---|---|---|---|
| Dextran-Ab1-AK1 ug/mL | 0.5 | 0.5 | 0.5 | 0.5 | 0.5 | 0.5 |
| AB2-HRP conj ug/mL | 0.5 | 0.5 | 0.1 | 0.1 | 0.03 | 0.03 |
| Ascorbic acid uM | 200 | 500 | 200 | 500 | 200 | 500 |
| Amount in RV | Amount in Reaction Vessel | | | | | |
| Capture Ab (ng) | 12.5 | 12.5 | 12.5 | 12.5 | 12.5 | 12.5 |
| HRP-conj (ng) | 12.5 | 12.5 | 2.5 | 2.5 | 0.75 | 0.75 |
| Ascorbic acid Conc uM | 50 | 125 | 50 | 125 | 50 | 125 |
| Ascorbic acid nMoles | 5 | 12.5 | 5 | 12.5 | 5 | 12.5 |
| PSA (ng/mL) | Sum RLU | | | | | |
| 0.0 | 425 | 156 | 127 | 77 | 76 | 57 |
| 0.4 | 2,455 | 1,403 | 820 | 543 | 305 | 223 |
| 1.4 | 8,292 | 5,135 | 2,740 | 2,004 | 1,091 | 727 |
| 7.0 | 41,265 | 24,752 | 14,593 | 9,851 | 4,912 | 3,396 |
| 51.0 | 411,059 | 277,775 | 115,507 | 73,619 | 34,512 | 21,580 |
| 101.6 | 766,601 | 564,197 | 170,416 | 113,653 | 47,253 | 30,481 |
| PSA (ng/mL) | % CV | | | | | |
| 0.0 | 6.8% | 5.1% | 1.8% | 10.8% | 0.0% | 17.6% |
| 0.4 | 16.2% | 1.4% | 4.8% | 3.8% | 8.0% | 11.0% |
| 1.4 | 2.5% | 2.2% | 5.6% | 0.3% | 2.8% | 3.9% |
| 7.0 | 4.8% | 2.0% | 4.0% | 0.1% | 4.3% | 3.7% |
| 51.0 | 3.0% | 2.8% | 1.2% | 8.0% | 2.3% | 4.2% |
| 101.6 | 7.2% | 3.3% | 2.9% | 2.9% | 1.5% | 3.0% |
| PSA (ng/mL) | S/S0 | | | | | |
| 0.0 | 1.00 | 1.00 | 1.00 | 1.00 | 1.00 | 1.00 |
| 0.4 | 5.77 | 8.99 | 6.47 | 7.02 | 4.02 | 3.88 |
| 1.4 | 19.50 | 32.91 | 21.63 | 25.91 | 14.35 | 12.67 |
| 7.0 | 97.02 | 158.67 | 115.21 | 127.38 | 64.63 | 59.23 |
| 51.0 | 966.44 | 1780.61 | 911.89 | 951.97 | 454.11 | 376.40 |
| 101.6 | 1802.35 | 3616.65 | 1345.39 | 1469.66 | 621.75 | 531.65 |

Example 10. Preparation of Chemiluminescent-Labeled SBP Including Chemiluminescent Label, Dextran-Streptavidin Scaffold, and Biotin-Coupled Antibody and Use in Assays for TNI, CKMB or Myoglobin with Various SSIA A. Labeling of Amino-Modified Dextran with Chemiluminescent Compound and Amine and Sulfhydryl Reactive Heterobifunctional Crosslinker:

5.2 mg of NHS-(PEO)8-Maleimide (Thermo Fisher Scientific, Waltham, Mass.) and 22.1 mg AK1, an acridan ketenedithioacetal —NHS ester, ammonium salt were dissolved in DMSO to 30 mg/mL, combined, and added to 35 mg of 70 kDa Polyaminodextran (Helix Research, product #1209; 70 moles NH2/mole dextran), dissolved in PBS, pH 7.2 at 14 mg/mL, in a polypropylene reaction vessel. The reaction mixture was incubated for 45 minutes at ambient temperature protected from light. Unreacted amino groups on the polyaminodextran were blocked by incubating the conjugate with 10 μL of MS(PEG)8 (Thermo Fisher Scientific, Waltham, Mass.) for an additional 10 minutes at ambient temperature in the dark. The activated dextran was clarified by microcentrifugation (14K×g, 1 min.) and purified over a Sephadex G-25 columns (GE Healthcare, Piscataway, N.J.), equilibrated in PBS, pH 7.2 containing 1 mM EDTA, following the manufacturers instructions.

B. Thiolation of Streptavidin:

A 50-fold molar excess (5.63 mg) of 2-iminothiolane (Thermo Fisher Scientific, Waltham, Mass.) was added to 45 mg (10 mg/mL) of streptavidin-Plus® (Prozyme, Hayward, Calif.). PBS, pH 7.4 (1 mL) was added to the mixture to increase the pH of the reaction to 7.0. The mixture was incubated at ambient temperature for 45 minutes in the dark. The thiolated streptavidin was purified over Sephadex® G-25 columns (GE Healthcare, Piscataway, N.J.), equilibrated in PBS, pH 7.2 containing 1 mM EDTA, following the manufacturers instructions.

C. Conjugation of Thiolated Streptavidin to AK-Derivatized and Maleimide-Activated Dextran.

Next, the activated dextran (A) and thiolated streptavidin (B) were combined and reacted overnight at ambient temperature, protected from light. Un-reacted maleimide and thiol groups were subsequently blocked in a two-step process. In the first step, an excess (0.025× reaction volume) of 50 mg/mL L-cysteine-HCl (dissolved in PBS, pH 7.4) was added to the conjugate and incubated 15 minutes. In the second step, an excess (0.04× reaction volume) of 50 mg/mL iodoacetamide (dissolved in PBS, pH 7.4) was added to the reaction mixture together with 50 mM Borate, pH 8.5 (0.08× reaction volume) and incubated for an additional 15 minutes at ambient temperature protected from light.

D. Purification of Streptavidin~Dextran~AK1 Conjugate

The conjugate was clarified by microcentrifugation (14K×g, 2 min.) and purified over a Superdex® 200 column (GE Healthcare, Piscataway, N.J.) equilibrated in PBS, pH 7.4 on a System Gold® HPLC System (Beckman Coulter, Inc., Brea, Calif.) with Binary Gradient 125 Pump and Diode Array 168 Detector coupled to a Gilson FC 203B fraction collector. The programmed flow rate was 1 mL/min.; sample injection loop volume—1 mL; fractionation—1 mL/fraction). The conjugate fractions were carefully pooled in order to exclude a small amount of unreacted streptavidin that elutes after the conjugate. The concentration of streptavidin in the pooled conjugate was determined with the BCA protein assay (Thermo Fisher Scientific, Waltham, Mass.), using streptavidin Plus® at predetermined concentrations as standards. The concentration of AK1 was determined spectrophotometrically (E384=13.6 mg-1 mL-1). The calculated streptavidin concentration and AK:streptavidin molar ratio of the conjugate pool was 1.47 mg/mL and 18:1, respectively.

E. Biotinylation of xPSA Monoclonal Antibodies

Biotinylated PSA antibodies were prepared by adding a 6-fold molar excess of NHS-(PEO)4-biotin (Thermo Fisher Scientific, Waltham, Mass.), dissolved in DMSO to 2 mg/mL, to 6 mg of MxPSA antibody (7.6 mg/mL in PBS, pH 7.4). After a 60 min. incubation at ambient temperature, the biotinylated antibody was purified over a Sephadex G-25 column (GE Healthcare, Piscataway, N.J.), equilibrated in PBS, pH 7.4, following the manufacturers instructions.

F. Coupling of Biotinylated Antibody to Streptavidin~Dextran~AK Conjugates

Coupling was performed by incubating the streptavidin~dextran~AK conjugate (1.47 μg/mL) with biotinylated anti-PSA monoclonal (2 μg/mL) in diluent (100 mM Tris, pH 8.0, 150 mM NaCl, 0.2% Tween®-20, 0.1 mM EDTA, 1% BSA) for 30 minutes. This corresponds to a 2:1 molar ratio of streptavidin:biotinylated antibody.

G. Assays for TnI, CKMB or Myoglobin with Dextran Scaffold Chemiluminescent-Labeled sbp and SSIA This example demonstrates assay methods for detecting an analyte, such as Troponin I, CKMB or Myoglobin. For each assay, the specific binding pair employed is a pair of monoclonal antibodies, each antibody specific for a different antigenic site on the specified analyte. For each assay, a first antibody was biotinylated and conjugated to a Dextran-AK1-streptavidin scaffold ("Ab scaffold"), prepared by methods similar to those described above in Example 5, and provided in an aqueous solution at 0.5 μg/ml or 2 μg/ml. A second antibody for each assay was conjugated with HRP as described above, ("HRP conjugate") and provided at 0.25 μg/ml or 1 μg/ml in aqueous solution (100 mM Tris, 150 mM NaCl pH 8.0, 0.2% Tween20, 0.1 mM EDTA, 1% BSA).

Each assay was performed by adding 25 μl of Ab scaffold, 25 μl 600 μM ascorbic acid in water, 25 μl of sample and 254, HRP conjugate to a reaction vessel. The reaction mixture was incubated for 15 min at 37° C. The reaction vessel was positioned for detection by luminometer, then 100 μL of trigger solution A was added and the light intensity recorded over a time period of several seconds. The data collected by the luminometer corresponding to an elapsed time of 302.5 milliseconds approximately centered on the peak signal were summed, averaged over three runs per sample and presented in Table 24-26. Signal to noise was calculated for each sample.

The results of this example demonstrate the application of assays of the present to other analytes. In addition, the example successfully demonstrates assays utilizing different concentrations and ratios of reactants for chemiluminescent-labeled sbp, activator-labeled sbp, and SSIA. The methods of Example 7 are suitable for use in determination of analyte concentration in unknown samples, including the generation of calibration curves for determination of TnI, CKMB or Myoglobin concentration according to standard methods.

TABLE 24

| | | TnI | | | | | | | |
|---|---|---|---|---|---|---|---|---|---|
| | | Ab Scaffold μg/mL | | | | | | | |
| | | 0.5 | | 0.5 | | 2 | | 2 | |
| | | HRP-conj μg/mL | | | | | | | |
| | | 0.25 | | 1 | | 0.25 | | 1 | |
| | | Ascorbic Acid μM | | | | | | | |
| | | 600 | | 600 | | 600 | | 600 | |
| Cal. | TnI ng/ml | RLU | S/S0 | RLU | S/S0 | RLU | S/S0 | RLU | S/S0 |
| S0 | 0 | 53 | | 71 | | 95 | | 171 | |
| S1 | 0.17 | 72 | 1.4 | 112 | 1.6 | 152 | 1.6 | 329 | 1.9 |
| S2 | 0.37 | 116 | 2.2 | 169 | 2.4 | 201 | 2.1 | 481 | 2.8 |
| S3 | 1.37 | 236 | 4.4 | 345 | 4.9 | 547 | 5.8 | 1,029 | 6.0 |

TABLE 24-continued

| | | TnI | | | | | | | |
|---|---|---|---|---|---|---|---|---|---|
| | | Ab Scaffold μg/mL | | | | | | | |
| | | 0.5 | | 0.5 | | 2 | | 2 | |
| | | HRP-conj μg/mL | | | | | | | |
| | | 0.25 | | 1 | | 0.25 | | 1 | |
| | | Ascorbic Acid μM | | | | | | | |
| | | 600 | | 600 | | 600 | | 600 | |
| Cal. | TnI ng/ml | RLU | S/S0 | RLU | S/S0 | RLU | S/S0 | RLU | S/S0 |
| S4 | 11.1 | 1743 | 32.7 | 3165 | 44.8 | 1203 | 12.7 | 8,697 | 51.0 |
| S5 | 27.9 | 4863 | 91.2 | 8371 | 118.5 | 7813 | 82.5 | 22,883 | 134.1 |
| S6 | 106 | 25494 | 478.0 | 47372 | 670.4 | 54992 | 580.9 | 125,264 | 734.0 |

TABLE 25

| | | CKMB | | | | | | | |
|---|---|---|---|---|---|---|---|---|---|
| | | Ab Scaffold μg/mL | | | | | | | |
| | | 0.5 | | 0.5 | | 2 | | 2 | |
| | | HRP-conj μg/mL | | | | | | | |
| | | 0.25 | | 1 | | 0.25 | | 1 | |
| | | Ascorbic Acid μM | | | | | | | |
| | | 600 | | 600 | | 600 | | 600 | |
| Cal. | CKMB ng/ml | RLU | S/S0 | RLU | S/S0 | RLU | S/S0 | RLU | S/S0 |
| S0 | 0.6 | 72 | | 120 | | 113 | | 264 | |
| S1 | 3.2 | 92 | 1.3 | 143 | 1.2 | 160 | 1.4 | 404 | 1.5 |
| S2 | 9.6 | 111 | 1.5 | 247 | 2.1 | 231 | 2.0 | 700 | 2.7 |
| S3 | 29.2 | 179 | 2.5 | 451 | 3.8 | 448 | 4.0 | 1499 | 5.7 |
| S4 | 109.4 | 523 | 7.3 | 1635 | 13.6 | 1593 | 14.1 | | |
| S5 | 315.8 | 1953 | 27.1 | 6641 | 55.3 | 5977 | 52.7 | 21517 | 81.5 |

TABLE 26

| | | Myoglobin | | | | | | | |
|---|---|---|---|---|---|---|---|---|---|
| | | Ab Scaffold μg/mL | | | | | | | |
| | | 0.5 | | 0.5 | | 2 | | 2 | |
| | | HRP-conj μg/mL | | | | | | | |
| | | 0.25 | | 1 | | 0.25 | | 1 | |
| | | Ascorbic Acid μM | | | | | | | |
| | | 600 | | 600 | | 600 | | 600 | |
| Cal. | Myo ng/ml | RLU | S/S0 | RLU | S/S0 | RLU | S/S0 | RLU | S/S0 |
| S1 | 11.4 | 45 | | 113 | | 159 | | 361 | |
| S2 | 57.2 | 11328 | 250 | 36861 | 325 | 43469 | 274 | 119387 | 330 |
| S3 | 219 | 52303 | 1,154 | 328599 | 2,899 | 171988 | 1,084 | 990660 | 2,742 |
| S4 | 830 | 70411 | 1,553 | 481109 | 4,245 | 220796 | 1,392 | 1507591 | 4,172 |

The assays were performed using a modified DxI® (Beckman Coulter) automated immunoassay instrument as described above.

H. Assays Utilizing Various SSIA in TnI Assay

Multiple concentration levels of 5 different SSIA were demonstrated in the context of TnI assay system according to the present disclosure. Concentrated stock solutions of ascorbic acid, TROLOX, phenoxazine, 3-aminotyrosine, and 2-aminophenol, all available from Sigma Aldrich, were prepared in deionized water at 100 mM.

In a reaction tube, 400 uL of TnI M6 antibody-HRP conjugate at 0.5 ug/mL in buffered aqueous solution at pH. 8.0 (100 mM Tris, 150 mM NaCl, 0.1 mM EDTA, 0.2% Tween-20 and 1% BSA), 400 uL of AK1~Dex70/31~Streptavidin (fraction 1) 2:1 SA/Ab at 2 ug/mL Ab also in buffered aqueous solution at pH 8.0, and 400 uL of calibrator standard solution containing the TnI analyte at a known concentration. One tube was prepared for each calibrator concentration. 75 uL of the premixed solution of Ab-HRP conjugate, scaffold and standards were delivered by octapet into each well of a Corning/Sostar 96-well polypropylene microtiter plate (white, Corning Cat. #3355) and allowed to incubated for 38-49 minutes at room temperature. Next, 25 uL of each antioxidant as a concentrated solution of 2 mM, 1 mM or 0.5 mM was pipetted into the plate wells using a repeater pipette. The plates were rotated for 10 seconds to mix and incubated between 5 to 33 minutes. Detection was performed with a SpectraMax L injection plate luminometer. Baseline reads were taken, followed by injection of 100 μL of Trigger Solution A into each well and reading of the chemiluminescent signal.

TABLE 27

Signal to Noise and final concentration of SSIA in reaction mixture including trigger solution volume.

| Signal/ | | | | Ascorbic Acid | | | Trolox | | |
|---|---|---|---|---|---|---|---|---|---|
| Noise | DiH20 (control) | | | 500 uM | 250 uM | 125 uM | 500 uM | 250 uM | 125 uM |
| S0/S0 | 1.0 | 1.0 | 1.0 | 1.0 | 1.0 | 1.0 | 1.0 | 1.0 | 1.0 |
| S1/S0 | 0.9 | 1.1 | 1.2 | 1.3 | 1.6 | 1.4 | 1.7 | 2.0 | 1.6 |
| S2/S0 | 1.0 | 1.1 | 1.2 | 1.8 | 2.6 | 2.7 | 2.6 | 3.5 | 3.3 |
| S3/S0 | 1.4 | 1.8 | 1.9 | 5.1 | 8.2 | 8.5 | 11.3 | 12.8 | 11.5 |
| S4/S0 | 3.2 | 4.0 | 4.2 | 15.4 | 28.7 | 32.2 | 31.1 | 45.8 | 44.4 |
| S5/S0 | 17.4 | 20.6 | 25.7 | 87.5 | 188.5 | 228.0 | 192.0 | 295.1 | 302.0 |
| S6/S0 | 139.8 | 200.3 | 283.2 | 562.4 | 1511.1 | 2196.3 | 1181.7 | 2334.5 | 2713.1 |
| | Phenoxazine | | | 3-Amino Tyrosine | | | 2-Aminophenol | | |
| | 25 uM | 12.5 uM | 6.25 uM | 500 uM | 250 uM | 125 uM | 500 uM | 250 uM | 125 uM |
| S0/S0 | 1.0 | 1.0 | 1.0 | 1.0 | 1.0 | 1.0 | 1.0 | 1.0 | 1.0 |
| S1/S0 | 1.3 | 1.5 | 1.5 | 1.1 | 1.7 | 1.5 | 1.3 | 0.9 | 1.4 |
| S2/S0 | 1.6 | 2.3 | 3.1 | 1.9 | 2.7 | 2.8 | 1.8 | 1.7 | 2.3 |
| S3/S0 | 3.7 | 6.4 | 8.4 | 5.9 | 8.1 | 9.0 | 4.8 | 4.5 | 7.6 |
| S4/S0 | 12.1 | 24.5 | 32.1 | 19.8 | 31.1 | 32.2 | 10.8 | 15.4 | 27.2 |
| S5/S0 | 62.8 | 147.2 | 227.2 | 118.6 | 217.9 | 234.8 | 52.5 | 101.7 | 183.7 |
| S6/S0 | 387.3 | 1116.9 | 2049.8 | 766.3 | 1772.4 | 2268.7 | 329.9 | 739.1 | 1604.7 |

Conclusion: All SSIA tested in this representative TnI solution phase assay format behave effectively at improving signal to noise.

Example 11. Preparation of Chemiluminescent-Labeled SBP Including Chemiluminescent Label, PAA Scaffold, and Streptavidin-Biotin-Coupled Antibody This example describes the formation of a scaffold with a poly(acrylic acid) backbone coupled to streptavidin and conjugated to a biotinylated antibody. The example also describes immunoassay for an analyte using the PAA scaffold.

A. Labeling of Polyacrylic Acid (PAA) with Chemiluminescent Compound and Biotin:

2 mg of polyacrylic acid (PAA) sodium salt (Polysciences, Warrington Pa.) was dissolved in 0.4 mL of 100 mM MES, pH 6.0. Fifty (50) molar equivalents (20 mg) of EDC (Thermo Scientific) and 6 mg of N-hydroxysulfosuccinimide (Thermo Scientific) were dissolved in deionized water and added to the PAA solution, while mixing to activate the carboxylate groups. After 20 minutes of activation, 50 molar equivalents (0.843 mg) of biotin-PEG4-hydrazide (Thermo Scientific), and 50 molar equivalents (1.01 mg) of AK1-hydrazide prepared in anhydrous DMSO, were added to the PAA solution and allowed to react overnight at room temperature with mixing. The labeled PAA was purified by buffer exchange in PBS, pH 7.2 using a 10 kDa MWCO centrifugal concentrator (Millipore, Billerica Mass.) and restored to the original volume in PBS after five (5) exchanges. The biotin- and AK1-labeled PAA was designated PAA-B.

B. Coupling of Labeled PAA with Streptavidin

A 0.75 mg/mL solution of biotin- and AK1-labeled PAA (PAA-B) was prepared in PBS, pH 7.4. 100 μL of PAA-B was mixed with 13.75 μL of a 10 mg/mL solution of streptavidin (Prozyme, Hayward Calif.), corresponding to a 2:1 molar ratio of streptavidin to PAA, and the mixture was incubated overnight at 4° C.

C. Coupling of Biotinylated Antibodies to Streptavidin-PAA Conjugate to Form Final Scaffold Antibodies were biotinylated as demonstrated in previous examples. The PAA scaffold was formed by coupling the streptavidin-PAA-B conjugate to the antibody by incubating the streptavidin-PAA-B conjugate with biotinylated anti-cTnI at 4° C. overnight. Molar ratios of streptavidin:antibody varied from 1:1 to 1:4.

D. Immunoassay for TnI with PAA Scaffold

The PAA scaffolds are useful in assay methods for detecting an analyte such as cTnI, as described in Example 6. A first antibody for TnI was conjugated to a PAA-AK1-streptavidin scaffold, prepared as described above, and provided in an aqueous solution at 2 μg/mL. A second antibody was then conjugated to HRP and provided at 0.5 μg/mL in an aqueous solution, as described in Example 2.

The immunoassay was performed as described in Example 17. Briefly, equal volumes of the PAA scaffold, HRP conjugate, 600 μM ascorbic acid in water and the analyte sample were mixed together in 96-well microtiter plates.

cTnI samples were prepared by adding known quantities of native cardiac troponin I (Scipac; Sittingbourne UK) to normal human serum, as described in Example 6. Briefly, known concentrations of TnI were spiked into normal human serum and analyzed according to the assay described above. The data can be used to generate a calibration curve for analysis of TnI at unknown concentrations.

TABLE 28

| | | PAA-B | | |
|---|---|---|---|---|
| | | Input | AK1:biotin = 50/50 Sample B-1 Input 2 SA/PAA b Output 2 SA/PAA | |
| | Btn-Aby/SA Input Tri ng/mL | 1:1 Mean | 1:2 Mean | 1:4 Mean |
| S0 | 0 | 3,574 | 4,446 | 5,884 |
| S1 | 0.1 | 5,492 | 4,620 | 7,191 |
| S2 | 0.22 | 7,540 | 7,889 | 9,457 |
| S3 | 0.82 | 14,731 | 14,295 | 20,570 |
| S4 | 2.3 | 35,257 | 42,840 | 48,462 |
| S5 | 9.2 | 136,677 | 144,827 | 184,274 |
| S6 | 41 | 623,412 | 624,243 | 801,758 |
| S7 | 190 | 2,259,096 | 2,303,353 | 2,773,923 |
| | | % CV | % CV | % CV |
| S0 | 0 | — | 13.9% | 5.2% |
| S1 | 0.1 | 11.2% | 29.3% | 7.7% |
| S2 | 0.22 | 15.5% | 5.5% | 3.3% |
| S3 | 0.82 | 20.9% | 17.2% | — |
| S4 | 2.3 | 13.5% | 4.5% | 13.0% |
| S5 | 9.2 | 13.9% | 7.4% | 3.5% |
| S6 | 41 | 1.9% | 0.9% | 1.4% |
| S7 | 190 | 2.4% | 0.5% | 2.5% |
| | | S/S0 | S/S0 | S/S0 |
| S0 | 0 | 1.00 | 1.00 | 1.00 |
| S1 | 0.1 | 1.54 | 1.04 | 1.22 |
| S2 | 0.22 | 2.11 | 1.77 | 1.61 |
| S3 | 0.82 | 4.12 | 3.22 | 3.50 |
| S4 | 2.3 | 9.86 | 9.64 | 8.24 |
| S5 | 9.2 | 38.24 | 32.58 | 31.32 |
| S6 | 41 | 174.42 | 140.41 | 136.26 |
| S7 | 190 | 632.07 | 518.10 | 471.45 |

b Output (molar ratio of SA:PAA) was calculated from size exclusion chromatography analysis, by using streptavidin as standard.

Example 12. Preparation of Chemiluminescent-Labeled SBP, PAA Scaffold, and Thiolated Antibody This example describes preparation of a PAA scaffold labeled with AK1 and maleimide using EDC chemistry and conjugated with monoclonal anti-TnI (284) antibody via a thiol-maleimide reaction. The example also demonstrates immunoassay for an analyte using the PAA scaffold.

A. Labeling of PAA with Chemiluminescent Compound and Heterobifunctional Crosslinker AK1- and maleimide-labeled PAA (mol. wt. approx. 225,000) was prepared as described in Example 11, except that 20 molar equivalents of (N-[k-maleimidoundecanoic acid]hydrazide) (Thermo Scientific), and 20 molar equivalents of AK2, prepared in anhydrous DMSO, were added to the PAA solution and allowed to react 1 hour at room temperature with mixing. The labeled PAA was purified by dialysis against PBS, pH 7.2 using a 10 kDa MWCO Slide-A-Lyzer® Dialysis Cassettes (Thermo Scientific). The final concentration of PAA was 1.4 mg/ml, assuming no loss of polymer during dialysis.

B. Thiolation of Monoclonal Anti-TnI (284) Antibody

Monoclonal anti-TnI (284) antibody was dialyzed against 100 mM MES, pH 6.0 buffer before use. Traut's Reagent (2-iminothiolane.HCl) (Thermo Scientific) was dissolved in deionized water at a concentration of 2 mg/mL. 6.4 mg of antibody at a concentration of 3.2 mg/mL was reacted with 2.36 μL of 2-iminothiolane (10 molar equivalents per equivalent of antibody) for 1 hour, at room temperature. The thiolated antibody was purified using PD-10 desalting columns (GE Healthcare, Piscataway N.J.) equilibrated with PBS, pH 7.2, and containing 1 mM EDTA.

C. Coupling of Thiolated Antibody to AK1- and Maleimide-Labeled PAA

105 μL of the AK1- and maleimide-labeled PAA solution, at a concentration of 1.4 mg/ml, was mixed immediately with 0.6 mg of thiolated monoclonal anti-TnI (284) antibody, at a concentration of 3.8 mg/mL, corresponding to 6 equivalents of antibody per equivalent of PAA. The reaction was performed at 4° C., and the reaction product purified by size exclusion HPLC. Individual HPLC fractions of the product peak (denoted as Fr3, Fr4 and Fr5 in Table 29) were evaluated in the immunoassay.

D. Immunoassay for Monoclonal Anti-TnI Antibody with PAA Scaffold

An immunoassay for monoclonal anti-TnI using the AK1- and maleimide-labeled PAA scaffold was performed as described in Example 20. Briefly, equal volumes of the AK1- and maleimide-labeled PAA scaffold, HRP conjugate, 600 μM ascorbic acid in water and sample were mixed together in a reaction vessel for 30 minutes. The mixture was incubated with 100 μL of trigger solution A, i.e. a trigger solution, to initiate the chemiluminescent reaction. After initiation, the samples were read on a SpectraMax® L microplate luminometer in the fast read kinetic mode, and chemiluminescent signal were recorded over a time period of about 0.12 to 0.21 seconds. For each sample, five (5) baseline reads were collected prior to initiation by addition of the trigger solution. The values reported in Table 29 are the sum of multiple data points.

TABLE 29

| | | PAA-B | | | |
|---|---|---|---|---|---|
| | | Unpurified PAA- | Purified by HPLC | | |
| | Tnl ng/mL | B | Frx3 | Frx4 | Frx5 |
| | | Mean RLU | | | |
| S0 | 0 | 10,808 | 9,733 | 9,821 | 11,971 |
| S1 | 0.1 | 12,857 | 19,001 | 15,341 | 14,731 |
| S2 | 0.22 | 16,997 | 23,737 | 22,343 | 20,105 |
| S3 | 0.82 | 38,482 | 64,065 | 51,049 | 35,388 |
| S4 | 2.3 | 165,357 | 341,500 | 242,947 | 175,005 |
| S5 | 9.2 | 512,474 | 1,018,277 | 729,631 | 504,771 |
| S6 | 41 | 2,692,899 | 5,704,473 | 4,617,038 | 3,186,736 |
| S7 | 190 | 9,635,260 | 19,995,274 | 14,644,731 | 9,579,212 |
| | | S/S0 | | | |
| S0 | 0 | 1.00 | 1.0 | 1.00 | 1.00 |
| S1 | 0.1 | 1.19 | 1.95 | 1.56 | 1.23 |
| S2 | 0.22 | 1.57 | 2.44 | 2.28 | 1.68 |
| S3 | 0.82 | 3.56 | 6.58 | 5.20 | 2.96 |
| S4 | 2.3 | 15.30 | 35.09 | 24.74 | 14.62 |
| S5 | 9.2 | 47.41 | 104.62 | 74.30 | 42.17 |
| S6 | 41 | 249.15 | 586.07 | 470.14 | 266.22 |
| S7 | 190 | 891.46 | 2054.29 | 1491.23 | 800.23 |

Example 13. Preparation of Chemiluminescent-Labeled SBP Including Chemiluminescent Label, Self-Assembling Polymer, and Streptavidin-Biotin-Coupled Antibody In the following examples, AK1-labeled streptavidin is mixed with biotinylated polyacrylic acid (PAA), and polymer complexes form by self-assembly. These self-assembling polymers function as scaffold materials for immunoassay of an analyte.

A. Preparation of Biotinylated PAA

AK1-labeled streptavidin and biotinylated monoclonal cTnI 284 antibody were prepared according to the methods described in Example 6.

200 mg of 225 kDa poly(acrylic acid) sodium salt was dissolved in 70 mL of 100 mM MES, pH 6.0. To activate the carboxylate groups, 2 g of 1-ethyl-3-[3-dimethylaminopropyl]carbodiimide hydrochloride and 0.9 g of N-hydroxysulfosuccinimide) were dissolved in 10 mL of deionized water and added to the PAA solution while mixing. After 20 minutes of activation, 45 mg of biotin-PEG4-hydrazide, prepared at a concentration of 2.25 mg/mL in anhydrous DMSO, was added to the PAA solution and allowed to mix overnight at room temperature. The biotinylated PAA was then dialyzed extensively against deionized water to remove reaction byproducts. Following dialysis, the biotinylated polymer was dried in a SpeedVac® concentrator under vacuum (Thermo/Savant) and the dried polymer (110 mg) was dissolved in PBS, pH 7.2 at a concentration of 2 mg/mL. The biotin:PAA molar ratio (25 biotin:PAA) was determined using a commercial HABA assay kit (Thermo Scientific).

Example 14. Preparation of Chemiluminescent-Labeled SBP Including Chemiluminescent Label, Self-Assembling Polymer with PAA In this example, biotinylated polyacrylic acid (PAA) is used to terminate the polymerization reaction for the polymer complexes formed by self-assembly, as described in Example 6, and to stabilize the polymers after formation. Briefly, biotinylated antibodies are assembled with AK1-labeled streptavidin (as described previously) at an optimized molar ratio. Biotinylated polyacrylic acid (PAA) is then added to stabilize the self-assembled polymer.

A. Preparation of Self-Assembled Polymers

Biotinylated IgG, at a concentration of 2.66 mg/mL was mixed with AK1-labeled streptavidin, at a concentration of 0.584 mg/mL, and prepared as described in Example 7. Various ratios of biotinylated IgG:AK1-labeled streptavidin, from 0.25 to 1.25, and the mixtures were allowed to incubate overnight at 4° C. to allow self-assembly.

B. Preparation of Hybrid Constructs

The self-assembled constructs were divided into equal volumes, and biotinylated PAA was added, at various molar ratios of PAA:Streptavidin, from 0 to 1. The reaction was performed at 4° C. and incubated overnight to form stable hybrid PAA constructs.

C. Immunoassay with PAA Hybrid Scaffold

An immunoassay for monoclonal anti-TnI using the PAA hybrid scaffold was performed as described in Example 11. Briefly, equal volumes of the PAA scaffold, HRP conjugate, 600 mM ascorbic acid in water and sample were mixed together in a reaction vessel. The mixture was incubated with trigger solution A, i.e. a trigger solution, to initiate the chemiluminescent reaction. After initiation of the chemiluminescent reaction, the samples were read on a SpectraMax® L microplate luminometer in the fast read kinetic mode, and chemiluminescent signal were recorded over a time period of about 0.12 to 0.21 seconds. Results of the immunoassay are shown in Tables 30A-30E.

TABLE 30A

| | 0.25 IgG/SA | | | | |
|---|---|---|---|---|---|
| [TnI] (ng/ml) | 0 SA/PAA | 1 SA/PAA | 3 SA/PAA | 5 SA/PAA | 8 SA/PAA |
| | Average RLU | | | | |
| 0 | 4,184 | 12,552 | 11,331 | 8,499 | 6,145 |
| 0.1 | 5,840 | 10,503 | 12,116 | 7,278 | 8,194 |
| 0.22 | 6,058 | 17,389 | 21,921 | 14,556 | 10,590 |
| 0.82 | 16,343 | 38,439 | 59,271 | 36,347 | 26,149 |
| 2.3 | 36,477 | 113,140 | 162,263 | 114,143 | 80,147 |
| 9.2 | 142,955 | 457,276 | 700,534 | 460,856 | 326,085 |
| 41 | 783,310 | 2,476,519 | 4,488,906 | 2,856,273 | 2,580,275 |
| 190 | 3,167,727 | 10,178,765 | 21,747,411 | 15,590,607 | 12,600,311 |
| | S/S0 | | | | |
| 0 | 1.00 | 1.00 | 1.00 | 1.00 | 1.00 |
| 0.1 | 1.40 | .84 | 1.07 | 0.86 | 1.33 |
| 0.22 | 1.45 | 1.39 | 1.93 | 1.71 | 1.72 |
| 0.82 | 3.91 | 3.06 | 5.23 | 4.28 | 4.26 |
| 2.3 | 8.72 | 9.01 | 14.32 | 13.43 | 13.04 |
| 9.2 | 34.17 | 36.43 | 61.82 | 54.23 | 53.06 |
| 41 | 187.20 | 197.31 | 396.15 | 336.09 | 419.88 |
| 190 | 757.06 | 810.95 | 1,919.23 | 1,834.48 | 2,050.39 |

TABLE 30B

| [TnI] | 0.5 IgG/SA | | | | |
|---|---|---|---|---|---|
| (ng/ml) | 0 SA/PAA | 1 SA/PAA | 3 SA/PAA | 5 SA/PAA | 8 SA/PAA |
| | Average RLU | | | | |
| 0 | 4,010 | 5,884 | 7,540 | 8,019 | 6,538 |
| 0.1 | 4,620 | 8,106 | 11,375 | 11,201 | 9,588 |
| 0.22 | 6,799 | 11,811 | 14,992 | 22,488 | 21,006 |
| 0.82 | 14,687 | 31,378 | 52,603 | 67,028 | 57,876 |
| 2.3 | 50,685 | 104,118 | 148,838 | 249,794 | 204,284 |
| 9.2 | 188,943 | 417,949 | 603,279 | 1,170,506 | 1,092,619 |
| 41 | 1,221,385 | 2,765,122 | 6,039,909 | 15,913,289 | 15,048,299 |
| 190 | 6,571,327 | 15,707,578 | 96,187,150 | 205,809,423 | 156,927,524 |
| | S/S0 | | | | |
| 0 | 1.00 | 1.00 | 1.00 | 1.00 | 1.00 |
| 0.1 | 1.15 | 1.38 | 1.51 | 1.40 | 1.47 |
| 0.22 | 1.70 | 2.01 | 1.99 | 2.80 | 3.21 |
| 0.82 | 3.66 | 5.33 | 6.98 | 8.36 | 8.85 |
| 2.3 | 12.64 | 17.70 | 19.74 | 31.15 | 31.25 |
| 9.2 | 47.12 | 71.03 | 80.01 | 145.96 | 167.13 |
| 41 | 304.59 | 469.95 | 801.06 | 1,984.38 | 2,301.82 |
| 190 | 1,638.76 | 2,669.60 | 12,757.11 | 25,664.37 | 24,004.00 |

TABLE 30C

| [TnI] | 0.75 IgG/SA | | | | |
|---|---|---|---|---|---|
| (ng/ml) | 0 SA/PAA | 1 SA/PAA | 3 SA/PAA | 5 SA/PAA | 8 SA/PAA |
| | Average RLU | | | | |
| 0 | 7,366 | 8,019 | 7,801 | 9,196 | 9,893 |
| 0.1 | 10,590 | 11,811 | 13,075 | 16,343 | 14,818 |
| 0.22 | 22,183 | 25,495 | 28,981 | 35,649 | 40,095 |
| 0.82 | 73,087 | 79,580 | 112,182 | 131,969 | 144,261 |
| 2.3 | 285,152 | 259,992 | 363,097 | 445,898 | 573,885 |
| 9.2 | 2,447,372 | 1,372,384 | 2,049,153 | 2,620,363 | 3,844,405 |

TABLE 30C-continued

| [Tnl] | 0.75 IgG/SA | | | | |
|---|---|---|---|---|---|
| (ng/ml) | 0 SA/PAA | 1 SA/PAA | 3 SA/PAA | 5 SA/PAA | 8 SA/PAA |
| 41 | 43,338,476 | 13,828,384 | 33,016,180 | 59,347,317 | 89,147,402 |
| 190 | 168,827,565 | 79,333,148 | 184,698,375 | 304,942,403 | 279,613,531 |
| | S/S0 | | | | |
| 0 | 1.00 | 1.00 | 1.00 | 1.00 | 1.00 |
| 0.1 | 1.44 | 1.47 | 1.68 | 1.78 | 1.50 |
| 0.22 | 3.01 | 3.18 | 3.71 | 3.88 | 405 |
| 0.82 | 9.82 | 9.92 | 14.38 | 14.35 | 14.58 |
| 2.3 | 38.71 | 32.42 | 46.54 | 48.49 | 58.01 |
| 9.2 | 332.27 | 171.14 | 262.67 | 284.95 | 388.59 |
| 41 | 5,883.92 | 1,724.40 | 4,232.10 | 6,453.66 | 9,010.98 |
| 190 | 22,921.17 | 9,892.82 | 23,675.12 | 33,160.62 | 28,263.20 |

TABLE 30D

| | 1 IgG/SA | | | | |
|---|---|---|---|---|---|
| [Tnl] (ng/ml) | 0 SA/PAA | 1 SA/PAA | 3 SA/PAA | 5 SA/PAA | 8 SA/PAA |
| | Average RLU | | | | |
| 0 | 9,457 | 6,843 | 8,194 | 8,586 | 9,152 |
| 0.1 | 19,481 | 13,815 | 14,948 | 18,217 | 18,696 |
| 0.22 | 49,203 | 36,870 | 41,969 | 51,252 | 48,593 |
| 0.82 | 168,105 | 91,086 | 119,984 | 139,685 | 138,246 |
| 2.3 | 627,056 | 430,593 | 564,030 | 695,181 | 704,733 |
| 9.2 | 4,694,988 | 1,736,105 | 2,366,367 | 3,202,127 | 3,633,556 |
| 41 | 91,062,483 | 17,583,497 | 35,058,831 | 58,755,998 | 70,824,415 |
| 190 | 331,954,679 | 132,619,201 | 293,094,757 | 375,459,073 | 375,947,567 |
| | S/S0 | | | | |
| 0 | 1.00 | 1.00 | 1.00 | 1.00 | 1.00 |
| 0.1 | 2.06 | 2.02 | 1.82 | 2.12 | 2.04 |
| 0.22 | 5.20 | 5.39 | 5.12 | 5.97 | 5.31 |
| 0.82 | 17.77 | 13.31 | 14.64 | 16.27 | 15.11 |
| 2.3 | 66.30 | 62.93 | 68.84 | 80.97 | 77.00 |
| 9.2 | 496.44 | 253.72 | 288.81 | 372.96 | 397.01 |
| 41 | 9,628.70 | 2,569.70 | 4,278.81 | 6,843.39 | 7,738.39 |
| 190 | 35,099.97 | 19,381.36 | 35,771.23 | 43,730.22 | 41,076.66 |

TABLE 30E

| [Tnl] | 1.25 IgG/SA | | | | |
|---|---|---|---|---|---|
| (ng/ml) | 0 SA/PAA | 1 SA/PAA | 3 SA/PAA | 5 SA/PAA | 8 SA/PAA |
| | Average RLU | | | | |
| 0 | 11,506 | 6,407 | 9,065 | 10,068 | 6,450 |
| 0.1 | 25,626 | 13,467 | 16,735 | 16,256 | 14,295 |
| 0.22 | 58,835 | 30,202 | 34,909 | 38,177 | 22,837 |
| 0.82 | 207,685 | 85,595 | 103,378 | 104,467 | 67,074 |
| 2.3 | 872,612 | 363,237 | 493,264 | 499,806 | 311,519 |
| 9.2 | 10,022,572 | 1,959,241 | 2,419,036 | 3,012,092 | 1,637,333 |
| 41 | 148,756,072 | 27,487,732 | 40,916,313 | 50,923,490 | 15,755,349 |
| 190 | 459,829,313 | 135,376,541 | 230,820,255 | 242,615,955 | 55,732,378 |
| | S/S0 | | | | |
| 0 | 1.00 | 1.00 | 1.00 | 1.00 | 1.00 |
| 0.1 | 2.23 | 2.10 | 1.85 | 1.61 | 2.22 |
| 0.22 | 5.11 | 4.71 | 3.85 | 3.79 | 3.54 |
| 0.82 | 18.05 | 13.36 | 11.40 | 10.38 | 10.40 |
| 2.3 | 75.84 | 56.70 | 54.41 | 49.65 | 48.29 |
| 9.2 | 871.10 | 305.81 | 266.85 | 299.19 | 253.83 |
| 41 | 12,928.95 | 4,290.39 | 4,513.57 | 5,058.20 | 2,445.64 |
| 190 | 39,965.50 | 21,130.07 | 25,462.28 | 24,098.88 | 8,640.14 |

Example 15. Preparation of Chemiluminescent-Labeled SBP Including Chemiluminescent Label, Polymeric HRP Conjugate and Streptavidin-Biotin-Coupled Antibody This example demonstrates the preparation of polymeric conjugates of IgG and the enzyme horseradish peroxidase (HRP) and their use as scaffold materials for solution phase immunoassays.

A. Preparation of HRP-IgG Conjugate

For periodate oxidation of the enzyme, HRP was dissolved in water at a concentration of 10 mg/mL. 100 μL of freshly prepared 0.088M sodium periodate was added to the HRP with stirring at 4° C. and allowed to react for the appropriate time (i.e. 20 to 40 minutes). The oxidation reaction was quenched by the addition of a diol, such as ethylene glycol, and allowed to incubate for an additional 20 minutes at 4° C. The oxidized enzyme was desalted on a PD10 column and eluted into an appropriate reaction buffer, such as PBS, to separate the enzyme from excess oxidation and quenching reactants.

Conjugates of oxidized HRP with IgG were prepared by reductive amination. IgG was mixed with oxidized HRP at a 1:1 ratio by volume and a molar ratio of 1:4-15 IgG to HRP. The mixture was allowed to react for two hours to overnight at room temperature. 10 μL of 5M borohydride was added and allowed to react for 30 minutes at room temperature. The reaction product was dialyzed or separated by desalting to remove the excess reducing reagent. The product was then separated by applying the conjugate to an SE HPLC column and collecting conjugates with molecular weight between 450 and 1500 KDa. HRP:IgG ratios were evaluated, and the conjugates are tested in a standard SpectraMax® solution phase SPARCL immunoassay.

Immunoassays for a specific analyte, such as cardiac Troponin I (cTnI), were performed as described in Example 11 using conjugate A, B, or C as described below. Briefly, equal volumes of IgG (33 μg/mL), the HRP conjugate A, B, or C (5 mg/mL), 500 μM ascorbic acid in water, and sample were mixed together in 96-well microtiter plates. The mixture was incubated with trigger solution A, i.e. a trigger solution, to initiate the chemiluminescent reaction. For these assays, cTnI monoclonal antibody M06 was desalted into 100 mM Bicarbonate buffer pH 9.6 with a final concentration of 1-10 mg/mL. Table 31 shows the immunoassay results for cTnI using the polymeric HRP conjugates A, B, or C. These conjugates were prepared substantially as described below:

B. Preparation of Monoclonal cTnI Antibody for Conjugation to Oxidized HRP

Prior to conjugation with oxidized HRP, the cTnI monoclonal antibody was buffer-exchanged into either PBS, pH 7.2 (Conjugates A&B) or sodium carbonate, pH 9.6 (Conjugate C).

C. Conjugate A and B: Oxidation of HRP

HRP was dissolved in water at 5 mg/mL. 100 μL of freshly prepared sodium periodate at a concentration of 8.74 mg/mL (0.088M) was added to each milliliter of HRP with stirring at 4° C. The mixture was allowed to react for appropriate time. For conjugate A, the reaction time was approximately 20 minutes, and for conjugate B, approximately 40 minutes. For each 5 mg of HRP, 17 μL of ethylene glycol was added and incubated for an additional 20 minutes at 4° C. to quench the oxidation reaction. 1.0 mL of oxidized enzyme was desalted on a PD10 column equilibrated in PBS pH 7.2 to remove excess oxidation and quenching reagents.

D. Conjugation with IgG

For conjugates A and B, 2.5 mg oxidized HRP was reacted with 0.4695 mL (2.5 mg) of IgG. The conjugates were allowed to react overnight. 10 μL of 4 mg/mL potassium borohydride was freshly prepared and 10 μL of this solution was added to each milliliter of the reaction mixture. The reaction was allowed to proceed for 30 minutes at room temperature with slow continuous inversion. The product mixture was then separated by desalting into PBS to remove excess reducing reagent. The concentration of IgG following the desalting procedure was 4.26 mg/mL for conjugates A and B. Following conjugation and reduction, the product was separated by applying the conjugate to an SE HPLC column and collecting conjugates with molecular weight between 450 and 1500 KDa. HRP:IgG ratios were evaluated as previously described.

E. Conjugate C: Oxidation of HRP

HRP was dissolved in water at 5 mg/mL. 100 μL of freshly prepared sodium periodate at a concentration of 8.74 mg/mL (0.088M) was added to each milliliter of HRP with stirring at 4° C. The mixture was allowed to react for 20 minutes. 17 μL of ethylene glycol for each 5 mg of HRP was added to quench the oxidation reaction, and the mixture was allowed to incubate for an additional 20 minutes at 4° C.

1.0 mL of oxidized enzyme was desalted on a PD10 column into an appropriate reaction buffer, such as 1 mM acetate buffer at pH 4.5, in order to separate the enzyme from excess oxidation and quenching reactants or reagents.

D. Conjugation with IgG

Oxidized HRP was conjugated with IgG by reductive amination. IgG was mixed with the oxidized HRP at a 1:1 ratio by volume, at an IgG:HRP molar ratio of 1:4-15 and allowed to react for two hours to overnight at room temperature. Just before the combination reaction, 100 μL of 100 mM carbonate buffer at pH 9.6 was added to 1 mL of oxidized HRP. 1 mL of IgG was mixed with the oxidized HRP at a 1:1 ratio by volume, at an approximate IgG:HRP molar ratio of 1:4 HRP and allowed to react for a minimum of two hours. The formed conjugate intermediate was reduced by the addition of 20 μL of freshly prepared 4 mg/mL potassium borohydride. The reduction was allowed to proceed for 30 minutes at room temperature with slow continuous inversion. The mixture was separated by desalting into PBS to remove excess reducing reagent.

Following conjugation and reduction, the product was separated by applying the conjugate to an SE HPLC column and collecting conjugates with molecular weight between 450 and 1500 KDa. HRP:IgG ratios were evaluated as previously described.

TABLE 31

| | [cTnI] ng/mL | STD HRP | A | B | C |
|---|---|---|---|---|---|
| s0 | 0 | 16,299 | 123,078 | 304,943 | 142,975 |
| s1 | 0.039 | 28,111 | 277,115 | 610,073 | 225,401 |
| s2 | 0.28 | 161,298 | 1,957,430 | 4,205,692 | 1,324,504 |
| s3 | 1.04 | 531,785 | 22,820,047 | 47,324,173 | 15,879,973 |
| s4 | 4.47 | 5,957,656 | 330,835,465 | 406,122,102 | 141,011,319 |
| Ratio # | | | | | |
| 1 | s1/s0 | 1.7 | 2.3 | 2.0 | 1.6 |
| 2 | s2/s0 | 9.9 | 15.9 | 13.8 | 9.3 |
| 3 | s3/s0 | 32.6 | 185.4 | 155.2 | 111.1 |
| 4 | s4/s0 | 365.5 | 2688.0 | 1331.8 | 986.3 |

All publications and patent applications in this specification are indicative of the level of ordinary skill in the art to which this invention pertains and are incorporated herein by reference in their entireties.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention without following the example embodiments and applications illustrated and described herein, and without departing from the true spirit and scope of the present invention, which is set forth in the following claims.

The claimed invention is:

[1. A kit for detecting an analyte in a sample comprising:

a chemiluminescent-labeled specific binding partner comprising a first specific binding partner for the analyte, wherein the first specific binding partner is an antibody, and a chemiluminescent compound conjugated to the first specific binding partner;

an activator-labeled specific binding partner comprising a second specific binding partner for the analyte, wherein the second specific binding partner is an antibody, and an activator compound conjugated to the second specific binding partner, wherein the activator compound is a peroxidase enzyme;

a selective signal inhibiting agent; and a trigger solution, wherein all components are soluble in aqueous solution, wherein the chemiluminescent compound is an acridan ketenedithioacetal compound according to the formula

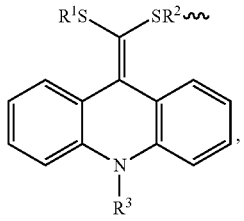

wherein ∿ designates the point of attachment of the chemiluminescent label to the first specific binding partner, wherein $R^1$ and $R^2$ are selected from substituted or unsubstituted lower alkyl, wherein when $R^1$ or $R^2$ is a substituted group, it can be substituted with 1-3 groups selected from the group consisting of carbonyl groups, carboxyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, and quaternary phosphonium groups; and $R^3$ is a benzyl group; and wherein the selective signal inhibiting agent is selected from the group consisting of ascorbic acid, ascorbate sodium salt, 6-hydroxy-2,5,7,8-tetramethylchroman-2-carboxylic acid, phenoxazine, 3-aminotyrosine, and 2-aminophenol.]

[2. The kit of claim 1, wherein the selective signal inhibiting agent is ascorbic acid.]

[3. The kit of claim 1, wherein the chemiluminescent compound is

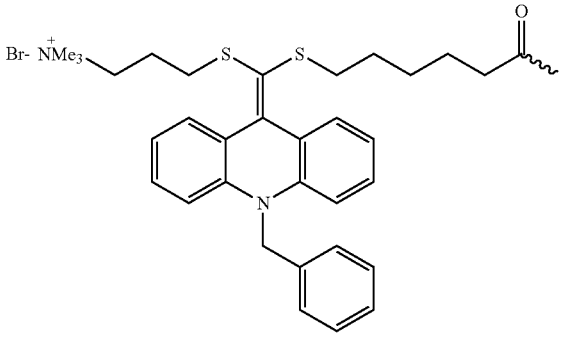

.]

[4. The kit of claim 1, wherein the peroxidase enzyme is selected from the group consisting of lactoperoxidase, microperoxidase, myeloperoxidase, haloperoxidase, vanadium bromoperoxidase, horseradish peroxidase (HRP), fungal peroxidases, lignin peroxidase, peroxidase from Arthromyces ramosus, Mn-dependent peroxidase produced in white rot fungi, and soybean peroxidase.]

[5. The kit of claim 4, wherein the peroxidase enzyme is horseradish peroxidase (HRP).]

[6. The kit of claim 1, wherein the trigger solution comprises a peroxide selected from the group consisting of hydrogen peroxide, urea peroxide, and perborate salts.]

[7. The kit of claim 1, wherein the trigger solution comprises an enhancer selected from the group consisting of phenol compounds, aromatic amines, benzoxazoles, hydroxybenzothiazoles, aryl boronic acids and mixtures thereof.]

[8. The kit of claim 7, wherein the enhancer is a phenol compound selected from the group consisting of p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol.]

[9. The kit of claim 1, wherein at least one of the chemiluminescent-labeled specific binding partner and activator-labeled specific binding partner comprises an auxiliary substance selected from the group consisting of soluble proteins, streptavidin, avidin, neutravidin, biotin, cationized BSA, fos, jun, soluble synthetic dendrimers, soluble synthetic polymers, soluble natural polymers, polysaccharides, dextran, and oligonucleotides.]

*10. A method for detecting an analyte selected from the group consisting of cells, viruses, bacteria, fungi, and combinations thereof in a sample, the method comprising:*

*a) forming an aqueous reaction mixture comprising the following components:*

*the sample;*

*a chemiluminescent-labeled specific binding partner comprising a first specific binding partner for the analyte, wherein the first specific binding partner is an antibody, and a chemiluminescent compound conjugated to the first specific binding partner, wherein the chemiluminescent compound is a compound of the formula:*

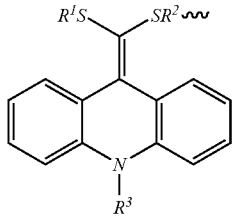

*wherein ∿ designates the point of attachment of the chemiluminescent label to the first specific binding partner wherein $R^1$ and $R^2$ are independently selected from the group consisting of substituted or unsubstituted alkyl, substituted or unsubstituted alkenyl, substituted or unsubstituted alkynyl, substituted or unsubstituted aryl, and substituted or unsubstituted aralkyl groups of 1-20 carbon atoms, wherein when $R^1$ or $R^2$ is a substituted group, it can be substituted with 1-3 groups selected from the group consisting of carbonyl groups, carboxyl groups and quaternary ammonium groups, wherein $R^3$ is selected from the group consisting of alkyl, substituted alkyl, substituted or unsubstituted alkenyl, substituted or unsubstituted alkynyl, substituted or unsubstituted aryl, substituted or unsubstituted aralkyl groups of 1-20 carbon atoms, phenyl, substituted or unsubstituted benzyl groups, alkoxyalkyl, carboxyalkyl and alkylsulfonic acid groups, wherein when $R^3$ is a substituted group, it can be substituted with 1-3 groups selected from the group consisting of carbonyl groups, carbox groups, tri($C_1$-$C_8$ alkyl)silyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, and quaternary phosphonium groups;*

*an activator-labeled specific binding partner comprising a second specific binding partner for the analyte, wherein the second specific binding partner is an antibody, and an activator compound conjugated to the second specific binding partner, wherein the activator compound is a peroxidase enzyme;*

*a selective signal inhibiting agent selected from the group consisting of L-ascorbic acid, 6-hydroxy-2,5,7,8-tetramethylchroman-2-carboxylic acid, 2-aminophenol, 3-amino-L-tyrosine, 4-chlorocatechol, phenoxazine, 2-bromobenzene-1,4-diol, 5,6-isopropylidene ascorbic acid, and ascorbic acid 6-palmitate;*

*by adding the components, in any order or concurrently, to an aqueous solution, wherein all of the components are soluble in the aqueous solution and none of the components are immobilized to a solid support, and wherein the chemiluminescent-labeled specific binding partner and the activator-labeled specific binding partner bind to the analyte present in the sample to form a binding complex in the aqueous solution; and*

*b) adding to the aqueous reaction mixture a trigger solution comprising a peroxide compound, wherein the trigger solution releases a detectable chemiluminescent signal in the presence of the selective signal inhibiting agent that is correlated to the amount of the analyte-bound chemiluminescent-labeled specific binding partner and the analyte-bound activator-labeled specific binding partner in the aqueous reaction mixture, and wherein the selective signal inhibiting agent causes the ratio of signal produced by reaction between the chemiluminescent label compound and the activator label compound in the complex with the analyte to exceed the signal from reaction between the chemiluminescent label compound and the activator label compound when not in such a complex.*

*11. The method of claim 10, wherein the selective signal inhibiting agent is L-ascorbic acid.*

*12. The method of claim 10, wherein the chemiluminescent compound is*

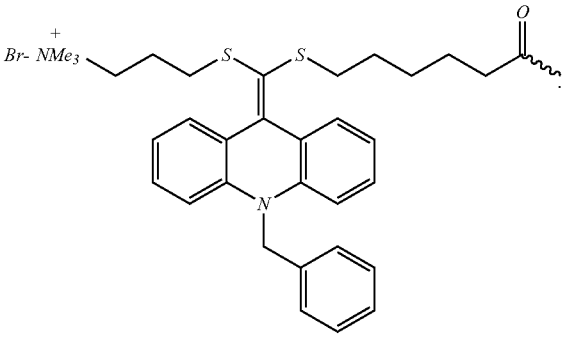

*13. The method of claim 10, wherein the peroxidase enzyme is selected from the group consisting of lactoperoxidase, microperoxidase, myeloperoxidase, haloperoxidase, vanadium bromoperoxidase, horseradish peroxidase (HRP), fungal peroxidases, lignin peroxidase, peroxidase from Arthromyces ramosus, Mn-dependent peroxidase produced in white rot fungi, and soybean peroxidase.*

*14. The method of claim 13, wherein the peroxidase enzyme is horseradish peroxidase (HRP).*

*15. The method of claim 10, wherein the trigger solution comprises a peroxide selected from the group consisting of hydrogen peroxide, urea peroxide, and perborate salts.*

*16. The method of claim 10, wherein the trigger solution comprises an enhancer selected from the group consisting of phenol compounds, aromatic amines, benzoxazoles, hydroxybenzothiazoles, aryl boronic acids and mixtures thereof.*

*17. The method of claim 16, wherein the enhancer is a phenol compound selected from the group consisting of p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol.*

*18. The method of claim 10, wherein at least one of the chemiluminescent-labeled specific binding partner and activator-labeled specific binding partner comprises an auxiliary substance selected from the group consisting of soluble proteins, streptavidin avidin, neutravidin, biotin, cationized BSA, fos, jun, soluble synthetic dendrimers, soluble synthetic polymers, soluble natural polymers, polysaccharides, dextran, and oligonucleotides.*

* * * * *